(12) United States Patent
Wrobel et al.

(10) Patent No.: US 6,355,633 B1
(45) Date of Patent: Mar. 12, 2002

(54) ARYL SULFONIC ACIDS AND DERIVATIVES AS FSH ANTAGONISTS

(75) Inventors: Jay E. Wrobel, Lawrenceville, NJ (US); John F. Rogers, Bryn Mawr, PA (US); Daniel M. Green, Ambler, PA (US); Wenling Kao, Paoli, PA (US); James W. Jetter, Norristown, PA (US)

(73) Assignee: American Home Products Corporation, Madison, NJ (US)

( * ) Notice: Subject to any disclaimer, the term of this patent is extended or adjusted under 35 U.S.C. 154(b) by 0 days.

(21) Appl. No.: 09/535,492

(22) Filed: Mar. 24, 2000

Related U.S. Application Data

(60) Provisional application No. 60/240,926, filed on Mar. 31, 1999.

(51) Int. Cl.[7] .................. A61K 31/167; A61P 15/16; A61P 15/18

(52) U.S. Cl. .............. 514/212.01; 514/238.2; 514/252.11; 514/227.5; 514/445; 514/709; 514/408; 514/316

(58) Field of Search ................. 544/161, 149, 544/357, 54; 514/238.2, 252.11, 227.5, 445, 709, 408, 316, 212.01; 549/64; 548/512; 562/52; 546/186; 540/604

(56) References Cited

U.S. PATENT DOCUMENTS

| 2,567,796 A | 9/1951 | Ackermann | 260/509 |
|---|---|---|---|
| 2,806,054 A | 9/1957 | Eder | 260/490 |
| 2,841,613 A | 7/1958 | Long et al. | 260/509 |
| 2,848,484 A | 8/1958 | Long et al. | 260/507 |
| 3,453,262 A | 7/1969 | Roberts et al. | 260/233.3 |

FOREIGN PATENT DOCUMENTS

| CH | 318441 | 2/1957 |
|---|---|---|
| DE | 250342 | 3/1910 |
| DE | 937822 | 1/1956 |
| DE | 1011889 | 7/1957 |
| DE | 972955 | 2/1960 |
| DE | 2161818 | 7/1972 |
| GB | 2203426 | 10/1988 |
| WO | 9307864 | 4/1993 |
| WO | 9625399 | 8/1996 |

OTHER PUBLICATIONS

Yamashita, Yuki Gosei Kagaku Kyokai Shi, 1970, 28(10), 1025–31.
Yamashita, Yuki Gosei Kagaku Kyokai Shi, 1971, 29(5), 519–25.
Tyman, J. Soc. Dyers Colour., 1965, 81, 102–104.
Yura et al., Chemical Abstracts, 1956, 11675.
Hein et al., J. Am. Chem. Soc., 1954, 76, 2725–2730.
Aleksandrov et al., Chemical Abstracts, 1972, 85:32589.
Gummow et al., Makromol. Chem., 1986, 187(4), 995–1004.
Pestemer et al., Fachorgan Testilveredlung, 1964, 19(6), 420–5.
Macara et al., J. Biol. Chem., 1983, 258(3), 1785–92.

*Primary Examiner*—Richard L. Raymond
*Assistant Examiner*—Hong Liu
(74) *Attorney, Agent, or Firm*—Arnold S. Milowsky

(57) ABSTRACT

This invention provides compounds of formula I having the structure

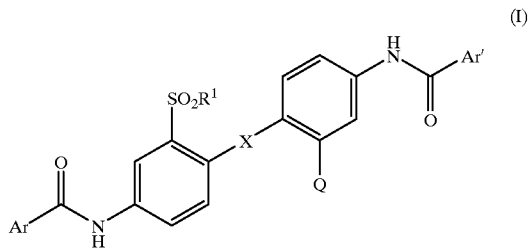

wherein $R^1$, Ar, Ar', and Q are as defined in the specification, or a pharmaceutically acceptable salt thereof, which are useful as contraceptive agents.

3 Claims, No Drawings

ARYL SULFONIC ACIDS AND DERIVATIVES AS FSH ANTAGONISTS

This application claims the benefit of U.S. Provisional Application No. 60/240,926, which was converted from U.S. patent application Ser. No. 09/282,823, filed Mar. 31, 1999, pursuant to a petition filed under 37 C.F.R. 1.53(c)(2)(i).

BACKGROUND OF THE INVENTION

Reproduction in women depends upon the dynamic interaction of several compartments of the female reproductive system. The hypothalamic-pituitary unit orchestrates a series of events affecting the ovaries and the uterine-endometrial compartment which leads to the production of the ovum, ovulation, and ultimately appropriate conditions for fertilization. Specifically, hypothalamic hormones enhance the release of the gonadotropins luteinizing hormone (LH) and follicle stimulating hormone (FSH). In the ovary, gonadotropins enhance the development of follicles which, in turn, secrete steroids (estradiol, progesterone) and peptides (inhibin, activin). Estradiol and inhibin levels progressively increase during the follicular phase of the menstrual cycle until ovulation. Afterwards, the follicular unit forms the corpus luteum which produces progesterone. Ovarian hormones, in turn, regulate the secretion of gonadotropins by establishing a classical long-loop negative feedback mechanism. The elucidation of these control mechanisms has provided opportunities for the development of effective strategies to control fertility, including both the enhancement of fertility and contraception. For recent reviews of FSH action see "FSH Action and Intraovarian Regulation", B. C. J. M. Fauser, editor, Parthenon Publishing Group, 1997 and Hsueh, A. J., Bicsak, T., Jia, X.-C., Dahl, K. D., Fauser, B. C. J. M., Galway, A. B., Czwkala, N., Pavlou, S., Pakoff, H., Keene, J., Boime, I, "Granulosa Cells as Hormone Targets: The role of Biologically Active Follicle-Stimulating Hormone in Reproduction" *Rec. Prog. Horm. Res.,* 1989, 45, 209–277.

Current hormonal contraception methods are steroidal and take advantage of long-loop feedback inhibition of gonadotropin secretion, as well as effecting peripheral mechanisms such as sperm migration and fertilization. An alternative strategy for hormonal contraception would be the development of specific antagonists of the receptor for FSH. Such antagonists would disrupt the actions of FSH on follicular development, thus producing the desired contraceptive effect. The utility of this strategy is supported by mechanism of infertility of women with resistant ovary syndrome. The infertility experienced by these women is the result of non-functional FSH receptors (K. Aittomaki, J. L. D. Lucena, P. Pakarinen, P. Sistonen, J. Tapanainnen, J. Gromoll, R. Kaskikari, E.-M. Sankila, H. Lehvaslaiho, A. R. Engel, E. Nieschlag, I. Huhtaniemi, A. de la Chapelle "Mutation in the Follicle-Stimulating Hormone Receptor Gene Causes Hereditary Hypergonadotropic Ovarian Failure" *Cell,* 1995, 82, 959–968). This approach to contraception also appears applicable to men, since idiopathic male infertility seems related to a reduction in FSH binding sites. Moreover, men with selective FSH deficiency are oligo- or azoospermic with normal testosterone levels and present normal virilization. Therefore, orally active FSH antagonists may provide a versatile method of contraception.

Suramin Sodium, is an anticancer agent with a wide variety of activities. Recently suramin was shown to inhibit FSH binding to its receptor (Daugherty, R. L.; Cockett, A. T. K.; Schoen, S. R. and Sluss, P. M. "Suramin inhibits gonadotropon action in rat testis: implications for treatment of advanced prostate cancer" *J. Urol.* 1992, 147, 727–732). This activity causes, at least in part, the decrease in testosterone production seen in rats and humans that were administered suramin (Danesi, R.; La Rocca, R. V.; Cooper, M. R.; Ricciardi, M. P.; Pellegrini, A.; Soldani, P.; Kragel, P. J.; Paparelli, A.; Del Tacca, M.; Myers, C. E, "Clinical and experimental evidence of inhibition of testosterone production by suramin." *J. Clin. Endocrinol. Metab.* 1996, 81, 2238–2246). Suramin is the only non-peptidic small molecule that has been reported to be an FSH receptor binding antagonist.

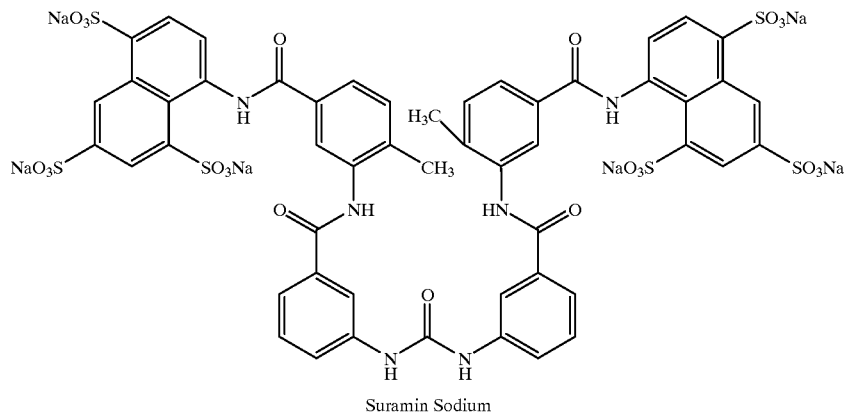

Suramin Sodium

Compounds of formula A are described in the literature as follows:

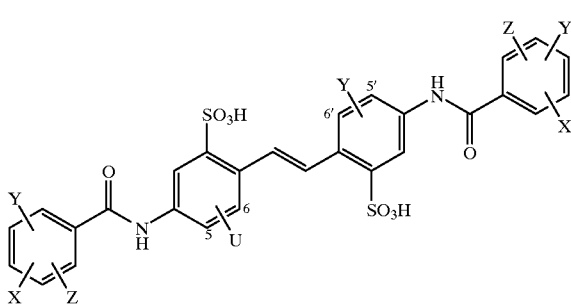

(A)

Y. Yamashita [Yuki Gosei Kagaku Kyokai Shi (1970), 28(10), 1025–31] disclosed compounds of formula A (U, V, X, Y, Z=H) (U, V, Y, Z=H, X=p-$NO_2$) (U, V, Y, Z=H, X=o-$NO_2$) (U, V, Y, Z=H, X=p-OMe) (U, V, Y, Z=H, X=o-OMe) (U, V, Y, Z=H, X=p-Cl) (U, V, Y, Z=H, X=m-Cl) as fluorescent whitening agents.

Y. Yamashita [Yuki Gosei Kagaku Kyokai Shi (1971), 29(5), 519–25] disclosed a compound of formula A (U, V, Y, Z=H, X=o-Cl) as fluorescent whitening agents.

J. H. P. Tyman [J. Soc. Dyers Colour. (1965), 81, 102–104] disclosed a compound of formula A (U, V, Y, Z=H, X=p-$CH_3$).

Yura et al. [Kogyo Kagaku Zasshi (1955) 58, 664–665; CA 1956; 11675] disclosed compounds of formula A (U, V, Y, Z=H, X=p-$NHCH_3$) (U, V, Y, Z=H, X=p-$NHCOCH_3$) (U, V, Y, Z=H, X=p-NHCOPh) (U, V, Y, Z=H, X=p-$NHCH_2OH$).

D. W. Hein and E. S. Pierce [J. Am. Chem. Soc. 1954 (76) 2725–2730] disclosed compounds of formula A (U, V, Y, Z=H, X=o-OEt) (U, V, Y, Z=H, X=o-OPh) (U, V, Z=H, X=o-OMe, Y=p-OMe) (X, Y, Z=H, U=5-Cl, V=5'-Cl) (Y, Z=H, X=p-OMe,U=5-Cl, V=5'-Cl) (Y, Z=H, X=o-OEt, U=5-Cl, V=5'-Cl) (Y, Z=H, X=o-OPh, U=5-Cl, V=5'-Cl) (Z=H, X=o-OMe, Y=p-OMe, U=5-Cl, V=5'-Cl) (Y, Z=H, X=o-OEt, U=6-Cl, V=6'-Cl) (Z=H, X=o-OMe, Y=p-OMe, U=6-Cl, V=6'-Cl).

R. D. Haugwitz, L. Zalkow, E. Gruszecka-Kowalik and E Burgess (WO 9625399) disclosed compounds of formula A (U, V, Y, Z=H, X=o-OH) (U, V Z=H, X=p-$NH_2$, Y=o-$SO_3H$) (U, V, Z=H, X=p-$NO_2$, Y=o-$SO_3H$) (U, V=H, X=o-$CO_2H$, Y=o-OH, Z=m-OH) (U, V Z=H, X=o-OH, Y=m-$CH_2SCH_2CH_2CO_0H$) for treatment of viral infections.

H. J. Roberts (U.S. Pat. No. 3453262) disclosed the compound of formula A (U, V, Z=H, X=p-OMe, Y=p-OMe) as a fluorescent brightening agent.

I. V. Aleksandrov and G. E. Samoliva [Deposited Publ. (1972), Issue VINITI 4341–72; CAN 85:32589] disclosed the compound of formula A (U, V, Y, Z=H, X=p-CN).

B. D. Gummow, G. A. F. Roberts [Makromol. Chem. (1986), 187(4), 995–1004] disclosed the compound of formula A (U, V, Y, Z=H, X=p-$NH_2$).

A compound of formula A (U, V, Y, Z=H, X=m-$NH_2$) was disclosed in DE 250342 (CA 6421-83-6; Beilstein 3526749).

F. Fleck [ Swiss 318,441 (1957)] disclosed compounds of formula A (U, V, Y, Z=H, X=o-$OCH_2CH=CHCH_3$) (U, V, Y, Z=H, X=m-$OCH_2CH=CHCH_3$) (U, V, Y, Z=H, X=o-$OCH_2CH=CH_2$) (U, V, Y, Z=H, X=p-$OCH_2CH=CH_2$) (U, V, Y, Z=H, X=m-$OCH_2CH=CH_2$).

R. Fleischhauer, F. Aldebert [Ger. 1,011,889 (1957)] disclosed compounds of formula A (U, V, Y, Z=H, X=p-$OCH_2C(CH_3)=CH_2$) (U, V, Y, Z=H, X=m-$OCH_2C(CH_3)=CH_2$).

M. Pestemer, A. Berger, A Wagner [Fachorgan Testilveredlung (1964), 19(6) 420–5] disclosed the compound of formula A (U, V, Z=H, X=o-OMe, Y=p-Me).

R. S. Long, A. K. Kantor [U.S. Pat. No. 2,848,484 (1958)] disclosed the compound of formula A (Z=H, X=o-OMe, Y=p-OMe, U=5-OMe, V=5'-OMe).

A. Mitrowsky, O. Bayer [Ger. 937,822 (1956)] disclosed the compound of formula A (U, V=H, X=o-OMe, Y=m-Me, Z=p-Me).

R. S. Long, A. K. Kantor [U.S. Pat. No. 2,841,613 (1958)] disclosed the compound of formula A (Z=H, X=o-OMe, Y=p-OMe, U=5-OMe, V=5'-Cl).

K. W. Eder [U.S. Pat. No. 2,806,054 (1957)] disclosed compounds of formula A (U, V, Y, Z=H, X=p-$OCHCH_2OAc$) (U, V, Y, Z=H, X=p-$OCH_2CH_2OCOPh$).

U.S. Pat. No. 2,567,796 was disclosed compounds of Formula B.

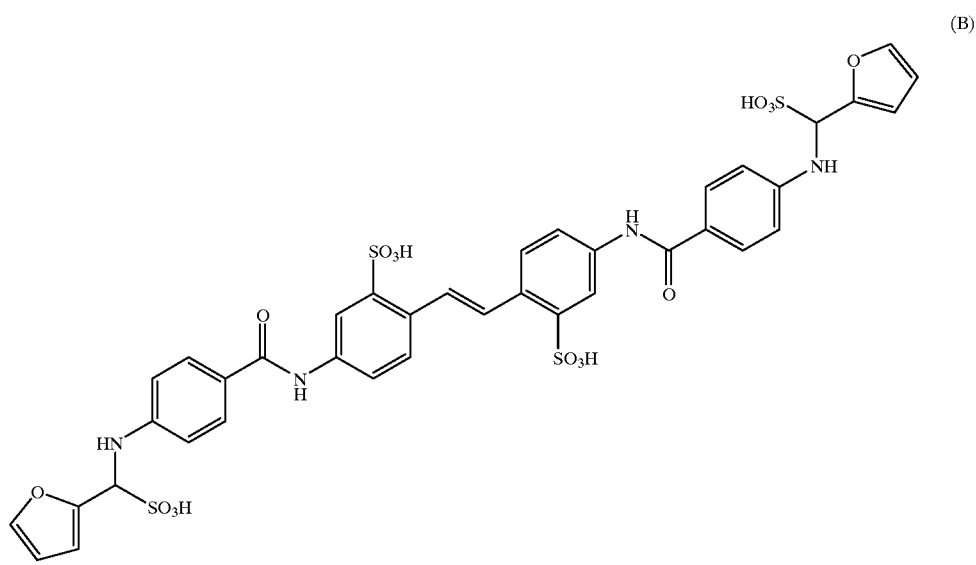

(B)

A compound of formula C is disclosed by I. G. Macara, S. Kuo, and L. C. Cantley in J. Biol. Chem. (1983), 258(3), 1785–92.

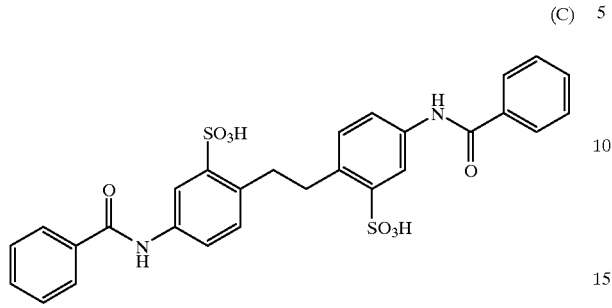

(C)

A compound of formula D is disclosed by A. Froehlich, in Ger. Offen., 47 pp. Addn. To Ger. Offen 1,917,813 (CA 73;50737y), DE 2161818 (1972).

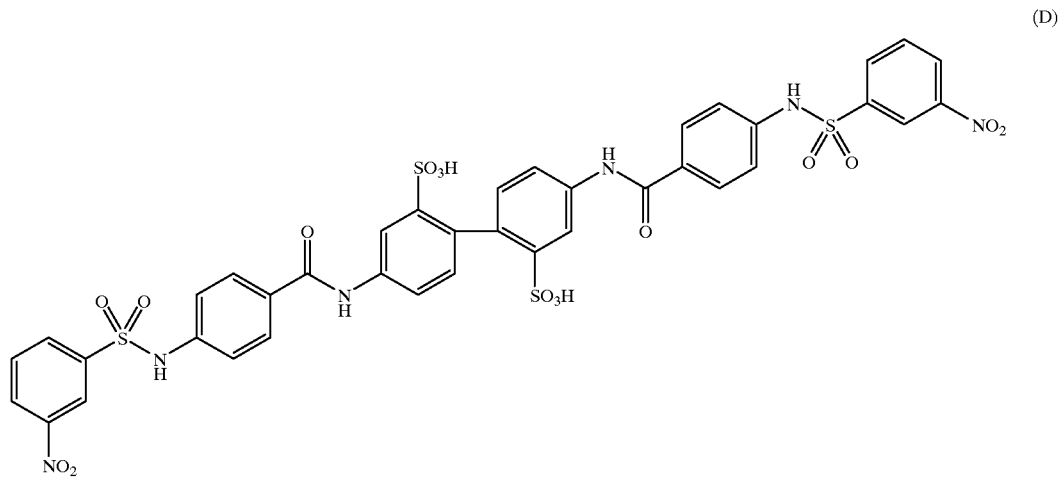

(D)

Compounds of formula E are disclosed by J. M. Farrar in GB2203426 (1988), where $R^Y$ and $R^Z$ are independently substituted alkylamino, alkoxy and alkylthio groups].

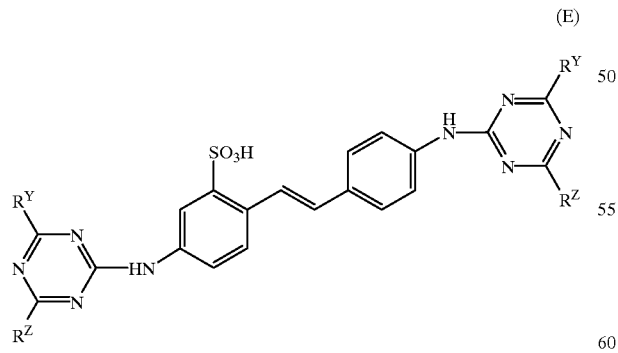

(E)

None of the aforementioned compounds are disclosed to be follicle stimulating hormone (FSH) antagonists or contraceptive agents. Addtionally, none of the aforementioned compounds contain the appropriate substitutions on the pendant benzoyl ring or sulfonate-containing ring required for good activity as FSH antagonists or contraceptive agents contained on the compounds of the present invention.

DESCRIPTION OF THE INVENTION

The compounds useful in this invention have the general formula (I)

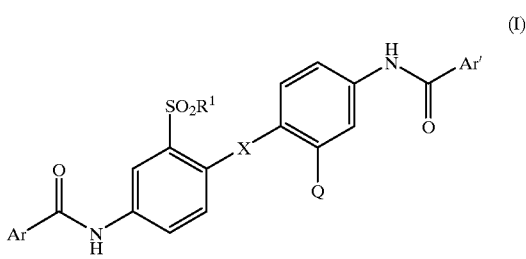

(I)

wherein

Q is hydrogen or $—SO_2R^1$;

X is a bond, O, $S(O)_n$, $—CH=CH—$, $—CH_2CH_2—$, $—C\equiv C—$, or $—CH_2S(O)_nCH_2—$;

$R^1$ is OH, $NH_2$, $C_1$ to $C_6$ alkoxy, $C_1$ to $C_3$ perfluoroalkoxy;

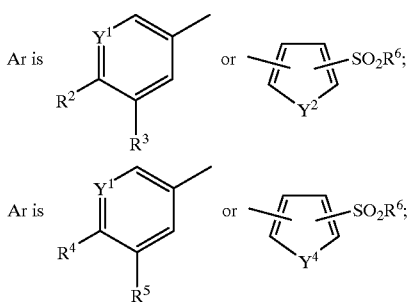

$R^2$ and $R^4$ are each, independently, hydrogen, $OR^6$, $—S(O)_mR^6$, $—NHR^6$, $—N(R^6)_2$, or $—CH_2SO_2CH_3$;

$R^3$ and $R^5$ are each, independently, hydrogen, $—NO_2$, $—NH_2$, $—SO_2R^9$, or $—CH_2R^9$;

R$^6$ is hydrogen, C$_1$ to C$_6$ alkyl, C$_3$ to C$_6$ alkenyl, —CH$_2$CH$_2$Z, —CH$_2$COR$^7$, —CH$_2$CH=CHCOR$^7$,

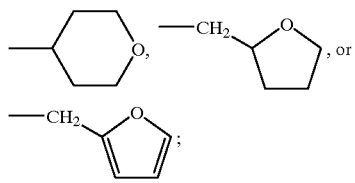

Y$^1$ and Y$^3$ are each, independently, N, or CH;
Y$^2$ and Y$^4$ are each independently, O, S, or NR$^{13}$;
R$^7$ is —OR$^8$, —NHR$^8$, —N(R$^8$)$_2$, or —NHCH$_2$CH$_2$OR$^8$;
Z is —OR$^8$, —OCH$_2$CH$_2$OR$^8$, —N(R$^8$)$_2$, or

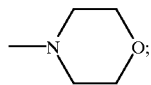

R$^8$ is hydrogen, or C$_1$ to C$_3$ alkyl;
R$^9$ is C$_1$ to C$_6$ alkyl, C$_3$ to C$_6$ alkenyl, OH, NHR$^{10}$, N(R$^{10}$)$_2$, CH$_2$COR$^{11}$, —CH$_2$CH=CHCOR$^{11}$, or

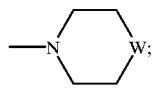

R$^{10}$ is C$_1$ to C$_3$ alkyl, C$_3$ to C$_4$ alkenyl, phenyl, —CH$_2$CH$_2$OCH$_3$, or

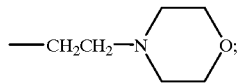

R$^{11}$ is —OR$_{12}$, —NHR$^{12}$, —N(R$^{12}$)$_2$, or —NHCH$_2$CH$_2$OR$^{12}$;
R$^{12}$ is hydrogen, or C$_1$ to C$_3$ alkyl;
R$^{13}$ is hydrogen, or C$_1$ to C$_3$ alkyl;
W is a bond, CH$_2$, CH$_2$CH$_2$, O, S(O)$_q$, NCHO, NCOCH$_3$, or NR$^{12}$;
m is 0 –2;
n is 0–2;
q is 0–2,
with the proviso that R$^2$ and R$^3$ are not both hydrogen; or pharmaceutically acceptable salt thereof.

The compounds of this invention antagonize the binding of hFSH to its receptor, in vitro, and to block cellular functions of FSH, in vitro, including the production of second messenger cAMP and estradiol in ovarian and granulosa cells. The compounds of this invention also inhibit FSH stimulated ovarian and uterine weight gain in immature female rats and ovulation in mature female rats. The compounds of this invention are useful as female and male contraceptive agents.

Preferred compounds of formula I are those in which:
X is a bond, S(O)$_n$, —CH=CH—, —CH$_2$CH$_2$—, or —CH$_2$S(O)$_n$CH$_2$—;
R$^1$ is OH, or C$_1$ to C$_6$ alkoxy;
R$^2$ and R$^4$ are each, independently, hydrogen, OR$^6$, —S(O)$_m$R$^6$, —NHR$^6$, or —N(R$^6$)$_2$;
Y$^1$ and Y$^3$ are CH;

Z is —OR$^8$ or —OCH$_2$CH$_2$OR$^8$;
R$^9$ is NHR$^{10}$, N(R$^{10}$)$_2$, CH$_2$COR$^{11}$, —CH$_2$CH=CHCOR$^{11}$, or

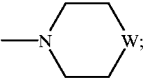

R$^{10}$ is C$_1$ to C$_3$ alkyl, C$_3$ to C$_4$ alkenyl, —CH$_2$CH$_2$OCH$_3$, or

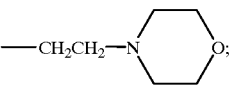

W is a bond, CH$_2$, CH$_2$CH$_2$, O, S(O)$_q$, NCHO, or NCOCH$_3$;
or a pharmaceutically acceptable salt thereof, with the remaining substituents as defined above.

Specifically compounds in this invention include:

2,2'-[(E)-1,2-ethenediyl]bis[5-[[4-(methylthio)-3-(4-morpholinylsulfonyl)benzoyl]amino]benzenesulfonic acid];

2,2-[(E)-1,2-ethenediyl]bis[5-[[4-(methylthio)-3-(4-morpholinylsulfonyl)benzoyl]amino]benzenesulfonic acid], bis(1-methylethyl) ester;

2,2'-[(E)-1,2-ethenediyl]bis[5-[[3-(4-morpholinylsulfonyl)-4-[(tetrahydro-2H-pyran-4-yl)oxy]benzoyl]amino] benzenesulfonic acid];

2,2'-[(E)-1,2-ethenediyl]bis[5-[[4-(2-methoxyethoxy)-3-(4-morpholinylsulfonyl)benzoyl]amino]benzenesulfonic acid;

2,2'-[(E)-1,2-ethenediyl]bis[5-[[4-(methylsulfonyl)-3-(4-morpholinylsulfonyl)benzoyl]amino]benzenesulfonic acid];

2,2'-[(E)-1,2-ethenediyl]bis[5-[[4-[2-(2-methoxyethoxy) ethylthio]-3-(4-morpholinylsulfonyl)benzoyl]amino] benzenesulfonic acid];

2,2'-[(E)-1,2-ethenediyl]bis[5-[[4-(methylsulfonyl)-3-nitrobenzoyl]amino]benzenesulfonic acid];

2,2'-[(E)-1,2-ethenediyl]bis[5-[[4-(methylsulfonyl)-3-nitrobenzoyl]amino]benzenesulfonic acid], bis(1-methylethyl) ester;

2,2'-[(E)-1,2-ethenediyl]bis[5-[[3-[(4-formyl-1-piperazinyl) sulfonyl)-4-methoxybenzoyl]amino]benzenesulfonic acid];

2,2'-[(E)-1,2-ethenediyl]bis[5-[[4-[2-(2-methoxyethoxy) ethoxy]-3-(4-morpholinylsulfonyl)benzoyl]amino] benzenesulfonic acid];

2,2'-[(E)-1,2-ethenediyl]bis[5-[[4-methoxy-3-[[[2-(4-morpholinyl)ethyl]amino]sulfonyl]benzoyl] aminolbenzenesulfonic acid];

5-[[4-methoxy-3-(4-morpholinylsulfonyl)benzoyl]amino]-2-[(E)-2-[4-[[4-(methylsulfonyl)benzoyl]amino]-2-sulfophenyl]ethenyl]benzenesulfonic acid];

5-[[4-methoxy-3-[[(2-methoxyethyl)amino]sulfonyl] benzoyl]amino]-2-[(E)-2-[4-[[4-(methylsulfonyl)-3-nitrobenzoyl] amino]-2-sulfophenyl]ethenyl] benzenesulfonic acid];

5-[[4-methoxy-3-(4-morpholinylsulfonyl)benzoyl]amino]-2-[2-[4-[[4-(methylsulfonyl)benzoyl]amino]-2-sulfophenyl]ethyl]benzenesulfonic acid];

2,2'-[(E)-1,2-ethenediyl]bis[5-[[3-[(1,1-dioxido-4-thiomorpholinyl)sulfonyl]-4-methoxybenzoyl]amino] benzenesulfonic acid];

2,2'-[(E)1,2-ethenediyl]bis[5-[[4-methoxy-3-[[(2-methoxyethyl)amino]sulfonyl]benzoyl]amino]benzenesulfonic acid];

2,2'-[(E)-1,2-ethenediyl]bis[5-[[3-[[bis(2-methoxyethyl)amino]sulfonyl]-4-methoxybenzoyl]amino]benzenesulfonic acid];

2,2'-[(E)-1,2-ethanediyl]bis[5-[[4-methoxy-3-(4-morpholinylsulfonyl)benzoyl]amino]benzenesulfonic acid];

5-[[4-(methylsulfonyl)-3-nitrobenzoyl]amino]-2-[(E)-2-[4-[[4-(methylthio)-3-(4-morpholinylsulfonyl)benzoyl]amino]-2-sulfophenyl]ethenyl]benzenesulfonic acid];

2,2'-[(E)-1,2-ethenediyl]bis[5-[[4-(ethylsulfonyl)benzoyl]amino]benzenesulfonic acid];

2,2'-[(E)-1,2-ethenediyl]bis[5-[[4-(ethylsulfonyl)benzoyl]amino]benzenesulfonic acid], bis(1-methylethyl) ester;

2,2'-[(E)-1,2-ethenediyl]bis[5-[[4-(methoxy)-3-(4-morpholinylsulfonyl)benzoyl]amino]benzenesulfonic acid];

2,2'-[(E)-1,2-ethenediyl]bis[5-[[4-(2-propenylsulfonyl)benzoyl]amino]benzenesulfonic acid];

2,2'-[(E)-1,2-ethenediyl]bis[5-[[4-(ethylthio)-3-morpholinylsulfonyl)benzoyl]amino]benzenesulfonic acid];

2,2'-[(E)-1,2-ethenediyl]bis[5-[[3-[(4-acetyl-1-piperazinyl)sulfonyl]-4-methoxybenzoyl]amino]benzenesulfonic acid;

2,2'-[(E)-1,2-ethenediyl]bis[5-[[4-[(2-ethoxyethyl)amino]-3-(4-morpholinylsulfonyl)benzoyl]amino]benzenesulfonic acid];

2,2'-[(E)-1,2-ethenediyl]bis[5-[[4-(methylsulfonyl)benzoyl]amino]benzenesulfonic acid];

2,2'-[(E)-1,2-ethenediyl]bis[5-[[3-amino-4-(methylsulfonyl)benzoyl]amino]benzenesulfonic acid];

2,2'-[(E)-1,2-ethenediyl]bis[5-[[4-[(2-methoxyethyl)thio]-3-(4-morpholinylsulfonyl)benzoyl]amino]benzenesulfonic acid];

2,2'-[(E)-1,2-ethenediyl]bis[5-[[4-methoxy-3-(1-pyrrolidinylsulfonyl)benzoyl]amino]benzenesulfonic acid];

2,2'-[(E)-1,2-ethenediyl]bis[5-[[4-(methylsulfonyl)benzoyl]amino]benzenesulfonic acid];

2,2'-[(E)-1,2-ethanediyl]bis[5-[[3-[(1,1-dioxido-4-thiomorpholinyl)sulfonyl]-4-methoxybenzoyl]amino]benzenesulfonic acid];

2,2'-[(E)-1,2-ethenediyl]bis[5-[[3-(4-morpholinylmethyl)benzoyl]amino]benzenesulfonic acid];

2,2'-[(E)-1,2-ethenediyl]bis[5-[[4-(dimethylamino)-3-(4-morpholinylsulfonyl)benzoyl]amino]benzenesulfonic acid];

2,2'-[(E)-1,2-ethenediyl]bis[5-[[4-[bis(2-methoxyethyl)amino]-3-(4-morpholinylsulfonyl)benzoyl]amino]benzenesulfonic acid];

2,2'-(1,2-ethanediyl)bis[5-[[4-(2-methoxyethoxy)-3-(4-morpholinylsulfonyl)benzoyl]amino]benzenesulfonic acid];

2,2'-[(E)-1,2-ethenediyl]bis[5-[[4-methoxy -3-(4-thiomorpholinylsulfonyl)benzoyl]amino]benzenesulfonic acid];

5-[[4-(methylsulfonyl)benzoyl]amino]-2-[(E)-2-[4-[[4-[(methylsulfonyl)methyl]benzoyl]amino]-2-sulfophenyl]ethenyl]benzenefulfonic acid;

2,2'-[(E)-1,2-ethenediyl]bis[5-[[4-[(methylsulfonyl)methyl]benzoyl]amino]benzenesulfonic acid];

2,2'-[(E)-1,2-ethenediyl]bis[5-[[3-[(diethylamino)sulfonyl]-4-methoxybenzoyl]amino]benzenesulfonic acid];

5-[[4-(2-methoxyethoxy)benzoyl]amino]-2-[(E)-2-[4-[[4-(methylsulfonyl)benzoyl]amino]-2-sulfophenyl]ethenyl]benzenesulfonic acid;

2,2'-[(E)-1,2-ethenediyl]bis[5-[[3-(4-morpholinylsulfonyl)benzoyl]amino]benzenesulfonic acid];

5-[[4-(2-methoxyethoxy)benzoyl]amino]-2-[(E)-2-[4-[[4-methoxy-3-(4-morpholinylsulfonyl)benzoyl]amino]-2-sulfo-phenyl]ethenyl]benzenesulfonic acid;

2,2'-[1,2-ethanediyl]bis[5-[[4-methoxy-3-(1-pyrrolidinylsulfonyl)benzoyl]amino]benzenesulfonic acid];

2,2'-[(E)-1,2-ethenediyl]bis[5-[[4-(4-morpholinyl)-3-(4-morpholinylsulfonyl)benzoyl]amino]benzenesulfonic acid];

2,2'-[(E)-1,2-ethenediyl]bis[5-[[4-methoxy-3-(1-piperidinylsulfonyl)benzoyl]amino]benzenesulfonic acid];

5-[[4-(2-methoxyethoxy)benzoyl]amino]-2-[2-[4-[[4-methoxy-3-(4-morpholinylsulfonyl)benzoyl]amino]-2-sulfophenyl]ethyl]benzenesulfonic acid;

2,2'-(-1,2-ethanediyl)bis[5-[[3-(4-morpholinylsulfonyl)benzoyl]amino]benzenesulfonic acid];

2,2'-[(E)-1,2-ethenediyl]bis[5-[[3-[(hexahydro-1H-azepin-1-yl)sulfonyl]-4-methoxybenzoyl]amino]benzenesulfonic acid;

2,2'-(1,2-ethanediyl)bis[5-[[4-methoxy-3-(1-piperidinylsulfonyl)benzoyl]amino]benzenesulfonic acid;

4,4'-bis[4-methoxy-3-(morpholine-4-sulfonyl)benzoylamino]biphenyl-2,2'-(bis)sulfonic acid;

2,2'-thiobis[5-[[4-methoxy-3-(4-morpholinylsulfonyl)benzoyl]amino]benzenesulfonic acid;

2,2'-[thiobis(methylene)]bis[5-[[4-methoxy-3-(4-morpholinylsulfonyl)benzoyl]amino]benzenesulfonic acid];

2,2'-[sulfonylbis(methylene)]bis[5-[[4-methoxy-3-(4-morpholinylsulfonyl)benzoyl]amino]benzenesulfonic acid];

2,2'-[(E)-1,2-ethenediyl]bis[5-[[[5-(methylsulfonyl)2-thienyl]carbonyl]amino]benzenesulfonic acid];

[4-(4-{2-[4-(4-methoxycarbonylmethanesulfonyl-benzoylamino)-2-sulfo-phenyl]-vinyl}-3-sulfo-phenylcarbomoyl)-benzenesulfonyl]-acetic acid, methyl ester;

[4-(4-{2-[4-(4-carboxymethanesulfonyl-benzoylamino)-2-sulfo-phenyl]-vinyl-)-3-sulfo-phenylcarbamoyl)-benzenesulfonyl]-acetic acid;

5-[[4-[[2-[(2-hydroxyethyl)amino]-2-oxoethyl]sulfonyl]benzoyl]amino]-2-[(E)-2-[4-[[4-[[2-[(2-hydroxyethyl)amino]-2-oxoethyl]sulfonyl]benzoyl]amino]-2-sulfo-phenyl]ethenyl]benzenesulfonic acid;

5-[[4-[(2-amino-2-oxoethyl)sulfonyl]benzoyl]amino]-2-[(E)-2-[4-[[4-[(2-amino-2-oxoethyl)sulfonyl]benzoyl]amino]-2-sulfophenyl]ethenyl]-benzenesulfonic acid;

[3-(4-{2-[4-(3-methoxycarbonylmethanesulfonyl-benzoylamino)-2-sulfo-phenyl]-vinyl}-3-sulfo-phenylcarbomoyl)-benzenesulfonyl]-acetic acid, methyl ester;

4-{3-[4-(2-{4-{3-(3-methoxycarbonyl-prop-2-ene-1-sulfonyl)-benzoylamino]-2-sulfo-phenyl}-vinyl)-3-sulfo-phenylcarbomoyl]-benzenesulfonyl}-but-2-enoic acid, methyl ester;

[3-(4-{2-[4-(3-carboxymethanesulfonyl-benzoylamino)-2-sulfo-phenyl]-vinyl}-3-sulfo-phenylcarbamoyl)-benzenesulfonyl]-acetic acid;

[4-[4-(2-{4-[4-methoxycarbonylmethylsulfanyl-3-(morpholine-4-sulfonyl)-benzoylamino]-2-sulfo-phenyl}-(E)-vinyl)-3-sulfo-phenylcarbamoyl]-2-(morpholine-4-sulfonyl)-phenylsulfanyl]-acetic acid, methyl ester;

4-{3-[4-(2-{4-[3-(3-carboxy-prop-2-ene-1-sulfonyl)-benzoylamino]-2-sulfo-phenyl}-vinyl)-3-sulfo-phenylcarbomoyl]-benzenesulfonyl}-but-2-enoic acid;

5-[[3-[(2-amino-2-oxoethyl)sulfonyl]benzoyl]amino]-2-[(E)-2-[4-[[3-[(2-amino-2-oxoethyl)sulfonyl]benzoyl]amino]-2-sulfophenyl]ethenyl]-benzenesulfonic acid;

5-[[3-[[2-[(2-hydroxyethyl)amino]-2-oxoethyl]sulfonyl]benzoyl]amino]-2-[(E)-2-[4-[[3-[[2-[(2-hydroxyethyl)amino]-2-oxoethyl]sulfonyl]benzoyl]amino]-2-sulfophenyl]ethenyl]benzenesulfonic acid;

2,2'-(1,2-ethanediyl)bis[5-[[4-(tetrahydro-2-furanmethyl)-3-(4-morpholinylsulfonyl)benzoyl]amino]benzenesulfonic acid];

2,2'-[(E)-1,2-ethenediyl]bis[5-[[4-(2-furanylmethoxy)-3-(4-morpholinylsulfony)benzoyl]amino]benzenesulfonic acid];

N-[3-(aminosulfonyl)-4-[(E)-2-[2-(aminosulfonyl-4-[[4-(methylsulfanyl)-3-(4-morpholinyl-sulfonyl)benzoyl]amino]phenyl]ethenyl]phenyl]-4-(methylsulfanyl)-3-(4-morpholinylsulfonyl)benzamide; and 5-[4-methylsulfanyl-3-(morpholine-4-sulfonyl)-benzoylamino]-2-(2-{[4-methylsulfanyl-3-(morpholine-4-sulfonyl)-benzoylamino]-phenyl}-vinyl)-benzenesulfonic acid;

and pharmaceutically acceptable salts thereof.

Pharmaceutically acceptable salts of the sulfonic acid residues of the compounds of formula (I) can be formed from organic and inorganic bases. For example alkali metal salts: sodium, lithium, or potassium and tetraalkylammonium salts such as tetra-N-butylammonium salts. Similarly, when a compound of this invention contains a carboxylate or phenolic moiety, salts can be formed form organic and inorganic bases. Salts can also be formed from organic and inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable acids when a compound of this invention contains a basic moiety.

The compounds of this invention may contain an asymmetric carbon atom and some of the compounds of this invention may contain one or more asymmetric centers and may thus give rise to optical isomers and diastereomers. While shown without respect to stereochemistry in Formula (I), the present invention includes such optical isomers and diastereomers; as well as the racemic and resolved, enantiomerically pure R and S stereoisomers; as well as other mixtures of the R and S stereoisomers and pharmaceutically acceptable salts thereof.

The term "alkyl" is used herein to refer to both straight- and branched-chain saturated aliphatic hydrocarbon groups having at least one carbon atoms; "alkenyl" is intended to include both straight- and branched-chain alkyl group with at least one carbon-carbon double bond. The term "lower," when used in conjunction with alkyl, alkoxy and the like, indicates less than 6 carbon atoms. This invention covers both the E and Z conformations of such alkenyl moieties, with the E conformation being preferred. The term "perfluoroalkyl" is used herein to refer to both straight- and branched-chain saturated aliphatic hydrocarbon groups having at least one carbon atom and two or more fluorine atoms. Examples include $CF_3$, $CH_2CF_3$, $CF_2CF_3$ and $CH(CF_3)_2$.

The compounds of this invention can be prepared according to standard chemical methodology described in the literature from either commercially available starting material, or starting material which can be prepared as described in the literature. The compounds of this invention can be prepared according to the following synthetic schemes. Unless otherwise noted, Q, Ar, Ar', $R^1$ to $R^{13}$, W, X, $Y^1$ to $Y^4$, Z, q, n, and m are defined above.

Scheme A

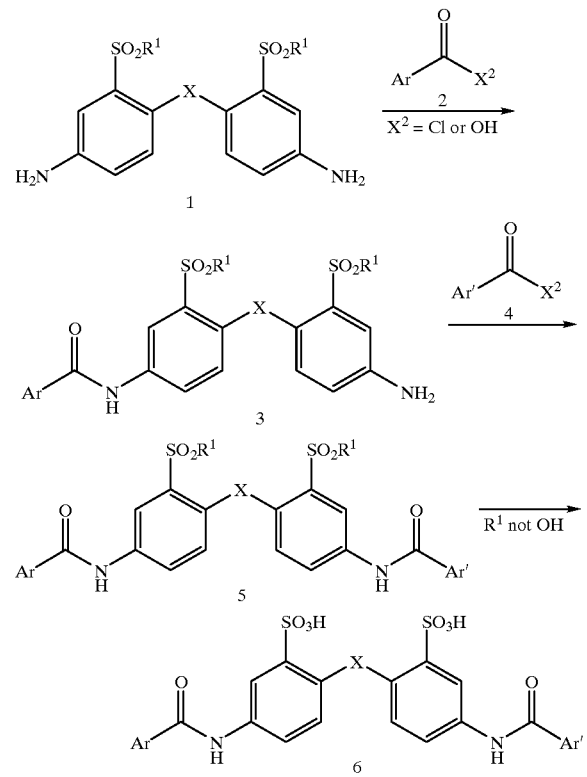

According to Scheme A, compound 1 can be reacted with one or slightly more than one equivalent of an acid chloride 2 ($X^2$=Cl) to produce the compound 3. This reaction is usually performed in the presence of one or more equivalents of a organic amine base such as diisopropylethyl amine or one or more equivalents of an inorganic base such as sodium bicarbonate. Suitable solvents for this transformation include halocarbon solvents such as dichloromethane, THF, dioxane, dimethylacetamide or DMF. Water may be a co-solvent in this process. This reaction is usually performed in the temperature range including 0 to 160° C. over a period of 30 minutes to 48 hours. The acid chloride 2 ($X^2$=Cl) is readily prepared from acid 2 ($X^2$=OH). For example, treatment of the acid 2 ($X^2$=OH) with one or more equivalents of oxalyl chloride in the presence of a catalytic amount of DMF in a halocarbon solvent, such as dichloromethane, at temperatures ranging from 0 to 35° C. will afford acid chloride 2 ($X^2$=Cl).

Alternatively, the compound 3 can be prepared from the compound 1 and the acid 2 ($X^2$=OH) using standard amidation and peptide coupling conditions. For instance, treatment of the acid 2 ($X^2$=OH) with one or more equivalents of a commercially available carbodiimide such as dicyclohexylcarbodiimide (DCC) or 1-(3-dimethylamino)propyl)-3-ethylcarbodiimide hydrochloride (EDCI) and subsequent reaction with the compound 1 results in the formation of the compound 3. The reaction is conveniently performed with or without one or more equivalents of commercially available additive N-hydroxybenzotriazole (HOBT). and with or without one or more equivalents of an organic base such as triethylamine or diisopropylethylamine or an inorganic base such as sodium bicarbonate. Solvents generally useful include halocarbon solvents such as dichlormethane, THF or DMF.

Treatment of compound 3 with one or more equivalents of acid chloride 4 ($X^2$=Cl) or the acid 4 ($X^2$=OH) using conditions described above for the 1 to 3 transformation results in the formation of compound 5. When Ar=Ar' for compound 5, compound 5 can be made directly from compound 1, by employing two or more equivalents of acid chloride 2 ($X^2$=Cl) or acid 2 ($X^2$=OH) and otherwise following the process for the 1 to 3 transformation.

When $R^1$ is OH, the above acylation transformations are most conveniently done by converting the sulfonic acid moieties of 1, 3, or 5 to their tetrabutylammonium salt forms ($R^1$=ONBu$_4$). This conversion is done by treating an aqueous THE solution of 1, 3, or 5 with two or more equivalents of tetrabutylammonium hydroxide at ambient temperatures.

When $R^1$ is not H in the compound 5, this compound can be deesterified to provide the compound 6. This is most conveniently accomplished using one or more molar equivalents of a alkali metal or tetraalkylammonium halide such as sodium iodide, lithium bromide, or tetrabutylammonium chloride in a suitable solvent such as acetone, 2-butanone or DMF with or without a co-solvent such as water at temperatures ranging from 0 to 130° C. and over a time period of one to 48 h. Other methods to effect deesterification to the compound 6 include reacting the compound 5 with one or more equivalents of an organic base such as piperidine and dimethylaminopyridine in an organic solvent such as THF or DMF at temperatures ranging from 20 to 120° C. over periods of 1 h to 64 h.

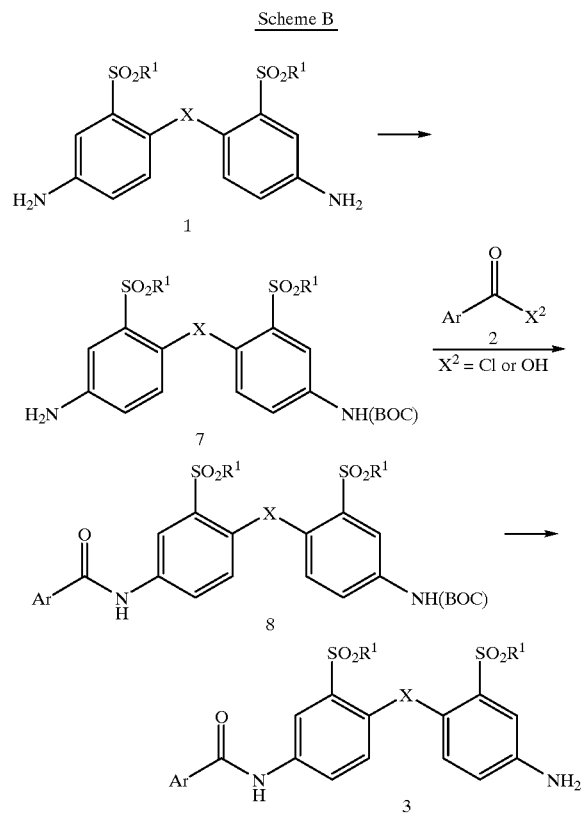

Scheme B

According to Scheme B, the compound 1 can be protected as its mono-BOC derivative 7 (BOC=COOtBu), using standard methods. For example, the compound 1 can be reacted with one equivalent of di-t-butyl-dicarbonate in a THF, dioxane or DMF at temperatures ranging from 0 to 40° C. to afford the BOC protected compound 7. Treatment of compound 7 with one or more equivalents of acid chloride 2 ($X^2$=Cl) or the acid 2 ($X^2$=OH) using conditions described above for the 1 to 3 transformation in Scheme A results in the formation of compound 8. The BOC group of compound 8 can be removed to produce the monoacylated compound 3 using standard conditions. For example, compound 8 can be reacted with one or more equivalents of trifluoroacetic acid in a haloform solvent or using the trifluoroacetic acid as the solvent to provide the compound 3. Compound 3 can be further elaborated as shown in Scheme A.

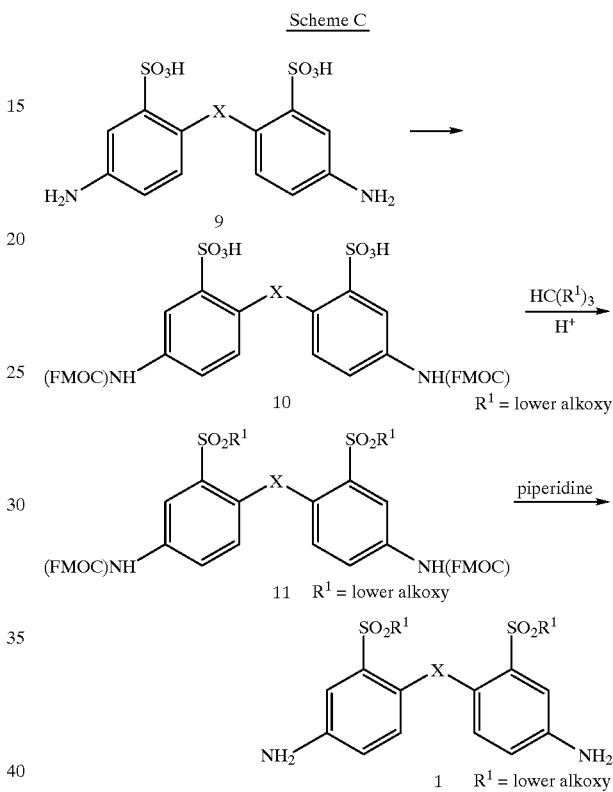

Scheme C

According to Scheme C, the compound 9 can be protected as its FMOC derivative 10 (FMOC=9-fluorenylmethoxycarbonyl) using standard methods. For example, the compound 9 can be treated with one or more equivalents of an alkali metal carbonate, such as sodium carbonate, and two or more equivalents of 9-fluorenylmethyl chloroformate in a lower alcohol solvent such as methanol or a mixture of dioxane/water at temperature ranging from 0 to 40° C. to afford the FMOC protected compound 10.

The compound 10 can then be esterified on the sulfonic acid moiety to the ester 11 using a procedure similar to sulfonic acid esterification methods of A. A Padmapriya, G. Just and N. G. Lewis *Synthetic. Comm.* 1985, 15, 1057–1062 and J. I. Trujillo and A. S. Gopalan *Tetrahedron Lett.* 1993, 34, 7355–7358 employing the commercially available tri-alkylorthoformate [HC($R^1$)$_3$] as the esterification reagent. The acid form of the compound 10 is heated with one or more equivalents of the tri-alkylorthoformate in a suitable solvent such as dioxane at temperatures ranging from 40 to 100° C. over a period ranging from one to 48 h to produce the ester 11.

The FMOC group of the compound 11 can be removed using standard conditions, most notably using one or more equivalents of an organic amine base such as piperidine in a suitable solvent such as DMF or THF to provide the amine 1 ($R^1$=lower alkoxy). This reaction is most conveniently done at the temperature range of 0 to 40° C. over a time period of 5 minutes to 10 h. The compound 1 ($R^1$=lower alkoxy) can then be elaborated according to Scheme A.

Scheme D

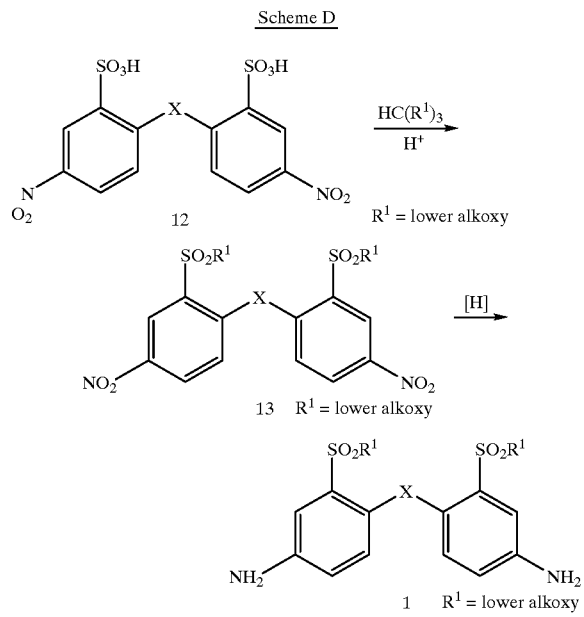

According to Scheme D, the compound 12 can be esterified on the sulfonic acid moiety to the ester 13 using a procedures outlined in Scheme C, employing a commercially available tri-alkylorthoformate [$HC(OR^1)_3$] as the esterification reagent. The nitro groups of ester 13 can be reduced to amino moieties of compound using a variety of standard reducing agents, including, but not limited to, catalytic hydrogenation using a palladium or platinum catalyst, tin chloride in aqueous HCl, ethyl acetate, ethanol, dioxane, THF, or DMF solvents, sodium sulfide in aqueous lower alcohol solvent, and hydrazine and Montmorillinite clay in ethanol. The compound 1 ($R^1$=lower alkoxy) can then be elaborated according to Scheme A.

Scheme E

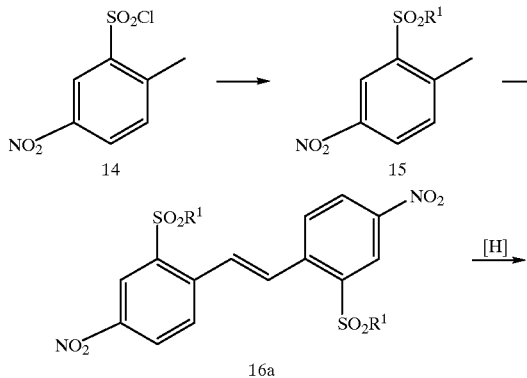

-continued

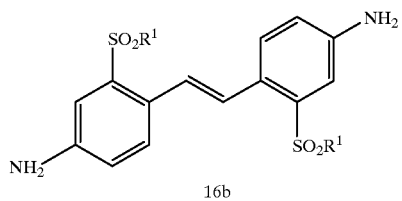

Scheme E illustrates an alternative preparation of stilbene (bis)sulfonic acid subset of the compounds of formula (I). According to Scheme E, the commercially available sulfonyl chloride 14 can be reacted with one or more equivalents of a commercially available alcohol or ammonia under standard conditions to afford the sulfonic acid ester or amide 15 ($R^1$=lower alkoxy, $NH_2$). Standard conditions include, but are not limited to, the use of one or more equivalents of a tertiary amine base such as triethylamine, or pyridine, or an alkali metal carbonate or hydroxide such as sodium carbonate or potassium hydroxide in solvents which can include water, halocarbon, lower alcohol, THF or dioxane, at temperatures ranging from 0 to 80° C. over a time period of 5 minutes to 12 h.

The sulfonic acid derivative 15, can be treated with one or more equivalents of potassium t-butoxide in DMF in the presence of air at 0° C. to ambient temperatures to afford the stilbene analog 16a. The nitro groups of 16a can be reduced to amino compound 16b using a variety of standard reducing agents, including, but not limited to, tin chloride in aqueous HCl, ethyl acetate, ethanol, dioxane, THF, or DMF solvents, sodium sulfide in aqueous lower alcohol solvent, and hydrazine and Montmorillinite clay in ethanol. The compound 16b can then be elaborated according to Scheme A.

Scheme F

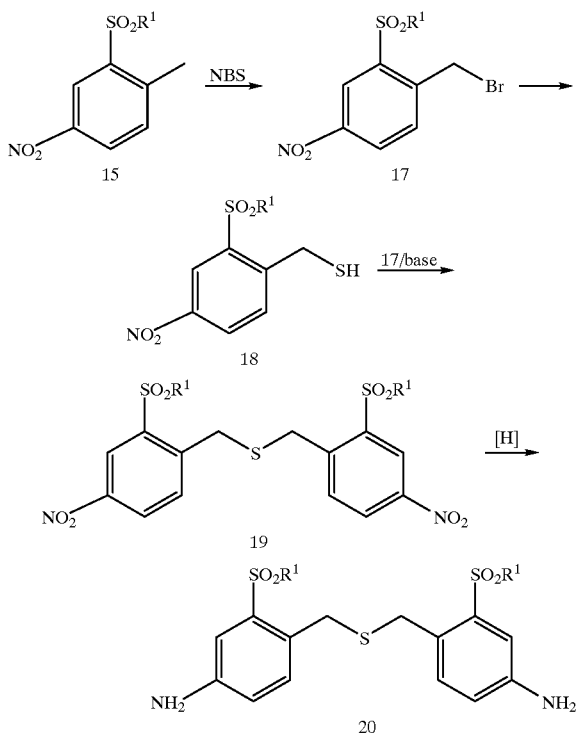

Scheme F illustrates a preparation of thio(bismethylene)-(bis)sulfonic acid subset of the compounds of formula (I). According to Scheme F, the compound 15 can be brominated on the benzylic carbon using to the bromide 17. Typically this is most conveniently done using one equivalent of N-bromosuccinimide (NBS) and a catalytic amount of benzoyl peroxide in an inert solvent such as carbon tetrachloride or dichloromethane at temperatures ranging from 0 to 60° C. over a time period of 30 minutes to 48 h. The bromide 17 can be treated with one or more equivalents of thioacetamide in chloroform at temperatures ranging from from 0 to 60° C. over a time period of 30 minutes to 48 h to afford, after aqueous workup, thiol 18.

The compound 18, can be reacted with the compound 17 using one or more equivalents of a base promoter, such as triethylamine, or potassium carbonate in an inert solvent such as THF, dichloromethane or acetonitrile at temperatures ranging from 0 to 60° C. over a time period of 30 minutes to 48 h to afford the compound 19. The nitro groups of 19 can be reduced to amino compound 20 using a variety of standard reducing agents, including, but not limited to, catalytic hydrogenation using a palladium or platinum catalyst, tin chloride in aqueous HCl, ethyl acetate, ethanol, dioxane, THF, or DMF solvents, sodium sulfide in aqueous lower alcohol solvent, and hydrazine and Montmorillinite clay in ethanol. The compound 20 can then be elaborated according to Scheme A.

Scheme G

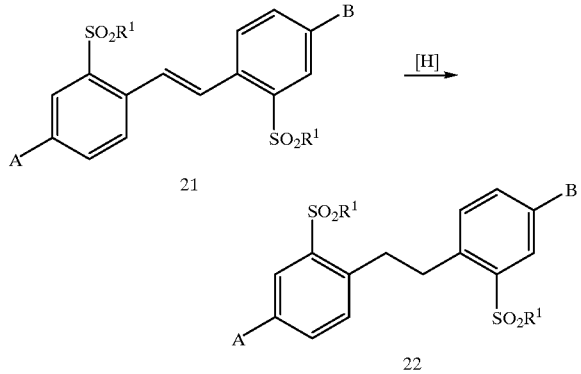

A, B are independent and equal to $NH_2$, NH(FMOC), NH(BOC), NHCOAr, NHCOAr'

A, B are independent and equal to $NH_2$, NH(FMOC), NH(BOC), NHCOAr, NHCOAr'

Scheme G illustrates a preparation of dihydrostilbene (bis)sulfonic acid subset of the compounds of formula (I). According to Scheme G, the double bond of stilbene 21, can be reduced most conveniently by catalytic hydrogenation using a palladium or platinum catalyst in aqueous alcohol to afford the dihydrostilbene 22. Compound 22 [A and/or B is $NH_2$, NH(FMOC), NH(BOC)] can be further elaborated according to Schemes A–D.

Scheme H

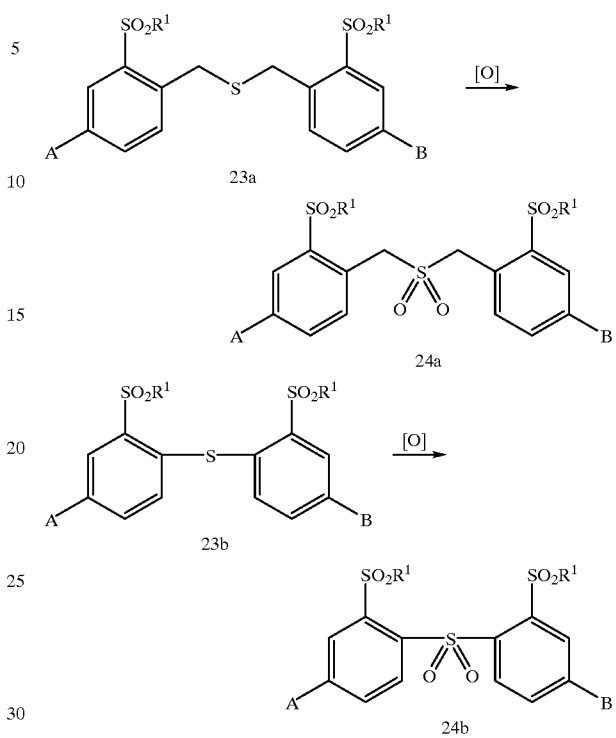

A, B are independent and equal to $NO_2$, $NH_2$, NH(FMOC), NH(BOC), NHCOAr, NHCOAr'

According to Scheme H, the thioethers 23a or 23b can be converted to their sulfone derivatives 24a or 24b respectively using two or more molar equivalents of an oxidizing agent such as oxone in an aqueous alcohol solvent at temperatures ranging from room temperature to 100° C., m-chloroperbenzoic acid in dichloromethane at temperatures ranging from −20° C. to 60° C. or hydrogen peroxide in acetic acid at temperatures ranging from room temperature to 100° C. Compounds 24a or 24b [A and/or B is $NH_2$, NH(FMOC), NH(BOC)] can be further elaborated according to Schemes A–D.

The carboxylic acids, $ArCO_2H$ and $Ar'CO_2H$ are prepared according to Schemes I through L.

Scheme I

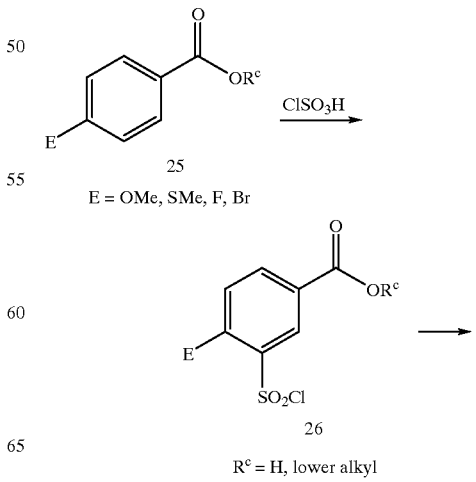

E = OMe, SMe, F, Br $R^c$ = H, lower alkyl

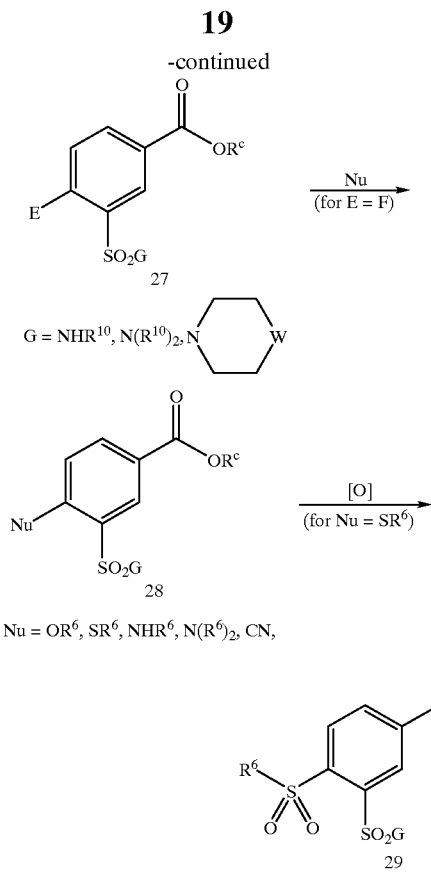

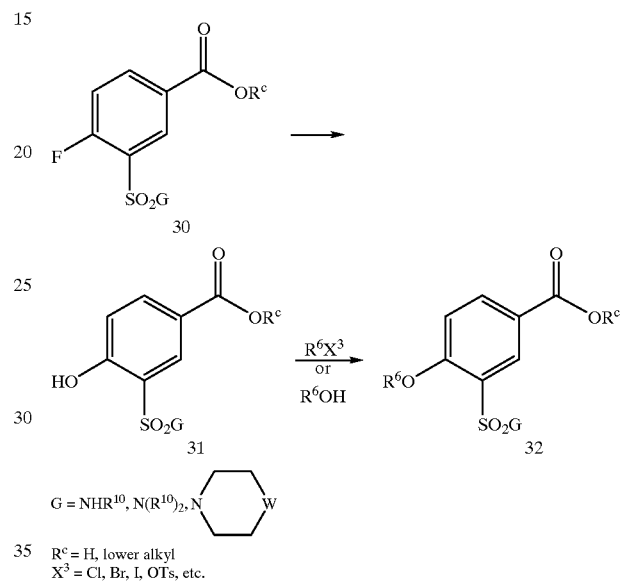

The reactions for compounds 25–29 can generally be carried out on the acid form ($R^c$=H) or the ester form ($R^c$ is lower alkyl). For the target products of Scheme I (compounds 27–29) to be properly utilized in Schemes A and B, esters of 27–29 ($R^c$ is lower alkyl) must be converted to their acid forms ($R^c$=H). The conditions to most conveniently effect these transformations include aqueous base in which one or more molar equivalents of alkali metal hydroxide such as sodium, lithium or potassium hydroxide is used in water with a co-solvent such as THF, dioxane or a lower alcohol such as methanol or mixtures of THF and a lower alcohol at temperatures ranging from 0° C. to 40° C.

Scheme I illustrates the preparation of benzoic acid analogs that can be used in the preparation of target compounds outlined in Scheme's A and B. Acid derivative 25 can be treated with neat chlorosulfonic acid at temperatures ranging from −20° C. to 150° C. to afford the sulfonyl chloride derivatives 26. The compounds 26 can be treated with a variety of primary or secondary amines in an inert solvent such as dichloromethane or THF at temperatures ranging from 0° C. to 50° C. to provide the sulfonamide derivatives 27.

Treatment of 27 [E=F (fluorine)] with nucleophiles such as alkoxides ($OR^6$), thiolates ($SR^6$), and amines ($NH_2R^6$, $NH(R^6)_2$) affords compounds 28 in which the nucleophilic moiety replaces the fluoride atom of 27. Solvents for this reaction include water, THF, dioxane, DMF, acetonitrile, dichloromethane, lower alcohol, or combinations of these solvents. The reactions can be conveniently performed at temperatures ranging from −20° C. to 150° C. over a 5 minute to 48 hr period. The alkoxide or thiolate nucleophiles are generally prepared in situ by treating one or more equivalents of the corresponding alcohol ($HOR^6$) or thiol ($HSR^6$) with more than one equivalent amount of a base such as sodium hydride, butyl lithium, potassium carbonate or triethylamine. When amines ($NH_2R^6$, $NH(R^6)_2$) are used as nucleophiles, one or more equivalents of these reagents are used.

When Nu of 28 is $SR^6$, the thioether sulfour atom of 28 can be oxidized to the sulfone 29. This oxidation is most conveniently done using two or more molar equivalents of an oxidizing agent such as oxone in an aqueous alcohol solvent at temperatures ranging from room temperature to 100° C., m-chloroperbenzoic acid in dichloromethane at temperatures ranging from −20° C. to 60° C. or hydrogen peroxide in acetic acid at temperatures ranging from room temperature to 100° C.

Scheme J further illustrates the preparation of benzoic acid analogs that can be used in the preparation of target compounds outlined in Scheme's A and B. Compound 31 can be prepared from compound 30 via a two-step, one pot reaction. In this regard, compound 30 can be reacted with the sodium salt of 2-(methylsulfonyl)ethanol. The alcohol moiety of 2-(methylsulfonyl)ethanol displaces the fluorine atom of 30. Subsequently, in situ, or during aqueous workup, vinyl-methylsulfone is released from the 30/2-(methylsulfonyl)ethanol adduct via an E2 type of elimination reaction to afford the phenol 31. This reaction is most conveniently done employing one or more equivalents of 2-(methylsulfonyl)ethanol and three or more equivalents of sodium hydride as the base. The reaction can be performed within the temperature range of 0° C. to 40° C., within a 5 min to 12 h period. Suitable solvents include DMF, THF, dioxane, and acetonitrile.

The phenol 31 can be alkylated with one or more molar equivalents of an alkyl halide, tosylate, mesylate or triflate ($R^6X^3$, $X^3$ is Cl, Br, I, $OSO_2Ph$, $OSO_2CH_3$, $OSO_2CF_3$) using one or more molar equivalents of an alkali metal carbonate such as potassium carbonate or one or more equivalent of an alkali metal hydride such as sodium hydride in a polar aprotic solvent such as DMF to afford the alkylated phenol 32. Alternatively, the phenol 31 can be reacted with an alcohol $R^6OH$ to afford compound 32 under the conditions of the Mitsunobu reaction. The other co-reagents necessary to effect the Mitsunobu reaction include one or more molar equivalents of an alkyl of 1–6 carbon atoms azodicarboxylate diester such as diethyl azodicarboxylate or diisopropyl azodicarboxylate and one or more molar equivalents of triarylphosphine such as triphenylphosphine in a suitable solvent such as diethyl ether, THF, benzene or toluene at temperatures ranging from −20° C. to 120° C.

The reactions for compounds 32 can generally be carried out on the acid form ($R^c$=H) or the ester form ($R^c$ is lower alkyl). For the target products of Scheme J (compound 32) to be properly utilized in Schemes A and B, esters of 32 ($R^c$ is lower alkyl) must be converted to their acid forms ($R^c$=H). The conditions to most conveniently effect these transformations include aqueous base in which one or more molar equivalents of alkali metal hydroxide such as sodium, lithium or potassium hydroxide is used in water with a co-solvent such as THF, dioxane or a lower alcohol such as methanol or mixtures of THF and a lower alcohol at temperatures ranging from 0° C. to 40° C.

Scheme K

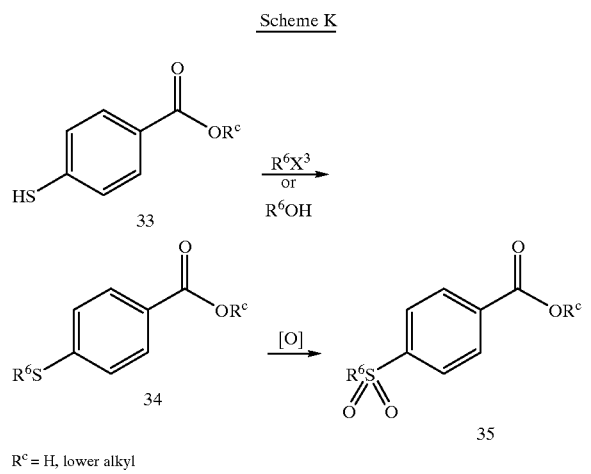

$R^c$ = H, lower alkyl

Scheme K further illustrates the preparation of benzoic acid analogs that can be used in the preparation of target compounds outlined in Scheme's A and B. The thiophenol 33 can be alkylated with one or more molar equivalents of an alkyl halide, tosylate, mesylate or triflate ($R^6X^3$, $X^3$ is Cl, Br, I, $OSO_2Ph$, $OSO_2CH_3$, $OSO_2CF_3$) using one or more molar equivalents of an alkali metal carbonate or hydroxide such as potassium carbonate or potassium hydroxide, one or more equivalent of an alkali metal hydride such as sodium hydride or one or more equivalents of a tertiary amine such as triethylamine in a polar aprotic solvent such as DMF or in an lower alcohol solvent such as ethanol or a halocarbon solvent such as dichloromethane to afford the thioether 34. Alternatively, the thiophenol 33 can be reacted with an alcohol $R^6OH$ to afford compound 34 under the conditions of the Mitsunobu reaction. The other co-reagents necessary to effect the Mitsunobu reaction include one or more molar equivalents of a alkyl of 1–6 carbon atoms azodicarboxylate diester such as diethyl azodicarboxylate or diisopropyl azodicarboxylate and one or more molar equivalents of triarylphosphine such as triphenylphosphine in a suitable solvent such as diethyl ether, THF, benzene or toluene at temperatures ranging from −20° C. to 120° C.

The thioether sulfur atom of 34 can be oxidized to the sulfone 35. This oxidation is most conveniently done using two or more molar equivalents of an oxidizing agent such as oxone in an aqueous alcohol solvent at temperatures ranging from room temperature to 100° C., m-chloroperbenzoic acid in dichloromethane at temperatures ranging from −20° C. to 60° C. or hydrogen peroxide in acetic acid at temperatures ranging from room temperature to 100° C.

The reactions for compounds 35 can generally be carried out on the acid form ($R^c$=H) or the ester form ($R^c$ is lower alkyl). For the target products of Scheme K (compound 35) to be properly utilized in Schemes A and B, esters of 35 ($R^c$ is lower alkyl) must be converted to their acid forms ($R^cH$). The conditions to most conveniently effect these transformations include aqueous base in which one or more molar equivalents of alkali metal hydroxide such as sodium, lithium or potassium hydroxide is used in water with a co-solvent such as THF, dioxane or a lower alcohol such as methanol or mixtures of THF and a lower alcohol at temperatures ranging from 0° C. to 40° C.

Scheme L

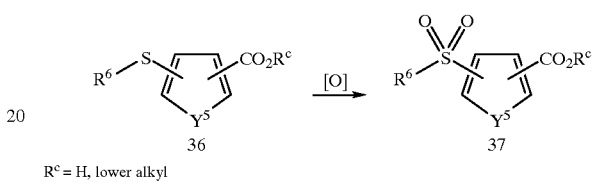

$R^c$ = H, lower alkyl

Scheme L illustrates the preparation of sulfonyl-substituted thiophene carboxylic acid analogs that can be used in the preparation of target compounds outlined in Scheme's A and B. The thioether sulfur atom of 36 can be oxidized to the sulfone 37. This oxidation is most conveniently done using two or more molar equivalents of an oxidizing agent such as oxone in an aqueous alcohol solvent at temperatures ranging from room temperature to 100° C., m-chloroperbenzoic acid in dichloromethane at temperatures ranging from −20° C. to 60° C. or hydrogen peroxide in acetic acid at temperatures ranging from room temperature to 100° C.

The reactions for compounds 37 can generally be carried out on the acid form ($R^c$=H) or the ester form ($R^c$ is lower alkyl). For the target products of Scheme L (compound 37) to be properly utilized in Schemes A and B, esters of 37 ($R^c$ is lower alkyl) must be converted to their acid forms ($R^c$=H). The conditions to most conveniently effect these transformations include aqueous base in which one or more molar equivalents of alkali metal hydroxide such as sodium, lithium or potassium hydroxide is used in water with a co-solvent such as THF, dioxane or a lower alcohol such as methanol or mixtures of THF and a lower alcohol at temperatures ranging from 0° C. to 40° C.

Scheme M

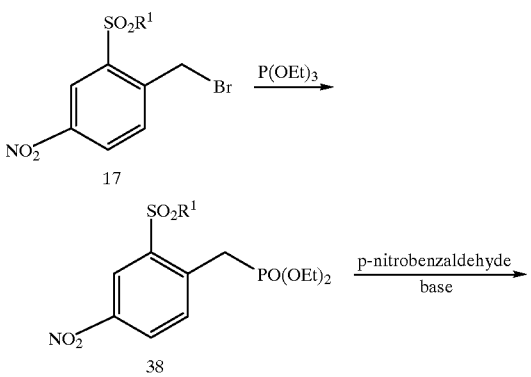

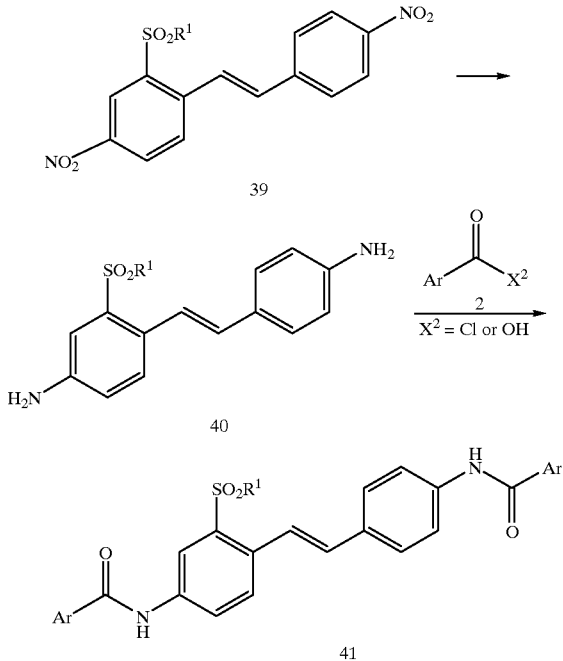

Scheme M illustrates a preparation of stilbene (mono) sulfonic acid subset of the compounds of formula (I). According to Scheme M, bromide 17 can be reacted with one or more equivalents of triethylphosphite to afford the phosphonate 38. The transformation 17 to 38 is known as the Arbuzov reaction. Typically this reaction is done in an inert solvent such as dichloromethane, acetonitrile, DMF or THF at temperatures ranging from room temperature to 150° C.

Compound 38 can undergo a Homer-Emmons condensation reaction with one or more equivalents of p-nitrobenzaldehyde to afford the stilbene 39. One or more equivalents of a base is used to promote this reaction. Typical bases include butyl lithium, potassium hydroxide, potassium t-butoxide and sodium hydride. Typically this reaction is done in an inert solvent such as a lower alcohol, DMF or THF at temperatures ranging from 0° C. to 150° C.

The nitro groups of compound 39 can be reduced to amino moieties of compound 40 using a variety of standard reducing agents, including, but not limited to, catalytic hydrogenation using a palladium or platinum catalyst, tin chloride in aqueous HCl, ethyl acetate, ethanol, dioxane, THF, or DMF solvents, sodium sulfide in aqueous lower alcohol solvent, and hydrazine and Montmorillinite clay in ethanol. Compound 40 can be reacted with two or more equivalents of an acid chloride 2 ($X^2$=Cl) to produce the compound 41. This reaction is usually performed in the presence of two or more equivalents of a organic amine base such as diisopropylethyl amine or one or more equivalents of an inorganic base such as sodium bicarbonate. Suitable solvents for this transformation include halocarbon solvents such as dichloromethane, THF, dioxane, dimethylacetamide or DMF. Water may be a co-solvent in this process. This reaction is usually performed in the temperature range including 0 to 160° C. over a period of 30 minutes to 48 hours. The acid chloride 2 ($X^2$=Cl) is either commercially available or readily prepared from commercially available acid 2 ($X^2$=OH). Standard reagents and conditions are used to effect the acid to acid chloride transformation, for example, treatment of the acid 2 ($X^2$=OH) with one or more equivalents of oxalyl chloride in the presence of a catalytic amount of DMF in a halocarbon solvent, such as dichloromethane, at temperatures ranging from 0 to 35° C. will afford acid chloride 2 ($X^2$=Cl).

Alternatively, the compound 41 can be prepared from the compound 40 and the acid 2 ($X^2$=OH) using standard amidation and peptide coupling conditions. For instance, treatment of the acid 2 ($X^2$=OH) with two or more equivalents of a commercially available carbodiimide such as dicyclohexylcarbodiimide (DCC) or 1-(3-dimethylamino) propyl)-3-ethylcarbodiimide hydrochloride (EDCI) and subsequent reaction with the compound 40 results in the formation of the compound 42. The reaction is conveniently performed with or without one or more equivalents of commercially available additive N-hydroxybenzotriazole (HOBT). and with or without one or more equivalents of an organic base such as triethylamine or diisopropylethylamine or an inorganic base such as sodium bicarbonate. Solvents generally useful include halocarbon solvents such as dichlormethane, THF or DMF.

Scheme N

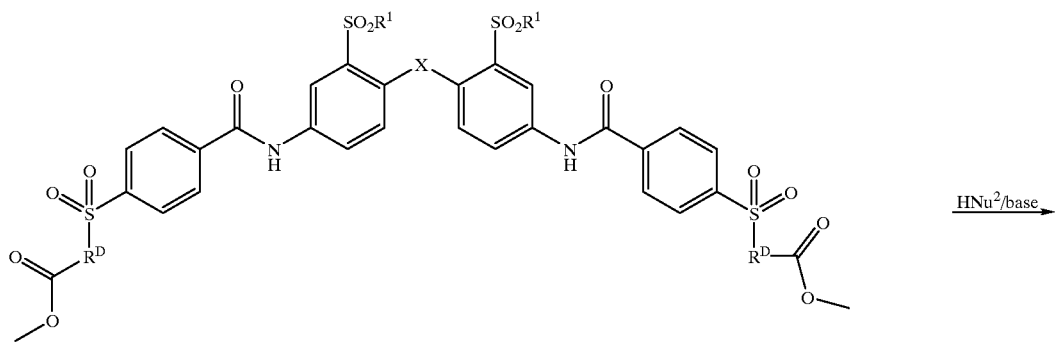

$R^D$ is —$CH_2$— or —$CH_2CH$=$CH$—

$Nu^2 = R^{11}O, R^{11}NH, (R^{11})_2N$

-continued

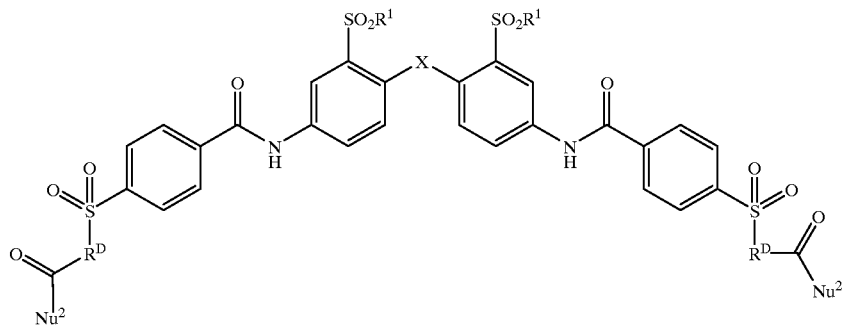

43

Scheme N illustrates further ellaboration of certain bis (sulfonic) acid derivatives 42. The compounds 42 can be converted to the carboxylic acid forms 43 ($Nu^2$=OH). The conditions to most conveniently effect these transformations include aqueous base in which one or more molar equivalents of alkali metal hydroxide such as sodium, lithium or potassium hydroxide is used in water with a co-solvent such as THF, dioxane or a lower alcohol such as methanol or mixtures of THF and a lower alcohol. at temperatures ranging from 0° C. to 40° C.

The compounds 42 can also be converted to the carboxylic acid amide forms 43 ($Nu^2$=$R^{11}$NH, $(R^{11})_2$N). The conditions used to effect this transformation include reaction of 42 with one or more equivalents of a primary or secondary amine (HNu2=$R^{11}NH_2$, $(R^{11})_2$NH) in a suitable solvent such as a lower alcohol solvent, THF or DMF at temperatures ranging from 0° C. to 120° C.

The FSH antagonist activities of the compounds of this invention were demonstrated by evaluating representative compounds of this invention in three in vitro FSH antagonist and one in vivo standard pharmacological test procedures.
FSH Receptor Radioligand Membrane Binding Standard Pharmacological Test Procedure Membrane Source: Chinese hamster ovarian cells stably transfected with the human FSH receptor were cultured (Ultra CHO medium containing 1% fetal bovine serum and 200 μg/mL G418) in and harvested. Cells were collected by centrifugation and resulting cell pellets were frozen and stored at −70° C.

Membrane Receptor Preparation: Frozen cell pellets were weighed and resuspended in binding buffer to a final concentration of 30 mg wet weight/mL. Cell suspension for each pellet was homogenized using a Tempest homogenizer (setting=1; 5 strokes; VirTis, Gardiner, N.Y.). Cell homogenates were pooled and 35 mL aliquots were transferred to 50-mL polypropylene copolymer centrifuge tubes (Nalgene cat. #3110-0500). Tubes were spun at 12,000 rpm (SS34 rotor) for 12 min at 4° C. Resulting supernatant fractions were discarded and pellets were stored at −70° C. until use. On the day of the procedure, 35 mL binding buffer was added to each tube (35 mL membrane suspension was sufficient for three 96-well plates). The membrane pellet was dispersed by trituration using a pipet. The resulting suspension wass homogenized using a Tempest homogenizer (3 strokes at setting=1).

Receptor Binding Test procedure: Membrane homogenate (100 μl) was added to each well of a 96-well microtiter plate (Falcon # 3077). All reactions were tested in triplicate. Test compound solutions (50 μl) were added to the designated wells. Total bound counts were determined by adding 50 μl binding buffer containing 4% DMSO to the designated wells. Non-specific binding was determined by adding 50 μl of hFSH solution to the designated wells. Plates were pre-incubated for 15 min at room temperature on shaking platform (setting=3). After preincubation [$^{125}$I]FSH (50 μl) was added to each well and plates were incubated for 2 h at room temperature on shaking platform (setting=3). The reaction was terminated by transfer of the membrane preparation to glass fiber filters (Blue Mat #11740; 102×256 mm; Skatron Instruments, Sterling, Va.) that had been pretreated with 1% BSA in wash buffer for at least 30 min, but not longer than 1 h using a 96-well microtiter vacuum harvester (Skatron Instruments). The membrane preparation was washed with 5 cycles of ice-cold wash buffer (200 μl/well/cycle) followed by a pulse wash of 3 cycles (100 μl/well/cycle). The total wash volume per well was 1.3 mL. The filters were dried by a 10 sec aspiration. Disks corresponding to each well of the microtiter plate were punched out of the filter mat into 12×75 mm polypropylene tubes. The radioactivity present on each of the disks was measured using a gamma counter.

An FSH dose response curve (0.001, 0.01, 0.1, 1, 10, and 100 nM) was generated for each binding procedure to monitor procedure to procdrue variability.
FSH Receptor Radioligand Membrane Binding Procedure Buffers and Reagents

| | |
|---|---|
| Binding Buffer (pH 7.2): | 10 mM Trizma ®-HCl (Sigma) |
| | 1 mM $MgCl_2$ |
| | 1 mM $CaCl_2$ |
| | 0.025% (w\v) Sodium azide |
| | 0.1)% (w/v) Bovine serum albumin (fraction V; Sigma) |
| | 5 μg/mL Aprotinin |
| | 5 μg/mL Leupeptin |
| | 5 μg/mL Pepstatin |
| | 5 μg/mL Phenylmethylsulfonylfluoride |
| | 5 μg/mL Phosphoramidon |

Binding buffer is prepared in 1l volumes containing Trizma-HCl, $MgCl_2$, $CaCl_2$ and sodium azide, the pH was adjusted to 7.2 with NaOH, and stored at 4° C. until use. BSA was weighed out on the day of the procedure and added to the amount of buffer required for the procedure (usually 150 mL). The protease inhibitors were prepared as 1 mg/mL stocks (aprotinin, leupeptin, and phosphoramidon were prepared in binding buffer without BSA and protease inhibitors; pepstatin and PMSF were prepared in methanol), stored in 1 mL aliquots at −70° C., and added to the binding buffer on the day of the procedure.

Wash Buffer (pH 7.2): 50 mM Trizma ®-HCl (Sigma)
10 mM MgCl$_2$
0.5) mM EDTA

Wash buffer was prepared containing Trizma-HCl, MgCl$_2$ and EDTA, the pH was adjusted to 7.2 with NaOH, and stored at 4° C.

Filter Soak Buffer (pH 7.2)

Wash Buffer

1% BSA

BSA was weighed out on the day of the procedure and added to 300 mL of wash buffer. The filter soak buffer was used for two procedures before being discarded.

[$^{125}$I]hFSH Solution: The concentration of the [$^{125}$I]hFSH stock solution was determined by measuring the radioactivity in three 10 μl samples of the stock solution using a gamma counter. The concentration was calculated using the radioactivity measurement (cpm), counting efficiency (0.8) to convert cpm to dpm and subsequent conversion of dpm to μCi, specific activity μCi/μg FSH) of the [$^{125}$I]hFSH given on the specification sheets from NEN, and the molecular weight of FSH (29,695). A portion of the stock solution was diluted in binding buffer to a concentration of 200 pM.

FSH Solution for Determining Non-specific Binding: Purified human FSH was prepared as a 100 μM solution in binding buffer without protease inhibitors. This stock was stored as 30 μl aliquots at −70° C. The stock was diluted on the day of the procedure to 4 μM in binding buffer containing 4% DMSO on the day of the procedure.

Compound Solutions: Each compound to be tested was prepared as a 400 μM solution in DMSO. For additional concentrations, the 400 μM stock solution was diluted with binding buffer containing 4% DMSO.

REFERENCES

1) McPherson, G. A. 1985. Kinetic, EBDA, Ligand, Lowry: a collection of radioligand binding analysis programs. BIOSOFT, Cambridge, U. K.
2) Schneyer, A. L., Sluss, P. M., Bosukonda, D. and Reichert, L. E. "Electrophoretic Purification of Radioiodinated Follicle-Stimulating Hormone for Radioligand Receptor Assay and Radioimmunoassay." *Endocrinology*, 1986, 119, 1446–1453.
3) Reichert, L. E. and Bhalla, V. K. "Development of a Radioligand Tissue Receptor Assay for Human Follicle-Stimulating Hormone." *Endocrinology* 1974, 94, 483–491.

The results obtained in this standard pharmaceutical test procedure are provided in the table below.

| Example | IC$_{50}$ (μM) |
| --- | --- |
| 30a | 1.6 |
| 30b | 1.2 |
| 30c | 1.6 |
| 30d | 1.5 |
| 30e | 2.5 |
| 30f | 1.9 |
| 30g | 1.6 |
| 30h | 7.3 |
| 30k | 2.0 |
| 30l | 3.9 |
| 30m | 2.2 |

-continued

| Example | IC$_{50}$ (μM) |
| --- | --- |
| 30n | 1.8 |
| 30o | 2.4 |
| 30p | 2.5 |
| 30q | 4.0 |
| 30r | 1.1 |
| 30s | 3.0 |
| 30t | 1.3 |
| 30u | 10 |
| 32a | 3.5 |
| 32b | 3.2 |
| 32c | 6.9 |
| 32d | 12.5 |
| 32e | 4.9 |
| 32f | 2.9 |
| 32g | 5.3 |
| 32i | 3.7 |
| 32k | 7.0 |
| 32l | 4.1 |
| 32m | 4.9 |
| 32n | 4.8 |
| 32o | 1.5 |
| 32p | 15 |
| 32q | 2.4 |
| 33a | 6.9 |
| 33b | 4.5 |
| 33c | 6.2 |
| 33d | 5.2 |
| 33e | 4.3 |
| 33f | 16 |
| 33g | 20 |
| 33h | 23 |
| 34a | 3.8 |
| 34b | 1.6 |
| 35 | 4.1 |
| 36a | 16 |
| 36b | 21 |
| 36c | 5.4 |
| 37a | 2.0 |
| 37b | 2.9 |
| 37c | 6.7 |
| 37d | 4.3 |
| 40a | 6.2 |
| 40b | 5.2 |
| 42 | 6.9 |
| 43a | 2.0 |
| 43b | 17 |
| 43c | 4.5 |
| 43d | 12 |
| 43e | 4.3 |
| 43f | 5.0 |
| 43g | 7.0 |
| 43h | 12 |
| 50a | 34 |
| 50b | 41 |
| 59 | 16 |

In Vitro Bio-test Procedure of Agonists and Antagonists to the FSH Receptor

Objective: This procedure was used to verify in vitro efficacy of compounds found to bind to the FSH receptor in the binding procedure.

Methods: Reagents

Compound Vehicle: Stock compounds were solubilized in an appropriate vehicle preferably PBS/0.1% Bovine Serum Albumin (BSA; Sigma Chemical Co., St. Louis, Mo.). The compounds were subsequently diluted in sterile procedure medium (Optimem (Gibco/BRL, Grand Island, N.Y.)/0.1% BSA) prior to use in the bio-procedure.

Preparation of CHO-3D2 Cells; CHO-3D2 cells were plated into 96-well Nunc tissue culture plates at a density of 30,000 cells/well in DMEM/F12 medium (Gibco/BRL, Grand Island, N.Y.) supplemented with 5% Fetal Bovine Serum (Hyclone, Fetal Clone II), 2 mM L-glutamine and penicillin/streptomycin (100 U/mL). Cells were plated one day prior to performing the bio-procedure.

Procedure: On the day of procedure, the wells were washed two times with 100 ul/well of pre-warmed (37 deg C.) procedure medium. After aspirating the second wash, an additional 100 ul of procedure medium was added to each well and the cells pre-incubated for 30–45 minutes at 37 deg C. In a humidified incubator with 5%CO2/95% air. The cells were then challenged with varying dilutions of the test substance(s) in a 50 ul total incubation volume in procedure medium for 30 minutes at 37 deg C. in the humidified incubator. The challenge was terminated by the addition of 50 ul of 0.2 N HCl to each well. CAMP accumulation in the medium was measured by radioimmunoassay.

Test Groups: In the 96-well format, the plate is organized into 12 columns each containing 8 rows of wells. The plate was split in half to test a single compound in both agonist and antagonist mode on the same plate.

For agonist mode, compounds were tested using 5 different concentrations in a dose-response paradigm using one column as a control (challenge medium alone) in agonist mode.

For antagonist mode, compounds were tested in a dose-response paradigm versus a constant level of purified human FSH (the ED20 (1.85 ng/mL); previously calculated during characterization of the bio-procedure). The 96-well format allowed for the capability to test 4 columns of compound, using one of the remaining columns for negative control (challenge medium alone) and the other remaining column for ampositive control (ED20 of FSH alone).

The doses chosen to test each compound were extrapolated from the initial screening process (receptor binding data). Along with the test compounds, FSH was run in agonist mode using doses ranging from 0.1 ng/mL–1000 ng/mL as a postive control. Cytotoxicity of the compounds were screened by treating cells with the highest concentration of each compound used in the cAMP procedure for 30 minutes followed by washing of the cells 2 times with 100 ul PBS. The cells were then incubated for 5 min at 37 deg C. in the presence of 50 ug/mL Fluorescein diacetate and 20 ug/mL Propidium iodide in 100 ul PBS. The cells were washed two times with 100 ul PBS followed by examination of the cells under a fluorescence microscope using a 490 nm filter. Viable cells stained green throughout, while dead cells had red fluorescent nuclei.

Analysis of Results: cAMP accumulation was expressed as fmol/mL. CAMP accumulation in agonist mode, or the ability of the compound to inhibit hFSH-induced cAMP accumulation in antagonist mode was compared to the appropriate negative and positive controls. Data were analyzed statistically by analysis of variance and significant differences between treatments and control determined by Dunnett's test. In antagonist mode, a Duncan's test was used.

Reference Compounds: Test compounds were compared to the effect of purified or recombinant human FSH. In this paradigm, hFSH induced a dose-dependent increase in cAMP accumulation, with apparent ED80=22.55 ng/mL, ED50=6.03 ng/mL and ED20=1.85 ng/mL, calculated using a four-parameter logistic equation.

The results obtained in this standard pharmacological test procedure are provided below.

| Example | $IC_{50}$ ($\mu$M) |
|---|---|
| 30a | 1.6 |
| 30b | 1.3 |

-continued

| Example | $IC_{50}$ ($\mu$M) |
|---|---|
| 30c | 3.6 |
| 30d | 1.6 |
| 30e | 0.9 |
| 30f | 3.1 |
| 30g | 2.5 |
| 30h | 8.1 |
| 30k | 1.5 |
| 30m | 5.8 |
| 30n | 5.5 |
| 30o | 6.2 |
| 30p | 11 |
| 30q | 12 |
| 30r | 2.0 |
| 30s | 4.4 |
| 30t | 1.4 |
| 32a | 2.3 |
| 32b | 2.6 |
| 32e | 9.0 |
| 32f | 4.2 |
| 32i | 4.9 |
| 32o | 1.0 |
| 33c | 4.5 |
| 33d | 2.6 |
| 33e | 1.5 |
| 33f | 11 |
| 33h | 67 |
| 34a | 3.3 |
| 34b | 1.7 |
| 36c | 9.5 |
| 37a | 2.1 |
| 37b | 1.2 |
| 42 | 2.7 |
| 43a | 8.7 |
| 43b | 28 |
| 43d | 13 |
| 43f | 6.4 |
| 43g | 12 |
| 43h | 12 |

In Vitro Bio-test Procedure of Agonists and Antagonists to the FSH Receptor Using Primary Cultures of Rat Granulosa Objective: This procedure was used as a low-throughput functional screening procedure to study in vitro efficacy of compounds found to be agonists or antagonists of the FSH receptor.

Materials and Methods: Reagents

Compound Vehicle: Stock compounds were solubilized in an appropriate vehicle, preferably PBS (phosphate buffered saline) or DMSO (dimethyl sulfoxide), at a concentration of 0.1 M. The compounds were subsequently diluted in sterile challenge medium [McCoy's 5A medium (Gibco/BRL, Grand Island, N.Y.) supplemented with 5 mg/mL insulin, 5 mg/mL transferrin, 5 ng/mL sodium selenite (ITS, Sigma Chemical Co., St. Louis, Mo.), 146 mg/mL L-glutamine, 100 nM testosterone, 100 nM DES and 100 U/mL penicillin/10 mg/mL streptomycin/250 ng/mL amphotericin B (antibiotic/antimycotic, Gibco) and 0.1% bovine serum albumin (Sigma, St. Louis, Mo.)] prior to use in the procedure. The concentration of vehicle was maintained constant throughout all dilutions.

Preparation of Granulosa Cells: Twenty-four day-old immature female Sprague-Dawley rats (Charles River Laboratories, Wilmington, Mass.) were used as donors for ovarian granulosa cells. The animals were treated by single daily injections of 100 mg/kg diethylstilbestrol (DES) in oil over three days. On the fourth day, animals were sacrificed by CO2 asphyxiation and the ovaries were removed. Ovaries were washed three times in 50 mL of sterile HEPES-buffered saline (HBS, pH 7.4). Granulosa cells were harvested by incubating ovaries in a hypertonic medium consisting of serum-free McCoy*s SA medium (Gibco Life Sciences, Grand Island, N.Y.) supplemented with 5 mg/mL insulin, 5 mg/mL transferrin, 5 ng/mL sodium selenite (ITS, Sigma Chemical Co., St. Louis Mo.), 146 mg/mL L-glutamine, 100 nM testosterone, 100 nM DES and 100 U/mL penicillin/10 mg/mL streptomycin/250 ng/mL amphotericin B (antibiotic/antimycotic, Gibco) containing 0.5 M sucrose and 0.1 mM EGTA. Ovaries were then incubated for 45 min. at 37 C. in a humidified incubator gassed with 95% air/5% CO2. They were washed 3 times with 10 mL isotonic medium (hypertonic medium without sucrose and EGTA) and incubated another 45 min. in isotonic medium at 37 C. Granulosa cells were harvested by squeezing the ovaries between two sterile glass microscope slides. Isolated granulosa cells were then placed in an 50 mL centrifuge tube and washed two times by the addition of 50 mL serum-free McCoy*s 5A medium followed by centrifugation at 700×g for 5 min. After the final spin, the cells were resuspended by gentle trituration in 25 mL serum-free medium, an aliquot counted in a hemocytometer and viability estimated by trypan blue exclusion. Cells were plated into 24-well Nunc tissue culture plates at 200,000 viable cells/well in 250 mL.

Procedure: Following plating of the cells, the plates are incubated at 37 C for 2–4 hours at which time the treatments are added to the cells. Treatments are added to the wells at 2× the desired final concentration in 250 mL/well in isotonic medium containing 0.2% BSA. The cells are incubated at 37 C. for 72 h. At the end of the incubation period, the medium is removed from the wells and tested for estradiol concentration by radioimmunoassay.

Experimental Groups: In the 24-well format, the plate was divided into 6 columns of 4 wells/column. One plate per compound was used to test either agonist or antagonist modes.

In agonist mode, each compound was tested in a dose-response paradigm using 5 different doses of the compound and compared the activity to the 6th column of cells which received vehicle alone.

For antagonist mode, each compound was tested in a dose-response paradigm versus a constant level of purified human FSH (the ED50 0.5 ng/mL; previously calculated during the characterization of the bioprocedure). Four different doses of compound were tested in the antagonist mode. In addition, one column was used for a negative control (vehicle alone) and the other remaining column for a positive control (ED50 of FSH alone).

The doses of compound chosen to test were extrapolated from the initial functional screening process. Along with the plates testing compounds, another plate was run in parallel using a dose-response of FSH (0.01–100 ng/mL) as a positive control.

Analysis of Results: Estradiol was expressed as pg/mL. Estradiol secretion in agonist mode, or the ability of the compound to inhibit FSH-induced estradiol secretion in antagonist, was compared to the appropriate negative and positive controls. Data were analyzed statistically by analysis of variance with Huber weighting of log transformed data. Paired differences were determined using the LSD test Reference Compounds: Test compounds were compared to the effect of purified or recombinant human FSH.

Activity: Compounds which significantly increase estradiol secretion as compared to the negative control in agonist mode or significantly inhibited FSH-induced estradiol secretion in antagonist mode were considered active. EC50: Concentration of the compound that gave half-maximal response in terms of estradiol secretion over negative control (agonist mode only). IC50: Concentration of compound that gave half-maximal inhibition of FSH-induced estradiol secretion (for antagonist mode only).

REFERENCES

Hsueh, A. J., Bicsak, T., Jia, X.-C., Dahl, K. D., Fauser, B. C. J. M., Galway, A. B., Czwkala, N., Pavlou, S., Pakoff, H., Keene, J., Boime, I, "Granulosa Cells as Hormone Targets: The role of Biologically Active Follicle-Stimulating Hormone in Reproduction" Rec. Prog. Horm. Res., 1989, 45, 209–277.

The results obtained in this standard pharmacological test procedure are provided below.

| Example | IC$_{50}$ ($\mu$M) |
|---|---|
| 30a | 1.9 |
| 30b | 1.5 |
| 30c | 3.8 |
| 30d | 2.8 |
| 30e | 1.8 |
| 30f | 8.0 |
| 30g | 2.4 |
| 30k | 3.1 |
| 30m | 6.7 |
| 30q | 1.3 |
| 30r | 1.1 |
| 30s | 1.2 |
| 30t | 1.4 |
| 32f | 2.8 |
| 33d | 10 |
| 33e | 2.1 |
| 34a | 57 |
| 34b | 4.9 |
| 43a | 17 |

Immature Rat Test Procedure

In order to assess the ability of compounds to affect FSH-induced changes in ovarian follicular maturation in vivo, immature rats (18 days of age) are treated twice daily for three days with compound in the presence of a half-maximal dose of purified human FSH. Animals are treated via the i.p. or p.o. routes. On the fourth day following treatment, animals are euthanized and the ovaries, uterus and spleen (the spleen is a control tissue that should not respond to FHS stimulation) collected for wet weight determination. In each experiment animals treated with vehicle alone or FSH alone are used as negative and positive controls, respectively. In this paradigm FSH induces a 2–3-fold increase in ovarian and uterine wet weight but has no effect on the spleen (control tissue).

The results obtained in this standard pharmacological test procedure are provided below.

| Example | Route of Administration | IC$_{50}$ (mg/Kg) ovaries | IC$_{50}$ (mg/Kg) uterus | IC$_{50}$ (mg(Kg) spleen |
|---|---|---|---|---|
| 27z | po | >10 | 10 | no effect |
| 27k | ip | 1.1 | 0.5 | no effect |
| 27k | po | 4.8 | 1.9 | no effect |
| 27m | po | 8.4 | 7.9 | no effect |
| 30b | ip | 8.1 | 1.3 | no effect |
| 30b | po | 23 | 10 | no effect |

Based on the results obtained in the standard pharmacological test procedures, the compounds of this invention were shown to antagonize the binding of hFSH to its receptor, in vitro, and to block cellular functions of FSH, in vitro, including the production of second messenger cAMP and estradiol in ovarian and granulosa cells. Representative compounds of this invention were also shown to inhibit FSH stimulated ovarian and uterine weight gain in immature female rats and ovulation in mature female rats. As such, the compounds of this invention are useful as female and male contraceptive agents.

The compounds of this invention may be administered orally or parenterally, neat or in combination with conventional pharmaceutical carriers. Applicable solid carriers can include one or more substances which may also act as flavoring agents, lubricants, solubilizers, suspending agents, fillers, glidants, compression aids, binders or tablet-disintergrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration. Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form.

Preferably the pharmaceutical composition is in unit dosage form, e.g. as tablets or capsules. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

The therapeutically effective dosage to be used in the treatment of a specific psychosis must be subjectively determined by the attending physician. The variables involved include the specific psychosis or state of anxiety and the size, age and response pattern of the patient. In therapeutic treatment, projected daily dosages of the compounds of this invention are 0.1–500 mg/kg for oral administration.

The following procedures describe the preparation of representative examples of compounds of this invention.

EXAMPLE 1a

4-Methoxy-3-(morpholine-4-sulfonyl)-benzoic Acid p-Anisic acid (25.6 g, 168 mmol) was added neat to stirring chlorosulfonic acid (40 mL). This reaction was heated to 65° C. for 4 hours. The solution was poured very slowly into 500 mL of crushed ice, which was itself placed in a dry-ice/acetone bath to keep it cool. The water suspension that formed was allowed to stir for one hour, and it was then filtered. The solid was suspended in ether/dichloromethane (200 mL of 50/50), and excess morpholine (29 mL, 333 mmol) was added slowly. An immediate reaction occurred, but the reaction was allowed to stir overnight and then filtered and dried to provide the title compound (35 g, 69%). $^1$HNMR (DMSO-$d_6$) $\delta$13.2 (bs, 1H), 8.29 (d, J=2 Hz, 1H), 8.28 (dd, J=9 Hz, 2 Hz, 1H), 7.40 (d, J=9 Hz, 1H), 3.99 (s, 3H), 3.60 (m, 4H), 3.10 (m, 4H). MS (ES-POS): [M–H]=300.

By a procedure analogous to Example 1a, but using a different commercially available amine in place of morpholine, the following compounds in Examples 1b to 1 m were prepared.

EXAMPLE 1b

3-Diethylsulfamoyl-4-methoxy-benzoic Acid

From diethylamine (38%): (+ESI) [M+H]+=288.

EXAMPLE 1c 3-(Azepane-1-sulfonyl)-4-methoxy-benzoic Acid

From cycloheptylamine (32%): (–ESI) [M–H]–=312.

EXAMPLE 1d

4-Methoxy-3-(pyrrolidine-1-sulfonyl)-benzoic Acid

From cyclopentylamine (48%): (–ESI) [M–H]–=284.

EXAMPLE 1e

4-Methoxy-3-(thiomorpholine-4-sulfonyl)-benzoic Acid

From thiomorpholine (43%):(–ESI) [M–H]–=316.

EXAMPLE 1f 3-(4-Acetyl-piperazine-1-sulfonyl)-4-methoxy-benzoic Acid

From 1-acetylpiperazine (228%): (–ESI) [M–H]–=341.

EXAMPLE 1g 3-(4-Formyl-piperazine-1-sulfonyl)-4-methoxy-benzoic Acid

From 1-formylpiperazine (19%): (–ESI) [M–H]–=327.

EXAMPLE 1h

4-Methoxy-3-(piperidine-1-sulfonyl)-benzoic Acid

From piperidine (91%): (–ESI) [M–H]–=298.

EXAMPLE 1i

4-Methoxy-3-(4-methyl-piperazine-1-sulfonyl)-benzoic Acid

From 1-methylpiperizine (81%): (–ESI) [M–H]–=313.

EXAMPLE 1j

4-Methoxy-3-(4-phenyl-piperazine-l-sulfonyl)-benzoic Acid

From 1-phenylpiperazine (86%): (–ESI) [M–H]–=375.

EXAMPLE 1k

4-Methoxy-3-(2-methoxy-ethylsulfamoyl)-benzoic Acid

From 2-methoxyethylamine (20%): (–ESI) [M–H]–=288.

EXAMPLE 1l

4-Methoxy-3-(2-morpholin-4-yl-ethylsulfamoyl)-benzoic Acid

From 4-(2-aminoethyl)morpholine (13%): (+ESI) [M+H]+=345.

EXAMPLE 1m

3-[Bis(2-methoxy-ethyl)-sulfamoyl]-4-methoxy-benzoic Acid

From bis(2-methoxyethyl)amine (60%): (–ESI) [M–H]–=346.

EXAMPLE 2

3-(1 1-Dioxo-1-thiomorpholine-4-sulfonyl)-4-methoxy-benzoic Acid

4-Methoxy-3-(thiomorpholine-4-sulfonyl)-benzoic acid (Example 1e, 0.318 g, 1.00 mmol) was dissolved in 5 mL of glacial acetic acid and cooled to zero degrees in an ice water bath. To the stirring solution was added dropwise hydrogen peroxide (0.41 mL, 4.00 mmol) over a ten minute period. The ice bath was removed and the reaction mixture heated to 100 C. in an oil bath and stirred overnight. The solution was allowed to cool to room temperature and was then concentrated to dryness on a rotary evaporator and placed under high vacuum to dry affording 347 mg (99%) of the title compound as a white solid. $^1$HNMR (DMSO-d$_6$): δ8.31 (d, J=2 Hz, 1H), 8.20 (dd, J=9 Hz, 2 Hz, 1H), 7.39 (d, J=9 Hz, 1H), 4.0 (s, 3H), 3.64 (m, 4H), 3.21 (m, 4H); MS (–ESI): [M–H]–=348; Anal.Calc. for $C_{12}H_{15}NO_7S_2$: C, 41.25; H, 4.33; N, 4.01. Found: C, 41.00; H, 4.01; N, 4.00.

EXAMPLE 3

4-Methylsulfanyl-3-(morpholino-4-sulfonyl)-benzoic Acid

Commercially available p-methylthiobenzoic acid (15 g, 90 mmol) was suspended in chlorosulfonic acid (40 mL), and it slowly went into solution. This solution was allowed to stir at room temperature for 5 h and then added slowly to crushed ice (about 300 mL). The resulting suspension was filtered. This solid sulfonyl chloride intermediate was suspended in ethyl acetate (150 mL), and morpholine (16 g, 184 mmol) was added. This suspension was allowed to stir overnight. It was extracted with 3N HCl three times, and these water washings were discarded. The ethyl acetate was dried with brine and magnesium sulfate. The solvent was removed under vacuum to provide the title compound (15 g, 53%) as a crystalline solid: $^1$HNMR (DMSO-d$_6$) δ13.2–12.8 (bs, 1H), 8.28 (d, J=2 Hz, 1 H), 8.16 (dd, J=9 Hz, 2 Hz, 1H), 7.62(d, J=9 Hz, 1H), 3.62 (m, 4H), 3.19 (m, 4H), 2.60 (s, 3H); MS (ESI-POS):[M+H]+=318; Anal. Calc. for $C_{12}H_{15}NO_5S_2$: C, 45.41; H, 4.76; N, 4.41. Found: C, 44.76; H, 4.57; N, 4.17.

EXAMPLE 4

4-Methanesulfonyl-3-(morphline-4-sulfonyl)-benzoic Acid

4-Methylsulfanyl-3-(morpholino-4-sulfonyl)-benzoic acid (Example 3, 1 g, 3.1 mmol) was dissolved in glacial acetic acid (10 mL) and hydrogen peroxide (3 mL of 30% solution) was added. The reaction mixture was allowed to stir at 60° C. for 72 h under nitrogen. The reaction mixture was partitioned between ethyl acetate and 3N HCl. The ethyl acetate phase was extracted 3 times with HCl (3N) solution to remove acetic acid. The ethyl acetate was dried with brine and magnesium sulfate. The solvent was removed under reduced pressure. The oily crude was triturated with hexane and the solid was filtered to provide the title compound (963 mg, 90%) as a crystalline solid: $^1$HNMR (DMSO-d6) δ14.2–13.6 (bs, 1H), 8.50 (s, 1H ), 8.42 (s, 2H), 3.62 (m, 4H), 3.48 (s, 3H), 3.29 (m, 4H); MS (ESI-NEG):[M–H]–348; Anal. Calc. for $C_{12}H_{15}NO_7S_2$: C, 41.25; H, 4.33; N, 4.01. Found: C, 40.38; H, 4.17; N, 3.83.

EXAMPLE 5

4-Fluoro-3-(morpholine-4-sulfonyl)-benzoic Acid, Methyl Ester

Chlorosulfonic acid (16.63g, 14.274 mmol) was added to commercially available 4-fluorobenzoic acid (2 g, 1.427 mmol) at room temperature under a drying tube packed with calcium sulfate and the reaction mixture was heated at 150° C. for 1.5 hours. The reaction mixture was cooled to 0° C. then poured into ice (50 g). The precipitate was filtered and dried to afford a light brown powder 2.81 g, (82% yield). This powder was dissolved in dichloromethane (100 mL) at 0° C. under $N_2$ and a solution of morpholine (2.25 g, 25.8 mmol) in dichloromethane (25 mL) was added dropwise over a 20 minute period. The resulting yellow solution was allowed to warm to room temperature and stirred 18 hours. Water (50 mL) was added and the reaction mixture was extracted with dichlorormethane (50 mL). The dichloromethane was dried and concentrated to afford a pale white powder 2.73 g (80% yield). This powder was dissolved in DMF (15 mL) at room temperature under $N_2$, potassium carbonate (2.60 g, 18.874 mmol) and iodomethane (2.01 g, 14.156) were added and the reaction mixture was stirred 18 hours. The reaction mixture was added to water and extracted with ethyl acetate. The ethyl acetate was dried and concentrated and the syrup was flash chromatographed (hexane:ethyl acetate/3:1) to afford the title compound as a white powder (2.26 g, 79%): $^1$HNMR (DMSO-d$_6$) δ3.02 (t, J=2.5 Hz, 4H), 3.60 (t, J=2.5 Hz, 4H), 7.61 (dd, J=10, 9 Hz, 1H), 8.24 (dd, J=9, 2.5 Hz, 1H), 8.27 (dt, J=10, 2.5 Hz, 1H), 13.20 (s, 1H): MS (ESI) [M–H]– at m/z 288.

EXAMPLE 6

4-Fluoro-3-(morpholine-4-sulfonyl)-benzoic Acid

A solution of lithium hydroxide (1.56 g, 37.3 mmol) in water (5 mL) was added to a stirred solution of 4-fluoro-3-(morpholine-4-sulfonyl)-benzoic acid, methyl ester (Example 5, 2.26 g, 7.45 mmol) in methanol (50 mL) / water (10 mL) at 0° C. After 4 hours, the clear solution was quenched with aqueous hydrochloric acid (2M, 10 mL).

Concentration in vacuo to remove the methanol afforded a white precipitate. Filtration and drying afforded the title compound as a white powder (1.89 g, 88% yield): $^1$HNMR (CDCl$_3$) δ3.21 (td, J=7, 1.5 Hz, 4H), 3.75 (td, , J=7, 1.5 Hz , 4H), 3.98 (s, 3H), 7.28 (dd, J=18, 15 Hz, 1H), 8.28 (ddd, J=7, 5, 2 Hz, 1H), 8.51 (dd, J=7, 2 Hz, 1H): MS (ESI) [M–H]$^-$ at m/z 303.

EXAMPLE 7a

4-Ethylsulfanyl-3-(morpholine-4-sulfonyl)-benzoic Acid

Sodium hydride (290 mg, 7.3 mmol) was added to a room temperature, stirred solution of 4-fluoro-3-(morpholine-4-sulfonyl)-benzoic acid (Example 6, 600 mg, 2.1 mmol) in DMF (10 mL) under a nitrogen atmosphere. After 20 min, ethanethiol (387 mg, 6.2 mmol) was added and the reaction mixture was heated at 30° C. for 20 hours. After cooling to room temperature and quenching with 2M HCl, the reaction mixture was partitioned between ethyl acetate and water. Further extraction of the aqueous layer with ethyl acetate, combination of all organic layers, drying and concentration provided a white powder (720 mg). This powder was dissolved in DMF (10 mL) at room temperature under N$_2$, potassium carbonate (600 mg, 4.3 mmol) and iodomethane (462 mg, 3.3 mmol) were added and the reaction mixture was stirred 18 hours. The reaction mixture was added to water and extracted with ethyl acetate. The ethyl acetate was dried and concentrated and the syrup was flash chromatographed (hexane:ethyl acetate/3:1) to afford a white powder (490 mg). A solution of lithium hydroxide (119 mg g, 2.8 mmol) in water (2 mL) was added to a stirred solution of this powder (490 mg) in methanol (20 mL)/water (5 mL) at 0° C. After 18 hours at room temperature, the clear solution was quenched with aqueous hydrochloric acid (2M, 10 mL). Concentration in vacuo to remove the methanol afforded a white precipitate. Filtration and drying afforded the title compound as a white powder (460 mg, 84%): $^1$HNMR (DMSO-d$_6$) δ1.32 (t, J=7 Hz, 3H), 3.01 (t, J=3 Hz, 4H), 3.01 (q, J=7 Hz, 2H), 3.55 (t, J=3. Hz, 4), 7.66 (d, J=8 Hz, 1H), 8.05(dd, J=8, 2 Hz, 1H), 8.29 (d, J=2 Hz, 1H), 13.20 (s, 1H): MS (ESI) [M–H]$^-$ at m/z 332.

By a procedure analogous to Example 7a, but using a different commercially available thiol or alcohol in place of ethanethiol, the following compounds in Examples 7b to 7e were prepared.

EXAMPLE 7b

4-Butylsulfanyl-3-(morpholine-4-sulfonyl)-benzoic Acid

From 1-butanethiol (83%): MS (ESI) [M–H]$^-$ at m/z 360.

EXAMPLE 7c

4-Isopropylsulfanyl-3-(morpholine-4-sulfonyl)-benzoic Acid

From 2-propanethiol (99%): MS (ESI) [M–H]$^-$ at m/z 344.

EXAMPLE 7d 4-(Methoxycarbonylmethyl)sulfanyl-3-(morpholine-4-sulfonyl)-benzoic Acid From methyl thioglycoloate (98%): MS (ESI) [M–H]$^-$ at m/z 386.

EXAMPLE 7e 3-(Morpholine-4-sulfonyl)-4-(tetrahydro-furan-2-ylmethoxy)-benzoic Acid From tetrahydrofufuryl alcohol (64%): MS (ESI) [M–H]$^-$ at m/z 370.

EXAMPLE 8a 3-(Morpholine-4-sulfonyl)-4-morpholin-4-yl-benzoic Acid

A solution of 4-fluoro-3-(morpholine-4-sulfonyl)-benzoic acid (Example 6, 500 mg, 1.7 mmol), potassium carbonate (1.20 g, 8.6 mmol) and morpholine (2 g, 22.9 mmol) in DMF (20 mL) was heated at reflux for 20 hours under N$_2$. After cooling to room temperature and quenching with 2M HCl, the reaction mixture was partitioned between ethyl acetate and water. Further extraction of the aqueous layer with ethyl acetate, combination of all organic layers, drying and concentration provided a white powder (500 mg): This powder was dissolved in DMF (10 mL) at room temperature under N$_2$, potassium carbonate (389 mg, 2.8 mmol) and iodomethane (299 mg, 2.1 mmol) were added and the reaction mixture was stirred 18 hours. The reaction mixture was added to water and extracted with ethyl acetate. The ethyl acetate was dried and concentrated and the syrup was flash chromatographed (hexane:ethyl acetate/3:1) to afford a white powder (310 mg). A solution of lithium hydroxide (165 mg, 4.2 mmol) in water (2 mL) was added to a stirred solution of the powder in methanol (20 mL)/water (50 mL) at 0° C. After 20 hours, the clear solution was quenched with aqueous hydrochloric acid (2M, 10 mL). Concentration in vacuo to remove the methanol afforded a white precipitate. Filtration and drying afforded the title compound as a white powder (260 mg, 44%): $^1$HNMR (DMSO-d6) δ2.97 (t, J=4 Hz, 4H), 3.00 (t, J=4 Hz, 4H), 3.57(t, J=4 Hz, 4H), 3.71 (t, J=4 Hz), 7.56 (d, J=8 Hz, 1H), 8.15 (dd, J=8, 2 Hz, 1H), 8.34 (d, J=2 Hz, 1H), 13.20 (s, 1H); MS (ESI) [M–H]$^-$ at m/z 357.

By a procedure analogous to Example 8a, but using a different commercially available amine in place of morpholine, the following compounds in Examples 8b to 8d were prepared.

EXAMPLE 8b

4-Bis(2-methoxyethyl)aminol-3-(morpholine-4-sulfonyl)-benzoic Acid

From bis(2-methoxyethyl)amine (12%): MS (ESI) [M–H]$^-$ at m/z 401.

EXAMPLE 8c

4-Dimethylamino-3-(morpholine-4-sulfonyl)-benzoic Acid

From dimethylamine (39%): MS (ESI) [M–H]$^-$ at m/z 315.

EXAMPLE 8d 4-(2-Methoxyethylamino)-3-(morpholine-4-sulfonyl) benzoic Acid

From 2-methoxyethylamine (55%): MS: (+)APCI [M+H]+ 345.

EXAMPLE 9

4-Mercapto-3-(morpholine-4-sulfonyl)-benzoic Acid

Sodium hydrosulfide monohydrate (237 mg, 4.3 mmol) was added to a solution of 4-fluoro-3-(morpholine-4- sulfonyl)-benzoic acid (Example 6, 350 mg, 1.2 mmol) in DMF (15 mL) and the reaction mixture was heated at 60° C. for 20 hours under $N_2$. After cooling to room temperature and quenching with 2M HCl, the reaction mixture was partitioned between ethyl acetate and water. Further extraction of the aqueous layer with ethyl acetate, combination of all organic layers, drying and concentration provided a white powder (326 mg, 89% yield): $^1$HNMR DMSO-$d_6$) δ2.99 (t, J=4 Hz, 4H), 3.58 (t, J=4. Hz, H), 7.48 (d, J=8 Hz,1H), 7.87 (dd, J=8, 2 Hz, 1H), 8.29 (d, J=2 Hz, 1H), 13.20 (s, 1H): MS (ESI) [M−H]$^-$ m/z 304.

EXAMPLE 10a

4-(2-Methoxyethylsulfanyl)-3-(morpholine-4-sulfonyl)-benzoic Acid

2-Chloroethyl methylether (374 mg, 3.9 mmol) and potassium hydroxide (163 mg, 2.9 mmol) were added to a room temperature, stirred solution of 4-mercapto-3-(morpholine-4-sulfonyl)-benzoic acid (Example 9, 400 mg, 1.3 mmol) in ethyl alcohol (22 mL), water (3 mL) and the reaction mixture was heated at 80° C. for 15 minutes. The reaction mixture was cooled to 0° C. and quenched with 2M HCl (10 mL). The resulting precipitate was filtered to provide a white powder (340 mg). This powder was dissolved in DMF (5 mL) at room temperature under $N_2$, potassium carbonate (260 mg, 1.9 mmol) and iodomethane (200 mg, 1.4 mmol) were added and the reaction mixture was stirred 18 hours. The reaction mixture was added to water and extracted with ethyl acetate. The ethyl acetate was dried and concentrated and the syrup was flash chromatographed (hexane:ethyl acetate/3:1) to afford a yellow syrup (320 mg). A solution of lithium hydroxide (176 mg, 0.9 mmol) in water (2 mL) was added to a stirred solution of this powder in methanol (10 mL)/water (30 mL) at room temperature. After 20 hours, the clear solution was quenched with aqueous hydrochloric acid (2M, 10 mL). Concentration in vacuo to remove the methanol afforded a white precipitate. Filtration and drying afforded the title compound as a white powder (230 mg, 48% yield): $^1$HNMR (DMSO-$d_6$) δ3.09(m, 4H), 3.29 (s, 3H), 3.30 (m, 4H), 3.57 (m, 4H), 7.71 (d, J=8.5 Hz, 1H), 8.05 (dd, J=8.5, 2 Hz, 1H), 8.29 (d, J=2 Hz, 1H), 13.10 (s, 1H): MS (ESI) [M−H]$^-$ at m/z 362.

EXAMPLE 10b

4-[2-(2-Methoxyethoxy)ethylsulfanyl]-3-(morpholine-4-sulfonyl)benzoic Acid

Prepared according to the procedure for Example 10a except using 1-bromo-2-(2-methoxyethoxy)ethane in place of 2-chloroethyl methylether (35%): MS (ESI) [M−H]$^-$ at m/z 404.

EXAMPLE 11

4-Hydroxy-3-(morpholine-4-sulfonyl)-benzoic Acid

4-Fluoro-3-(morpholine-4-sulfonyl)-benzoic acid (Example 6, 5.36 g, 19 mmol) was dissolved in DMF and commercially available 2-methylsulfonyl ethanol (4.8 g, 39 mmol) was added. After five minutes of stirring, sodium hydride (2.4 g of 60% dispersion in mineral oil, 61 mmol) was added. The solution immediately turned black. After 15 min, the reaction was complete. The DMF solution was partitioned between ethyl acetate (150 mL) and brine/HCl (200 mL). The brine solution was discarded, and this was repeated two additional times. All ethyl acetate was dried with magnesium sulfate, and removed under reduced pressure to provide the title compound as a white solid (4.0 g, 74%): $^1$HNMR (DMSO-$d_6$) δ8.23 (d, J=2 Hz, 1H), 8.02 (dd, J=9 Hz, 2 Hz, 1H), 7.09 (d, J=9 Hz, 1H), 3.62 (m, 4H), 3.12 (m, 4H); MS (−APCI):[M−H]$^-$286; Anal.Calc. for $C_{11}H_{13}NO_6S$: C, 44.99; H, 4.56; N, 4.88. Found: C, 45.45; H, 4.41; N, 4.74.

EXAMPLE 12

4-Hydroxy-3-(morpholine-4-sulfonyl)-benzoic Acid, Methyl Ester

The 4-hydroxy-3-(morpholine-4-sulfonyl)-benzoic acid (4.0 g, 14 mmol) was dissolved in methanol and cooled to 0° C. Thionyl chloride (5 mL) was added slowly to the stirring solution. The solution was allowed to stir 15 h under nitrogen at room temperature. Water (10 mL) was added slowly to neutralize the thionyl chloride, and the solvent was removed under reduced vacuum. The concentrated oil was partitioned between ethyl acetate and water, and the ethyl acetate phase was washed with saturated sodium bicarbonate solution twice. The ethyl acetate was washed with brine, and dried using magnesium sulfate. Solvent was removed under vacuum to yield the crude oil. The crude was purified using silica gel (eluent 40% ethyl acetate/hexane) to provide the title compound (3.73 g,86%) as a white solid: $^1$HNMR (DMSO-d6) δ11.8–11.9 (bs, 1H), 8.22 (d, J=2 Hz, 1H), 8.05 (dd, J=9 Hz, 2 Hz, 1H), 7.14 (d, 9 Hz, 1H), 3.84 (m, 3H), 3.62 (m, 4H), 3.11 (m, 4H); MS (EI): M+ 301; Anal.Calc. for $C_{12}H_{15}NO_6S$: C, 47.83; H, 5.02; N, 4.65. Found: C, 47.58; H, 4.95; N, 4.65.

EXAMPLE 13a

4-[2-(2-Methoxyethoxy)ethoxy]-3-(morpholine-4-sulfonyl)-benzoic acid

Triphenylphosphine (2.62 g, 10 mmol) and di(ethylene glycol) methyl ether (1.20 g, 10 mmol) were added to a solution of 4-hydroxy-3-(morpholine-4-sulfonyl)-benzoic acid methyl ester (Example 12, 1.0 g, 3.3 mmol) in toluene (30 mL). Diethylazidodicarboxylate (1.74 g, 10 mmol) was added slowly to the solution, and the yellow solution was stirred overnight under nitrogen. The solvent was removed under vacuum and the crude oil was chromatographed using silica gel (60% ethyl acetate/hexane) to provide a ite solid (1.10 g, 2.7 mmol). This solid was dissolved in methanol (20 mL) and NaOH (2 mL of 5N solution) was added. The solution was stirred under nitrogen at 40° C. for 15 h. The solvent was removed under vacuum and the resulting concentrate was partitioned between water and ethyl acetate. The ethyl acetate phase was discarded. The water phase was acidified with dropwise addition of concentrated HCl. The acidic water was extracted three times with ethyl acetate, and the combined ethyl acetate fractions were dried using brine and magnesium sulfate. The solvent was removed under vacuum to provide the title compound (1.02 g, 96%) as a white solid: $^1$HNMR (DMSO-d6) δ8.28 (d, J=2 Hz, 1H), 8.13 (dd, J=9 Hz, 2 Hz, 1H), 7.38 (d, J=9 Hz, 1H), 4.36 (m, 2H), 3.79 (m, 2H) 3.60 (m, 6H), 3.42 (m, 2H), 3.24 (s, 3H), 3.13 (m, 4H); MS (APCI+):[M+H]+ 390; Anal.Calc. for $C_{16}H_{23}NO_8S$: C, 49.35; H, 5.95; N, 3.60. Found: C, 48.34; H, 5.78; N, 3.49.

By a procedure analogous to Example 13a, but using a different commercially available alcohol in place of di(ethylene glycol) methyl ether, the following compounds in Examples 13b to 13d were prepared.

EXAMPLE 13b 3-(Morpholine-4-sulfonyl)-4-(tetrahydro-4H-pyran-4-yloxy)-benzoic Acid From tetrahydro-4H-pyran-4-ol (73%): MS (−ESI) [M−H]− 370.

EXAMPLE 13c 4-(2-Methoxyethoxy)-3-(morpholine-4-sulfonyl)-benzoic Acid

From 2-methoxyethanol (64%): MS (EI) M+ 345.

EXAMPLE 13d 4-(Furan-2-ylmethoxy)-3-(morpholine-4-sulfonyl)-benzoic Acid

From furfuryl alcohol (47%): MS(ESI-NEG):[M−H]− 366.

EXAMPLE 14

3-Morpholin-4-yl-methyl-benzoic Acid

Commercially available methyl 3-bromomethyl benzoate (5 g, 22 mmole) was dissolved in dichloromethane (20 mL) and morpholine (3.93 mL, 45 mmol) was added. The solution was allowed to stir for 12 h, and filtered. The solvent of the filtrate was removed under reduced pressure. The resulting crude ester was dissolved in methanol, and sodium hydroxide (4.6 mL of 5N solution) was added. The solution was stirred overnight at 40° C. for 12 h. The solvent was partially removed under reduced pressure. The crude was acidified, dichloromethane was added and the solution was cooled in ice. After one hour, it was filtered, to provide the title product (2.3 g, 41%) as the white solid hydrochloride salt: $^1$HNMR (DMSO-$d_6$) δ13.1 (bs, 1H), 11.8 (bs, 1H), 8.14 (s, 1H), 7.92 (m, 2H), 7.65 (t, J=4 Hz, 1H), 4.39 (bs, 2H), 3.91(m, 4H), 3.12 (m, 4H). MS (EI-NEG):[M+]221; Anal.RP-HPLC: 99% purity.

EXAMPLE 15

3-(Morpholine-4-sulfonyl)-benzoic Acid

Commercially available 3-(chlorosulfonyl)benzoic acid (3 g, 13.5 mmol) was suspended in dichloromethane (50 mL). Diisopropylethylamine (5.19 mL, 30 mmol) and morpholine (1.67 mL, 21 mmol) were added slowly. After 2 h, the solvent was removed under reduced pressure. The residue was dissolved in ethyl acetate and washed with 3N HCl three times. The ethyl acetate phase was dried over magnesium sulfate and the solvent was removed under reduced pressure, to provide the title product (2.97 g, 81%) as a white solid. $^1$HNMR (DMSO-$d_6$) δ8.28 (d, J=8 Hz, 1H), 8.20 (s, 1H), 8.01 (d, 8 Hz, 1H), 7.83 (t, J=8 Hz, 1H), 3.91(m, 4H), 3.12 (M, 4H). MS (EI-NEG):[M+] 270.

EXAMPLE 16

4-Methoxyethoxybenzoic Acid

Commercially available 4-hydroxy benzoic acid (10.0 g, 72.4 mmol) and 2-chloroethylmethylether (13.7 g, 144 mmol) wer added to a stirred, room temperature solution of KOH (8.12 g, 144 mmol) in ethanol (90 mL) water (10 mL) and the resulting yellow solution was heated at reflux for 20 hours. The reaction mixture was cooled to room temperature and concentrated to provide a light yellow powder. The reaction mixtur was diluted with water (100 mL) and addtional KOH (5 g, 89 mmol) was added and the reaction mixture was heated at reflux for two hours. The reaction mixture was cooled to 0° C., and neutralized with 2M HCl (100 mL). The precipitate was filtered and the off white powder (15.5 g) was chromatographed (silica gel, elutent 95:5/methylene chloride: methanol) to provide the title compound as a white powder (8.73 g, 54%): $^1$HNMR (CDCl$_3$) δ3.37 (s, 3H), 3.69 (t, J=5 Hz, 2H), 4.16 (t, J=5 Hz, 2H), 6.97 (d, J=9 Hz, 2H), 7.86 (d, J=9 Hz, 2H), 12.52 (s, 1); MS (ESI): [M−H]− at m/z 196.

EXAMPLE 17a

4-Allylthiobenzoic Acid

A solution of commercially available 4-mercaptobenzoic acid (4 g, 26 mmol) in methylene chloride (200 mL) was treated with triethylamine (4 g, 40 mol) at room temperature. The resulting solution was cooled to 0° and treated with allyl bromide (10 g, 83 mmol) in methylene chloride (5 mL) under a nitrogen atmosphere. The mixture was stirred at 0° for 2 hours and at room temperature for additional 18 hours. It was diluted with methylene chloride (500 mL), washed, dried, and evaporated. The crude product was recrystallized from methylene chloride/ether/hexane (1:5:20, 25 mL) to afford 3.5 g (66% yield) of the title compound as a pale solid: $^1$HNMR (DMSO-$d_6$) δ3.74 (d, J=7 Hz, 2H), 5.10 (d, J=11, 17 Hz, 1H), 5.30 (d, J=11, 17 Hz, 1H), 5.85 (m, 1H), 7.39 (d, J=9 Hz, 2H), 7.83 (d, J=9 Hz); MS (ES-Neg): [M−H]− 194; Analytical HPLC: 94% purity.

By a procedure analogous to Example 17a, but using a different commercially available alkylating agent in place of allyl bromide or a different commercially available mercaptobenzoic acid in place of 4-mercaptobenzoic acid, the following compounds in Examples 17b to 17d were prepared.

EXAMPLE 17b

4-[(Methoxycarbonyl)methylthiolbenzoic Acid

From methyl bromoacetate and 4-mercaptobenzoic acid (49%): MS (ES-Neg): [M−H]− 225.

EXAMPLE 17c 4-(3-Methoxycarbonyl-2-propenyl)thiobenzoic Acid

From methyl bromocrotonate and 4-mercaptobenzoic acid (22%): MS (ES-Neg): [M−H]− 251.

EXAMPLE 17d

3-[(Methoxycarbonyl)methylthio]benzoic Acid

From methyl bromoacetate and 3-mercaptobenzoic acid (30%): MS (ES-Neg): [M−H]− 225.

EXAMPLE 18a

4-Allylsulfonyl-benzoic Acid

A solution of 4-allylthiobenzoic acid (Example 17a, 730 mg) in methanol (50 mL) was treated with oxone (5 g) in water 50 mL at 0°. The resulting white suspension was stirred at room temperature for 48 hours. The methanol was evaporated and the residue was diluted with water and extracted with methylene chloride. The methylene chloride extract was washed, dried and evaporated to give 626 mg (77% yield) of the title compound as a white solid: $^1$HNMR (DMSO-$_6$) δ4.20 (d, J=7 Hz, 2H, —SO$_2$—CH$_2$), 5.20 (d, J=17, 11 Hz, 1H), 5.30 (d, J=17, 11 Hz, 1H), 5.68 (m, 1H), 7.97 (d, J=9 Hz), 8.10 (d, J=9 Hz); Analytical HPLC: 92.4% pure; MS (ES-Neg): [M–H]$^-$ 225.

By a procedure analogous to Example 18a, but using a different thioether in place of 4-allylthiobenzoic acid, the following compounds in Examples 18b to 18f were prepared.

EXAMPLE 18b

4-[(Methoxycarbonyl)methanesulfonyl]benzoic Acid

From 4-[(Methoxycarbonyl)methylthio]benzoic acid, Example 17b (82%): MS (ES-Neg): [M–H]$^-$ 257.

EXAMPLE 18c 4-(3-Methoxycarbonyl-2-propenyl)sulfonyl-benzoic Acid

From 4-(3-methoxycarbonyl-2-propenyl)thiobenzoic acid, Example 17c (79%): MS (ES-Neg): [M–H]$^-$ 283.

EXAMPLE 18d

3-[(Methoxycarbonyl)methanesulfonyl]benzoic Acid

From 3-[(methoxycarbonyl)methylthio]benzoic acid Example 17d (99%): MS (ES-Neg): [M–H]$^-$ 257.

EXAMPLE 18e

4-Ethylsulfonylbenzoic Acid

From commercially available 4-ethylthiobenzoic acid (51%): MS (ESI) [M–H]$^-$ at m/z 213.

EXAMPLE 18f

5-Methyl-sulfonyl-2-thiophenecarboxylic Acid

From commercially available 5-methylthio-2-thiophenecarboxylic acid (42%): MS (ESI) [M–H]$^-$ at m/z 205.

EXAMPLE 19

4-Methanesulfonylmethylbenzoic Acid

A solution of commercially available methyl 4-(methanesulphonylmethyl)benzoate (1.00 g, 4.4 mmol) in 2M NaOH (25 mL) was heated at reflux for 30 minutes under N$_2$. The reaction mixture was cooled to 0° C. and acidified with 2M HCl (15 mL) to a pH below 2. The white precipitate was filtered and dried to provide the title compound as a white solid (0.95 g, 97% yield): $^1$HNMR (DMSO-d$_6$) δ2.97 (s, 3H), 4.61 (s, 2H), 7.49 (d, J=0.5 Hz, 2H), 7.94–7.98 (d, J=0.5 Hz, 2H), 13.00 (s, 1H): MS (ESI) [M–H]$^-$ at m/z 213.

EXAMPLE 20

2.2'-[(E)-1,2-Ethenediyl]bis(5-{[(9H-fluoren-9-ylmethoxy)carbonyl]amino}benzenesulfonic Acid)

To a solution of commercially available 4,4'-diaminostilbene-2,2'-disulfonic acid (10 g, 27.0 mmol) in a mixture of 270 mL water and 30 mL dioxane was added 14.3 g (135 mmol) of sodium carbonate and the solution stirred until homogeneous. At this time 9-fluorenylmethyl chloroformate was added and the mixture allowed to stir overnight. The solution was filtered and the solids washed with water (200 mL). The collected solids were then suspended in 600 mL of water and 50 mL conc hydrochloric acid added. After 30 minutes the solution was filtered and the solids dried in a vacuum oven overnight at 50° C. to provide the title compound 21.8 g (72%) as a orange-brown solid. MS (ES-NEG): [M–H] 813.

EXAMPLE 21

2,2'-[(E)-1,2-Ethenediyl]bis(5-{[((9H)-fluorene-9-ylmethoxy)carbonyl]amino}benzenesulfonic Acid), Bis(1-methylethyl) Ester 2,2'-[(E)-1,2-Ethenediyl]bis(5-{[(9H-fluoren-9-ylmethoxy)carbonyl]amino}benzenesulfonic acid) (Example 20, 21.8 g, 26.75 mmol) was suspended in 270 mL dioxane and a reflux condensor was attached to the flask. Triisopropylorthoformate (17.88 mL, 80.26 mmol) was added and the mixture heated to reflux. After complete conversion by TLC the mixture was cooled to room temperature and the solids collected by filtration to provide 18 g (75%) of the title compound as an off-white solid: $^1$HNMR (DMSO-d$_6$) δ10.25 (s, 2H), 8.28 (s, 2H), 7.92(d, J=7 Hz, 4H), 7.77 (d, J=7 Hz, 8H), 7.60 (s, 2H), 7.44 (t, J=7 Hz, 4H), 7.37 (t, J=7 Hz, 4H), 4.5–4.7 (m, 6H), 4.34 (m, 2H), 1.18 (d, J=6 Hz, 12H); MS (ES-POS): [M+Na] 921; Anal. Calc. for C$_{50}$H$_{46}$N$_2$O$_{10}$S$_2$0.5H$_2$O: C, 66.13; H, 5.22; N, 3.08. Found: C, 66.00; H, 5.08; N, 3.04.

EXAMPLE 22

2,2'-[(E)-1,2-Ethenediyl]bis[5-aminobenzenesulfonic Acid], Bis(1-methylethyl) Ester 2,2'-[(E)-1,2-Ethenediyl]bis(5-{[((9H)-fluorene-9-ylmethoxy)carbonyl]amino}benzenesulfonic acid), bis(1-methylethyl) ester (Example 21, 18.7 g, 20.89 mmol) was dissolved in 200 mL of dry DMF under a nitrogen atmosphere. The clear solution was cooled to 0° C. in an ice bath and piperidine (8.3 mL, 83.56 mmol) added in one portion. The solution was allowed to gradually warm to room temperature and after 3 hours was diluted with 750 mL ethyl acetate. The mixture was washed with brine (3x). The aqueous layer was then back extracted with ethyl acetate (2x) and the organic layers combined. The organic layer was dried (MgSO$_4$) and concentrated to a small volume on a rotary evaporator. Hexane (200 mL) was added with stirring and the precipitate collected by filtration. Drying under vacuum overnight gave 7.3 g (77%) of the title compound as a dark yellow solid: $^1$HNMR (DMSO-$_6$) δ7.48 (d, J=8 Hz, 2H), 7.38 (s, 2H), 7.20 (d, J=2 Hz, 2H), 6.90 (dd, J=2 Hz, 8 Hz, 2H), 5.90 (br s, 4H), 4.53 (m, 2H), 1.17 (d, J=6 Hz); MS (ES-NEG): [M–H] 453; Anal. Calc. for C$_{20}$H$_{26}$N$_2$O$_6$S$_2$.1.2H$_2$O: C, 50.45; H, 6.01; N, 5.88. Found: C, 50.44; H, 5.83; N, 5.87.

EXAMPLE 23

2,2'-(1,2-Ethanediyl)bis[5-aminobenzenesulfonic Acid], Bis(1-methylethyl) Ester 2,2'-[(E)-1,2-Ethenediyl]bis[5-aminobenzenesulfonic acid], bis(1-methylethyl) ester (Example 22, 500 mg, 1.1 mmol) was dissolved in dry tetrahydrofuran (30 mL) under a nitrogen atmosphere. Palladium on carbon (10%, 117 mg, 0.11 mmol) was added and the flask filled with hydrogen and stirred overnight. The mixture was purged with nitrogen, filtered thru Celite and concentrated to dryness on a rotary evaporator. The crude product was purified by flash column chromatography using 40% ethyl acetate in hexanes as the eluant to afford 430 mg (85%) of the title compound as a white solid: $_1$HNMR (DMSO-d$_6$) δ7.19 (d, J=2 Hz, 2H), 7.13 (d, J=8 Hz, 2H), 6.85 (dd, J=2 Hz,8 Hz, 2H), 4.56 (m, 2H), 2.98 (s, 4H), 1.18 (d, J=8 Hz, 6H); MS (ESI-POS): [M+NH$_4$] 474.

EXAMPLE 24

2-Methyl-5-nitro-benzenesulfonic Acid, 2.2-Dimethylpropyl Ester

Neopentyl alcohol (0.75 g, 8.50 mmol) was added to a solution of commercially available 2-methyl-5-nitro-benzenesulfonyl chloride (1.00 g, 4.20 mmol), pyridine (1.72 mL, 21.2 mmol and anhydrous dioxane (40 mL). A water cooled condenser was attached and the material was heated to reflux. After stirring for two days the mixture was cooled to room temperature and diluted with ethyl acetate (350 mL). The organic layer was washed with water, then 1 N HCl solution, and finally brine. After drying with MgSO4 the solution was concentrated to afford 690 mg of the title compound as a yellow solid.(55%): $^1$HNMR (DMSO-$_6$) δ8.57 (d, J=2 Hz, 1H), 8.51 (dd, J=8 Hz, 2 Hz, 1H), 7.85 (d, J=8 Hz, 1H), 3.78 (s, 2H), 2.70 (s, 3H), 0.88 (s, 9H); MS (EI): [M+] 287; Anal. Calc. for $C_{12}H_{17}NO_5S$: C, 50.16; H, 5.96; N, 4.88. Found: C, 49.83; H, 5.69; N, 4.90.

EXAMPLE 25

2,2'-[(E)-1.2-Ethenediyl]bis[5-nitrobenzenesulfonic Acid], Bis(2,2-dimethylpropyl) Ester 2-Methyl-5-nitro-benzenesulfonic acid, 2,2-dimethylpropyl ester (Example 24, 8.00 g, 28 mmol) was dissolved in DMF (100 mL) under a nitrogen atmosphere. Potassium t-butoxide (9.41 g, 84 mmol) was added and reaction mixture immediately turned dark blue. The reaction mixture was allowed to stir for 15 h. The DMF was removed under reduced pressure and the solid was partitioned between ethyl acetate and water. Solid material that was not dissolved was filtered off. The ethyl acetate washing was saved and washed two additional times with water. The ethyl acetate solution was dried over magnesium sulfate and the solvent was removed under reduced pressure. This residue was triturated in dichloromethane/hexane to provide 5.13 g of the title compound (64%) as a white solid: $^1$HNMR (DMSO-$_6$) δ8.74 (dd, J=8 Hz, 2 Hz, 2H), 8.65 (d, J=2 Hz, 2H), 8.16 (d, J=8 Hz, 2H), 7.96 (s, 2H), 3.81 (s, 4H), 0.81 (s, 18H); Anal. Calc. for $C_{24}H_{30}N_2O_{10}S_2$: C, 50.52; H, 5.30; N, 4.91. Found: C, 50.52; H, 5.30; N, 5.46.

EXAMPLE 26

2,2'-[(E)-1,2-Ethenediyl]bis[5-aminobenzenesulfonic Acid], Bis(2,2-dimethylpropyl) Ester 2,2'-[(E)-1,2-Ethenediyl]bis[5-nitrobenzenesulfonic acid], bis(2,2-dimethylpropyl) ester (Example 25, 2.0 g, 3.5 mmol) was suspended in ethyl acetate (100 mL) and tin chloride dihydrate (7.9 g, 35 mmol) was added. The mixture was heated to 70° C. under a nitrogen atmosphere for 15 h. The solvent was removed under reduced pressure and the residue was partitioned between ethyl acetate and saturated sodium carbonate solution. The solid tin carbonate was filtered and the ethyl acetate phase was washed two additional times with water and dried over magnesium sulfate. The solvent was removed under reduced pressure to provide 1.2 g of the title compound (66%) as a white solid: $^1$HNMR (DMSO-d$_6$) δ7.51 (d, J=8 Hz, 2H), 7.43 (s, 2H), 7.17(d, J=2 Hz, 2H), 6.90 (dd, J=8 Hz, 2 Hz, 2H), 5.90 (bs, 4H) 3.60 (s, 4H), 0.81 (s, 18H); MS (+ESI): [M$^{30}$ NH4]$^+$ 528; Anal. Calc. for $C_{24}H_{34}N_2O_{10}S_2$ (0.6 eq Sn): C, 49.52; H, 5.88; N, 4.81. Found: C, 48.82; H, 5.75; N, 4.6.

EXAMPLE 27a

2,2'-[(E)-1,2Ethenediyl]bis[5-[[4-(methylsulfonyl) benzoyl]amino]benzenesulfonic Acid], Bis(1-methylethyl) Ester To a solution of commercially available 4-(methylsulfonyl)-benzoic acid (0.264 g, 1.32 mmol) in 65 mL of dry tetrahydrofuran under nitrogen was added dimethylformamide (50 μL) and the solution was cooled to zero degrees in an ice water bath. Oxalyl chloride (0.127 mL, 1.45 mmol) was added and the mixture stirred for 30 minutes and then allowed to warm to room temperature. After 3 hours, the mixture was concentrated to dryness and then redissolved in 50 mL of dry tetrahydrofuran. This solution was added dropwise over a five hour period to a stirred suspension of bis(1-methylethyl) 2,2'-[(E)-1,2-ethenediyl]bis[5-aminobenzenesulfonate] (Example 22, 0.60 g, 1.32 mmol) and potassium carbonate (0.365 g, 2.64 mmol) in 65 mL of dry THF. The resulting mixture was stirred overnight. The reaction mixture was concentrated to near dryness on a rotary evaporator and then diluted with ethyl acetate (300 mL) and water (100 mL). A precipitate was present at the interface between the aqueous and organic layers. The solution was filtered and the solid collected. The solid was pumped dry under vacuum overnight to afford 190 mg (35%).of the title compound as a yellow solid: $^1$HNMR (DMSO-d$_6$) δ11.06 (s, 2H), 8.66 (d, J=2 Hz, 2H), 8.24 (m, 6H), 8.13 (d, J=8 Hz, 4H), 7.92 (d, J=9 Hz, 2H), 7.73 (s, 2H), 4.68 (m, 2H), 3.34 (s, 6H), 1.20 (m, 12H).

By a procedure analogous to Example 27a, but using a different benzoic acid in place of 4-(methylsulfonyl)-benzoic acid and/or a different 5-aminobenzenesulfonate in place of 2,2'-[(E)-1,2-ethenediyl]bis[5-aminobenzenesulfonic acid], bis(1-methylethyl) ester, the following compounds in Examples 27b to 27w were prepared.

EXAMPLE 27b

2,2'-[(E)-1,2-Ethenediyl]bis[5-[[4-(2-(2-methoxyethoxy)ethoxy)-3-(4-morpholinosulfonyl) benzoyl]amino]benzenesulfonic Acid], Bis(1-methylethyl) Ester From 4-[2-(2-methoxyethoxy)ethoxy]-3-(morpholine-4-sulfonyl)-benzoic acid, Example 13a and 2,2'-[(E)-1,2-ethenediyl]bis[5-aminobenzenesulfonic acid], bis(1-methylethyl) ester, Example 22 (50%): +ESI: [M+NH$_4$]+ 1214.

EXAMPLE 27c

2,2'-[(E)-1,2-Ethenediyl]bis[5-[[3-[(1,1-dioxido-4-thiomorpholinyl)sulfonyl]-4-methoxybenzoyl] amino]benzenesulfonic Acid], Bis(1-methylethyl) Ester From 3-(1,1-dioxo-1-thiomorpholine-4-sulfonyl)-4-methoxy-benzoic acid, Example 2 and 2,2'-[(E)-1,2- ethenediyl]bis[5-aminobenzenesulfonic acid], bis(1-methylethyl) ester, Example 22 (75%): –ESI: [M–H]– 1115.

EXAMPLE 27d 2,2'-[(E)-1,2-Ethenediyl]bis[5-[[4-methoxy-3-[(4-phenyl-1-piperazinyl)sulfonyl]benzoyl]amino] benzenesulfonic Acid], Bis(1-methylethyl) Ester From 4-methoxy-3-(4-phenyl-piperazine-1-sulfonyl)-benzoic acid, Example 1j and 2,2'-[(E)-1,2-ethenediyl]bis[5-aminobenzenesulfonic acid], bis(1-methylethyl) ester, Example 22 (24%): +ESI: [M+H]+1171.

EXAMPLE 27e 2,2'-[(E)-1,2-ethenediyl]bis[5-[[4-methoxy-3-[(4-methyl-1-piperazinyl)sulfonyl]benzoyl]amino] benzenesulfonic Acid], Bis(1-methylethyl) Ester From 4-methoxy-3-(4-methyl-piperazine-1-sulfonyl)-benzoic acid, Example 1i and 2,2'-[(E)-1,2-ethenediyl]bis[5-aminobenzenesulfonic acid], bis(1-methylethyl) ester, Example 22 (43%): –ESI: [M–H]– 1045.

EXAMPLE 27f 2,2'-(E)-1,2-Ethenediyl]bis[5-[[4-methoxy-3-(1-piperidinylsulfonyl)benzoyl]amino]benzenesulfonic Acid], Bis(1-methylethyl) Ester From 4-methoxy-3-(piperidine-1-sulfonyl)-benzoic acid, Example 1h and 2,2'-[(E)-1,2-ethenediyl]bis[5-aminobenzenesulfonic acid], bis(1-methylethyl) ester, Example 22 (69%): –ESI: [M–H]– 1015.

EXAMPLE 27g 2,2'-[(E)-1,2-Ethenediyl]bis[5-[[4-[(2-methoxyethyl)amino]-3-(4-morpholinylsulfonyl)benzoyl]amino] benzenesulfonic Acid], Bis(1-methylethyl) Ester From 4-(2-methoxyethylamino)-3-(morpholine-4-sulfonyl)benzoic acid, Example 8d and 2,2'-[(E)-1,2-ethenediyl]bis[5-aminobenzenesulfonic acid], bis(1-methylethyl) ester, Example 22 (13%): FI-POS: [M+Na] 1129.

EXAMPLE 27h 2,2'-[(E)-1,2-Ethenediyl]bis[5-[[4-methoxy-3-[[(2-methoxyethyl)amino]sulfonyl]benzoyl]amino] benzenesulfonic Acid], Bis(1-methylethyl) Ester From 4-methoxy-3-(2-methoxy-ethylsulfamoyl)-benzoic acid, Example 1k and 2,2'-[(E)-1,2-ethenediyl]bis[5-aminobenzenesulfonic acid], bis(1-methylethyl) ester, Example 22 (85%): +ESI: [M+NH$_4$]+ 1014.

EXAMPLE 27i 2,2'-[(E)-1,2-Ethenediyl]bis[5-[[4-methoxy-3-[[[2-(4-morpholinyl)ethyl]amino]sulfonyl]benzoyl] amino]benzenesulfonic Acid], Bis(1-methylethyl) Ester From 4-methoxy-3-(2-morpholin-4-yl-ethylsulfamoyl)-benzoic acid, Example 11 and 2,2'-[(E)-1,2-ethenediyl]bis[5-aminobenzenesulfonic acid], bis(1-methylethyl) ester, Example 22 (50%): +ESI: [M+H]+ 1108.

EXAMPLE 27j 2,2'-[(E)-1,2-Ethenediyl]bis[5-[[3-(4-morpholinylsulfonyl)-4-[(tetrahydro-2H-pyran-4-yl)oxy]benzoyl]amino]benzenesulfonic Acid], Bis(1-methylethyl) Ester From 3-(morpholine-4-sulfonyl)-4-(tetrahydro-4H-pyran-4-yloxy)-benzoic acid, Example 13b and 2,2'-[(E)-1,2-ethenediyl]bis[5-aminobenzenesulfonic acid], bis(1-methylethyl) ester, Example 22 (51%): $^1$HNMR (DMSO-d$_6$) δ10.94 (s, 2H), 8.60 (d, J=2 Hz, 2H), 8.43 (d, J=2 Hz, 2H,), 8.28 (m, 4H), 8.26 (d, J=2 Hz, 2H), 8.10 (dd, J=8 Hz, 2 Hz, 2H), 7.93 (d, J=9 Hz, 2H), 7.65 (m, 4H), 4.65 (m, 2H), 3.60 (m, 8H), 3.18 (s, 6H), 3.12 (m, 8H), 1.18 (d, J=6 Hz, 12H).

EXAMPLE 27k 2,2'-[(E)-1,2-Ethenediyl]bis[5-[[4-(methylthio)-3-(4-morpholinylsulfonyl)benzoyl]amino] benzenesulfonic Acid], Bis(1-methylethyl) Ester From 4-methylsulfanyl-3-(morpholino-4-sulfonyl)-benzoic acid, Example 3 and 2,2'-[(E)-1,2-ethenediyl]bis[5-aminobenzenesulfonic acid], bis(1-methylethyl) ester, Example 22 (42%): $^1$HNMR (DMSO-d$_6$) δ10.87 (s, 2H), 8.54 (s, 2H,), 8.47 (s, 2H,), 8.24 (m, 4H), 7.92 (d, J=2 Hz, 2H), 7.82 (s, 2H), 7.73 (d, J=9 Hz, 2H), 4.95 (m, 2H), 4.78 (m, 2H), 3.89 (m, 4H), 3.60 (m, 8H), 3.58 (m, 4H), 3.12 (m, 8H), 1.97 (m, 4H), 1.68 (m, 4H), 1.18 (d, J=6 Hz, 12H).

EXAMPLE 27l 2,2'-[(E)-1,2-Ethenediyl]bis[5-[[3-[[bis(2-methoxyethyl)amino]sulfonyl]-4-methoxy benzoyl] amino]benzenesulfonic Acid], Bis(1-methylethyl) Ester From 3-[bis(2-methoxy-ethyl)-sulfamoyl]-4-methoxy-benzoic acid, Example 1m and 2,2'-[(E)-1,2-ethenediyl]bis[5-aminobenzenesulfonic acid], bis(1-methylethyl) ester, Example 22 (36%): +ESI: [M+NH$_4$]+ 1130.

EXAMPLE 27m 2,2'-[(E)-1,2-Ethenediyl]bis[5-[[(4-methylsulfonyl)-3-(nitro)-benzoyl]amino]benzenesulfonic Acid], Bis(1-methylethyl) Ester From commercially available 4-methylsulfonyl-3-nitro-benzoic acid and 2,2'-[(E)-1,2-ethenediyl]bis[5-aminobenzenesulfonic acid], bis(1-methylethyl) ester, Example 22 (41%): MS: –ESI [M–H]– 907.

EXAMPLE 27n 2,2'-(1,2-Ethanediyl)bis[5-[[4-methoxy-3-(4-morpholinylsulfonyl)benzoyl]amino] benzenesulfonic Acid], Bis(1-methylethyl) Ester From 4-methoxy-3-(morpholine-4-sulfonyl)-benzoic acid, Example 1a and 2,2'-(1,2-ethanediyl)bis[5-aminobenzenesulfonic acid], bis(1-methylethyl) ester, Example 23 (35%): MS (ESI+): [M+H]+ 1023.

EXAMPLE 27o 2,2'-[(E)-1,2-Ethenediyl]bis[5-[[4-(methylthio)-3-(4-morpholinylsulfonyl)benzoyl]amino] benzenesulfonic Acid], Bis(2,2-dimethylpropyl) Ester From 4-methylsulfanyl-3-(morpholino-4-sulfonyl)-benzoic acid, Example 3, and 2,2'-[(E)-1,2-ethenediyl]bis[5-aminobenzenesulfonic acid], bis(2,2-dimethylpropyl) ester, Example 26 (49%): MS (–ESI):[M–H]–1107.

EXAMPLE 27p 2,2'-[(E)-1,2-Ethenediyl]bis[5-[[3-(4-morpholinylsulfonyl)-4-[(tetrahydro-2H-pyran-4-yl)oxy]benzoyl]amino]benzenesulfonic Acid], Bis(2,2-dimethylpropyl) Ester From 3-(morpholine-4-sulfonyl)-4-(tetrahydro-4H-pyran-4-yloxy)-benzoic acid, Example 13b and 2,2'-[(E)-1, 2-ethenediyl]bis[5-aminobenzenesulfonic acid], bis(2,2-dimethylpropyl) ester, Example 26 (15%): MS (−ESI):[M−H]−1215.

EXAMPLE 27q 2,2'-[(E)-1,2-Ethenediyl]bis[5-[[3-[(1,1-dioxido-4-thiomorpholinyl)sulfonyl]-4-methoxybenzoyl]amino]benzenesulfonic Acid], (2,2-dimethylpropyl) Ester From 3-(1,1-dioxo-1-thiomorpholine-4-sulfonyl)-4-methoxy-benzoic acid, Example 2 and 2,2'-[(E)-1,2-ethenediyl]bis[5-aminobenzenesulfonic acid], bis(2,2-dimethylpropyl) ester, Example 26 (52%): MS (−ESI):[M−H]−1171.

EXAMPLE 27r 2,2'-[(E)-1,2-Ethenediyl]bis[5-[[4-methylsulfonyl)-3-nitrobenzoyl]amino]benzenesulfonic Acid], Bis(2,2-dimethylpropyl) Ester From commercially available 4-methylsulfonyl-3-nitrobenzoic acid and 2,2'-[(E)-1,2-ethenediyl]bis[5-aminobenzenesulfonic acid], bis(2,2-dimethylpropyl) ester, Example 26 (38%): MS (−ESI):[M−H]−963.

EXAMPLE 27s 2,2'-[(E)-1,2-Ethenediyl]bis[5-[[4-methylsulfonyl)-3-(4-morpholosulfinyl)benzoyl]amino]benzenesulfonic Acid], Bis(2,2-dimethylpropyl) Ester From 4-methanesulfonyl-3-(morphline-4-sulfonyl)-benzoic acid, Example 4 and 2,2'-[(E)-1,2-ethenediyl]bis[5-aminobenzenesulfonic acid], bis(2,2-dimethylpropyl) ester, Example 26 (26%): MS (−ESI):[M−H]−1171.

EXAMPLE 27t 2,2'-[(E)-1,2-Ethenediyl]bis[5-[[4-(2-(2-methoxyethoxy)ethylsulfanyl)-3-(4-morpholosulfinyl)benzoyl]amino]benzenesulfonic Acid], Bis(2,2-dimethylpropyl) Ester From 4-[2-(2-methoxyethoxy)ethylsulfanyl]-3-(morpholine-4-sulfonyl)benzoic Acid, Example 10b and 2,2'-[(E)-1,2-ethenediyl]bis[5-aminobenzenesulfonic acid], bis(2,2-dimethylpropyl) ester, Example 26 (91%): MS (−ESI) [M−H]⁻ 1283.

EXAMPLE 27u 2,2'-[(E)-1,2-Ethenediyl]bis[[[4-[(methoxycarbonyl)methylsulfonyl]benzoyl]amino]benzenesulfonic Acid], Bis(2,2-dimethylpropyl) Ester From 4-[(methoxycarbonyl)methanesulfonyl]benzoic Acid, Example 18b and 2,2'-[(E)-1,2-ethenediyl]bis[5-aminobenzenesulfonic acid], bis(2,2-dimethylpropyl) ester, Example 26 (91%): MS (ES-Neg): [M−H]⁻ 989.

EXAMPLE 27v 2,2'-[(E)-1,2-Ethenediyl]bis[5-[[4-(methylsulfonyl)-3-(4-morpholinylsulfonyl)benzoyl]amino]benzenesulfonic Acid], Bis(1-methylethyl) Ester From 4-methanesulfonyl-3-(morphline-4-sulfonyl)-benzoic acid, Example 4 and 2,2'-(1,2-ethanediyl)bis[5-aminobenzenesulfonic acid], bis(1-methylethyl) ester, Example 23 (82%): $^1$HNMR (DMSO-$d_6$) δ11.21 (s, 2H), 8.63 (d, J=2 Hz, 2H), 8.52 (m, 4H), 8.42 (d, J=9 Hz, 2H), 8.28 (dd, J=9 Hz, 2 Hz, 2H), 7.94 (d, J=9 Hz, 2H), 7.87 (s, 2H), 4.64 (m, 2H), 3.66 (m, 8H), 3.41 (s, 6H) 3.26 (m, 8H), 1.58 (d, J=8 Hz, 12H).

EXAMPLE 27w 2,2'-[(E)-1,2-Ethenediyl]bis[5-[[4-methoxy-3-(4-morpholinylsulfonyl)benzoyl]amino]benzenesulfonic Acid], Bis(1-methylethyl) Ester From 4-methoxy-3-(morpholine-4-sulfonyl)-benzoic acid, Example 1a and 2,2'-(1,2-ethanediyl)bis[5-aminobenzenesulfonic acid], bis(1-methylethyl) ester, Example 23 (84%): ES(NEG) [M−H]− 1019.

EXAMPLE 27x 2,2'-[(E)-1,2-Ethenediyl]bis[5-[[4-(2-methoxyethoxy)-3-(4-morpholinylsulfony)benzoyl]amino]benzenesulfonic Acid], Bis(1-methylethyl) Ester From 4-(2-methoxy-ethoxy)-3-(morpholine-4-sulfonyl)-benzoic acid, Example 13c (26%): $^1$HNMR (DMSO-$d_6$) δ10.83 (s, 2H), 8.58 (d, J=2 Hz, 2H), 8.43 (d, J=2 Hz, 2H), 8.32 (m, 4H), 7.88 (d, J=8 Hz, 2H), 7.70 (s, 2H) , 7.46 (d, J=8 Hz, 2H), 4.63(m, 2H), 4.37 (m, 4H), 3.73 (m, 4H), 3.58 (m, 8H), 3.31 (s, 6H), 3.14 (m, 8H), 1.21 (d, J=6 Hz, 12H).

EXAMPLE 27y 2,2'-[(E)-1,2-Ethenediyl]bis[5-[[4-(2-furanylmethoxy)-3-(4-morpholinylsulfony)benzoyl]amino]benzenesulfonic acid], Bis(1-methylethyl) Ester From 4-(furan-2-yl-methoxy)-3-(morpholine-4-sulfonyl)-benzoic acid, Example 13d (27%): $^1$HNMR (DMSO-$d_6$) δ10.84 (s, 2H), 8.57 (d, J=2 Hz, 2H), 8.43 (d, J=2 Hz, 2H), 8.33 (dd, J=9 Hz, 2 Hz, 2H), 8.27 (dd, J=9 Hz, 2 Hz, 2H), 7.89 (m, 4H), 7.72 (m, 4H), 7.61(d, J=9 Hz, 2H), 6.62 (m, 2H), 5.25 (4H, s), 4.67 (m, 2H), 3.57 (m, 8H), 3.08 (m, 8H), 1.21(d, J=6 Hz, 12H).

EXAMPLE 27z 2,2'-[(E)-1,2-Ethenediyl]bis[5-[[4-(ethylsulfonyl)benzoyl]amino]benzenesulfonic acid], Bis(1-methylethyl) Ester (WAY-162489)

From 4-ethylsulfonylbenzoic acid, Example 18e (88%): ES(NEG) [M−H]− 845.

EXAMPLE 28a

5-[[4-(Methylsulfonyl)-3-nitrobenzoyl]amino]-2-[(E)-2-[4-amino-2-sulfophenyl]ethenyl]benzenesulfonic Acid, Bis(1-methylethyl) Ester To a solution of commercially available 4-methylsulfonyl-3-nitrobenzoic acid (0.27 g, 1.10 mmol) in 30 mL of dry dichloromethane under nitrogen was added DMF (50 μL) and the solution cooled to zero degrees in an ice water bath. Oxalyl chloride (0.106 mL, 1.21 mmol) was added and the mixture was stirred for 30 minutes and then allowed to warm to room temperature. After 3 hours, the mixture was concentrated to dryness and then redissolved in 50 mL of dry tetrahydrofuran. This THF solution was added dropwise, under nitrogen, over a 5 h period, to a stirred suspension of 2,2'-[(E)-1,2-ethenediyl]bis[5-aminobenzenesulfonic acid], bis(1-methylethyl) ester (Example 22, 1.0 g, 2.20 mmol) and potassium carbonate (0.608 g, 4.40 mmol) in 170 mL of dry THF. The resulting reaction mixture was stirred overnight. The suspension was concentrated to near dryness and then diluted with ethyl acetate (300 mL) and a small amount of water (20 mL). The mixture was washed with concentrated sodium bicarbonate solution followed by brine. The organic layer was dried ($MgSO_4$) and filtered. Concentration followed by flash column chromatography using a 5 to 20% ethyl acetate in dichloromethane gradient yielded 410 mg (56%) of the title compound as a yellow solid: $^1$HNMR (DMSO-d6) δ11.12 (s, 1H), 8.64 (d, J=1 Hz, 1H), 8.55 (d, J=2 Hz, 1H), 8.49 (dd, J=8 Hz, 1 Hz, 1H), 8.32(d, J=8 Hz, 1H), 8.21 (dd, J=9 Hz, 2 Hz, 1H), 7.85 (d, J=9 Hz, 1H), 7.65 (d, J=16 Hz, 1H), 7.57 (d, J=9 Hz, 1H), 7.48 (d, J=16 Hz, 1H), 7.25 (d, J=2 Hz, 1H), 6.95 (dd, J=8 Hz, 2 Hz, 1H), 6.10 (br s, 2H), 4.59 (m, 2H), 3.56 (s, 3H), 1.20 (m, 12H); MS (ES-NEG): [M−H] 680; Anal.Calc. for $C_{28}H_{31}N_3O_{11}S_3$: C,49.33; H,4.58; N,6.16. Found: C,49.08; H,4.35; N, 6.00.

EXAMPLE 28b

5-[[4-(Methylsulfonyl)benzoyl]amino]-2-[(E)-2-[4-amino-2-sulfophenyl]ethenyl]benzenesulfonate, Bis (1-methylethyl) Ester Prepared according to the procedure for Example 28a except using commercially available 4-(methylsulfonyl) benzoic acid in place 4-methylsulfonyl-3-nitrobenzoic acid (55%): $^1$HNMR (DMSO-d$_6$) δ10.99 (s, 1H), 8.60 (d, J=2 Hz, 1H), 8.20 (m, 3H), 8.12 (d, J=8 Hz, 2H), 7.82 (d, J=9 Hz, 1H), 7.61–7.39 (m, 3H), 7.24 (dd, J=8 Hz, 2 Hz, 1H), 6.93 (triplet of d, J=9 Hz, 2 Hz, 1H), 4.58 (m, 4H), 3.31 (s, 3H), 1.19 (m, 12H).

EXAMPLE 29a

2[(E)-2-[2-(Isopropoxysulfonyl)-4-[[4-(methylsulfonyl)-3-nitrobenzoyl]amino]phenyl] ethenyl]-5-[[4-(methylthio)-3-(4-morpholinylsulfonyl)benzoyl]amino] benzenesulfonic Acid, (1-Methylethyl) Ester To a solution of 4-methylsulfanyl-3-(morpholino-4-sulfonyl)-benzoic acid (Example 3, 0.105 g, 0.33 mmol) in 15 mL of dry dichloromethane under nitrogen was added DMF (50 μL) and the solution cooled to zero degrees in an ice water bath. Ooxalyl chloride (0.030 mL, 0.345 mmol) was added and the mixture stirred for 30 minutes and then allowed to warm to room temperature. After 3 hours total the mixture was concentrated to dryness and then redissolved in 15 mL of dry tetrahydrofuran. This THF solution was added, under nitrogen, to a stirred suspension of 5-[[4-(methylsulfonyl)-3-nitrobenzoyl]amino]-2-[(E)-2-[4-amino-2-sulfophenyl]ethenyl]benzenesulfonic acid, bis(1-methylethyl) ester (Example 28a, 0.10 g, 0.15 mmol) and potassium carbonate (0.125 g, 0.90 mmol) in 15 mL of THF. The resulting reaction mixture was stirred overnight. The suspension was concentrated to near dryness and then diluted with ethyl acetate (150 mL). The mixture was washed with saturated sodium bicarbonate, followed by brine. The organic layer was dried ($MgSO_4$) and filtered. Concentration, followed by flash column chromatography using 5% methanol in dichloromethane as an eluant yielded 25 mg (17%) of the title compound as a yellow solid: $^1$HNMR (DMSO-d$_6$) δ11.18 (s, 1H), 10.91 (s, 1H), 8.65 (d, J=1 Hz, 1H), 8.60 (t, 3 Hz, 2H), 8.51 (dd, J=8 Hz, 1 Hz, 1H), 8.43 (d, J=2 Hz, 1H), 8.33 (d, J=8 Hz, 1H), 8.27 (m, 3H), 7.93 (t, J=9 Hz, 2H), 7.73 (s, 2H), 7.68 (d, J=9 Hz, 1H), 4.67 (m, 2H), 3.62 (m, 4H), 3.57 (s, 3H), 3.15 (m, 4H), 2.63 (s, 3H), 1.24 (m, 12H); MS (ESI): [M+NH$_4$] 998; Anal RP-HPLC 90% pure, one major peak.

By a procedure analogous to Example 29a, but using a different benzoic acid in place of 4-methylsulfanyl-3-(morpholino-4-sulfonyl)-benzoic acid and/or a different 5-aminobenzenesulfonate in place of 5-[[4-(methylsulfonyl)-3-nitrobenzoyl]amino]-2-[(E)-2-[4-amino-2-sulfophenyl]ethenyl]benzenesulfonic acid, bis(1-methylethyl) ester, the following compounds in Examples 29b to 29c were prepared.

EXAMPLE 29b

2-[(E)-2-[2-(Isopropoxysulfonyl)-4-[[4-methoxy-3-[[(2-methoxyethyl)amino]sulfonyl]benzoyl]amino] phenyl]ethenyl]-5-[[(4-(methylsulfonyl)-3-nitrobenzoyl]amino]benzenesulfonic Acid, (1-Methylethyl) Ester From 4-Methoxy-3-(2-methoxy-ethylsulfamoyl)-benzoic acid, Example 1k and 5-[[4-(methylsulfonyl)-3-nitrobenzoyl]amino]-2-[(E)-2-[4-amino-2-sulfophenyl] ethenyl]benzenesulfonic acid, bis(1-methylethyl) ester, Example 28a (83%): MS (−ESI): [M−H]− 951.

EXAMPLE 29c

2-[(E)-2-[2-(Isopropoxysulfonyl)-4-[[4-(methylsulfonyl)benzoyl]amino]phenyl]ethenyl]-5-[[4-methoxy-3-(4-morpholinylsulfonyl)benzoyl] amino]benzenesulfonic acid, (1-Methylethyl) Ester From 4-methoxy-3-(morpholine-4-sulfonyl)-benzoic acid, Example 1a and 5-[[4-(methylsulfonyl)benzoyl] amino]-2-[(E)-2-[4-amino-2-sulfophenyl]ethenyl] benzenesulfonate, bis(1-methylethyl) ester, Example 28b (52%): MS (−ESI): [M−H]− 918.

EXAMPLE 30a 2,2'-[(E)-1,2-Ethenediyl]bis[5-[[4-[2-(2-methoxyethoxy)ethoxy]-3-(4-morpholinylsulfonyl) benzoyl]amino]benzenesulfonic Acid]

2,2'-[(E)-1,2-Ethenediyl]bis[5-[[4-(2-(2-methoxyethoxy) ethoxy)-3-(4-morpholinosulfonyl)benzoyl]amino] benzenesulfonic acid], bis(1-methylethyl) ester (Example 27b, 0.07 mmol, 80 mg) was suspended in acetone (3 mL) and sodium iodide (0.27 mmol, 40 mg) was added. The mixture was stirred at 90° C. for 12 h. It was filtered, washed several times with acetone, and filtered again, to provide the bis(sodium) salt of the title compound (72 mg, 89%). $^1$HNMR (DMSO-$_6$) δ10.47 (s, 2H), 8.43 (m, 2H), 8.34 (d, 2H, J=8 Hz), 8.21 (m, 2H), 8.06 (s, 2H), 7.98 (d, J=8 Hz, 2H), 7.60 (d, J=8 Hz, 2H), 7.62 (d, J=8 Hz, 2H), 4.49 (m, 4H), 3.81 (m, 4H), 3.72 (m, 4H), 3.23 (s, 6H), 3.10 (m, 4H); MS (ESI-NEG):[M−H]−1111; Anal.Calc. for $C_{46}H_{56}N_4O_{20}S_4$: C, 47.75; H, 4.70; N, 4.84. Found: C, 45.01; H, 4.58; N, 4.54.

By a procedure analogous to Example 30a, but using a different benzenesulfonic acid, bis(1-methylethyl) ester in place of 2,2'-[(E)-1,2-ethenediyl]bis[5-[[4-(2-(2-methoxyethoxy)ethoxy)-3-(4-morpholinosulfonyl)benzoyl] amino]benzenesulfonic acid], bis(1-methylethyl) ester, the following compounds in Examples 30b to 30s were prepared.

EXAMPLE 30b 2,2'-[(E)-1,2-Ethenediyl]bis[5-[[4-(methylthio)-3-(4-morpholinylsulfonyl)benzoyl]amino]benzenesulfonic Acid]

Bis(sodium) salt prepared from 2,2'-[(E)-1,2-ethenediyl]bis[5-[[4-(methylthio)-3-(4-morpholinylsulfonyl)benzoyl]amino]benzenesulfonic acid], bis(1-methylethyl) ester, Example 27k (81%): –ESI: [M–H]– 1066.

EXAMPLE 30c 2.2'-[(E)-1,2-Ethenediyl]bis[5-[[(4-methylsulfonyl)-3-(nitro)-benzoyl]amino]benzenesulfonic Acid]

Bis(sodium) salt prepared from 2,2'-[(E)-1,2-ethenediyl]bis[5-[[(4-methylsulfonyl)-3-(nitro)-benzoyl]amino]benzenesulfonic acid], bis(1-methylethyl) ester, Example 27m (72%): –ESI: [M–H]– 989.

EXAMPLE 30d 2,2'-[(E)-1,2-Ethenediyl]bis[5-[[4-(methylsulfonyl)-3-(4-morpholinylsulfonyl)benzoyl]amino]benzenesulfonic Acid]

Bis(sodium) salt prepared from 2,2'-[(E)-1,2-Ethenediyl]bis[5-[[4-(methylsulfonyl)-3-(4-morpholinylsulfonyl)benzoyl]amino]benzenesulfonic acid], bis(1-methylethyl) ester, Example 27v (83%): –ESI: [M–H]– 1031.

EXAMPLE 30e

5-[[4-(Methylsulfonyl)-3-nitrobenzoyl]amino]-2-[(E)-2-[4-[[4-(methylthio)-3-(4-morpholinylsulfonyl)benzoyl]amino]-2-sulfophenyl]ethenyl]benzenesulfonic Acid]

Bis(sodium) salt prepared from 2-[(E)-2-[2-(isopropoxysulfonyl)-4-[[4-(methylsulfonyl)-3-nitrobenzoyl]amino]phenyl]ethenyl]-5-[[4-(methylthio)-3-(4-morpholinylsulfonyl)benzoyl]amino]benzenesulfonic acid, (1-methylethyl) ester, Example 29a (51%): +ESI: [M+Na]+ 919.

EXAMPLE 30f

5-[[4-Methoxy-3-[[(2-methoxyethyl)amino]sulfonyl]benzoyl]amino]-2-[(E)-2-[4-[[4-(methylsulfonyl)-3-nitrobenzoyl]amino]-2-sulfophenyl]ethenyl]benzenesulfonic Acid]

Bis(sodium) salt prepared from 2-[(E)-2-[2-(isopropoxysulfonyl)-4-[[4-methoxy-3-[[(2-methoxyethyl)amino]sulfonyl]benzoyl]amino]phenyl]ethenyl]-5-[[4-(methylsulfonyl)-3-nitrobenzoyl]amino]benzenesulfonic acid, (1-methylethyl) ester, Example 29b (29%): –ESI: [M–H]– 867.

EXAMPLE 30g

5-[[4-Methoxy-3-(4-morpholinylsulfonyl)benzoyl]amino]-2-[(E)-2-[4-[[4-(methylsulfonyl)benzoyl]amino]-2-sulfophenyl]ethenyl]benzenesulfonic Acid]

Bis(sodium) salt prepared from 2-[(E)-2-[2-(isopropoxysulfonyl)-4-[[4-(methylsulfonyl)benzoyl]amino]phenyl]ethenyl]-5-[[4-methoxy-3-(4-morpholinylsulfonyl)benzoyl]amino]benzenesulfonic acid, (1-methylethyl) ester, Example 29c (72%): ES-NEG: [M–2H/2]– 416.

EXAMPLE 30h 2,2'-[(E)-1,2-Ethenediyl]bis[5-[[4-methoxy-3-(1-piperidinylsulfonyl)benzoyl]amino]benzenesulfonic Acid]

Bis(sodium) salt prepared from 2,2'-[(E)-1,2-ethenediyl]bis[5-[[4-methoxy-3-(1-piperidinylsulfonyl)benzoyl]amino]benzenesulfonic acid], bis(1-methylethyl) ester, Example 27f (10%): –ESI: [M–H]– 931.

EXAMPLE 30i 2,2'-[(E)-1 2-Ethenediyl]bis[5-[[4-methoxy-3-[(4-methyl-1-piperazinyl)sulfonyl]benzoyl]amino]benzenesulfonic acid]

Bis(sodium) salt prepared from 2,2'-[(E)-1,2-ethenediyl]bis[5-[[4-methoxy-3-[(4-methyl-1-piperazinyl)sulfonyl]benzoyl]amino]benzenesulfonic acid], bis(1-methylethyl) ester, Example 27e (13%): –ESI: [M–H]– 961.

EXAMPLE 30j 2,2'-[(E)-1,2-Ethenediyl]bis[5-[[4-methoxy-3-[(phenyl-1-piperazinyl)sulfonyl]benzoyl]amino]benzenesulfonic Acid]

Bis(sodium) salt prepared from 2,2'-[(E)-1,2-ethenediyl]bis[5-[[4-methoxy-3-[(4-phenyl-1-piperazinyl)sulfonyl]benzoyl]amino]benzenesulfonic Acid], bis(1-methylethyl) ester, Example 27d (20%):–ESI: [M–H]– 1085.

EXAMPLE 30k 2,2'-[(E)-1,2-Ethenediyl]bis[5-[[3-[(1,1-dioxido-4-thiomorpholinyl)sulfonyl]-4-methoxybenzoyl]amino]benzenesulfonic Acid]

Bis(sodium) salt prepared from 2,2'-[(E)-1,2-ethenediyl]bis[5-[[3-[(1,1-dioxido-4-thiomorpholinyl)sulfonyl]-4-methoxybenzoyl]amino]benzenesulfonic acid], bis(1-methylethyl) ester, Example 27c (18%):–ESI: [M–H]– 1031.

EXAMPLE 30l 2,2'-[(E)-1,2-Ethenediyl]bis[5-[[4-[(2-methoxyethyl)amino]-3-(4-morpholinylsulfonyl)benzoyl]amino]benzenesulfonic Acid]

Bis(sodium) salt prepared from 2,2'-[(E)-1,2-Ethenediyl]bis[5-[[4-[(2-methoxyethyl)amino]-3-(4-morpholinylsulfonyl)benzoyl]amino]benzenesulfonic Acid], Bis(1-methylethyl) Ester, Example 27g (15%):–ESI: [M–H]– 1021.

EXAMPLE 30m 2,2'-[(E)-1,2-Ethenediyl]bis[5-[[4-methoxy-3-[[(2-methoxyethyl)amino]sulfonyl]benzoyl]amino]benzenesulfonic Acid]

Bis(sodium) salt prepared from 2,2'-[(E)-1,2-ethenediyl]bis[5-[[4-methoxy-3-[[(2-methoxyethyl)amino]sulfonyl]benzoyl]amino]benzenesulfonic acid], bis(1-methylethyl) ester, Example 27h (27%): –ESI: [M–H]– 911.

EXAMPLE 30n 2,2'-[(E)-1,2-Ethenediyl]bis[5-[[4-methoxy-3-[[2-(4-morpholinyl)ethyl]amino]sulfonyl]benzoyl]amino]benzenesulfonic Acid]

Bis(sodium) salt prepared from 2,2'-[(E)-1,2-ethenediyl]bis[5-[[4-methoxy-3-[[[2-(4-morpholinyl)ethyl]amino]

sulfonyl]benzoyl]amino]benzenesulfonic acid], bis(1-methylethyl) ester, Example 27i (30%): –ESI: [M–H]– 1021.

EXAMPLE 30o 2,2'-[(E)-1,2-Ethenediyl]bis[5-[[3-[[bis(2-methoxyethyl)amino]sulfonyl]-4-methoxybenzoyl]amino]benzenesulfonic Acid]

Bis(sodium) salt prepared from 2,2'-[(E)-1,2-ethenediyl]bis[5-[[3-[[bis(2-methoxyethyl)amino]sulfonyl]-4-methoxybenzoyl]amino]benzenesulfonic acid], bis(1-methylethyl) ester, Example 27l (19%): –ESI: [M–H]– 1027.

EXAMPLE 30p 2,2'-(1,2-Ethanediyl)bis[5-[[4-methoxy-3-(4-morpholinylsulfonyl)benzoyl]amino]benzenesulfonic Acid]

Bis(sodium) salt prepared from 2,2'-(1,2-ethanediyl)bis[5-[[4-methoxy-3-(4-morpholinylsulfonyl)benzoyl]amino]benzenesulfonic acid], bis(1-methylethyl) ester, Example 27n (25%): –ESI: [M–H]– 938.

EXAMPLE 30q 2,2'-[(E)-1,2-Ethenediyl]bis[5-[[4-(methylsulfonyl)benzoyl]amino]benzenesulfonic Acid]

Bis(sodium) salt prepared from 2,2'-[(E)-1,2 ethenediyl]bis[5-[[4-(methylsulfonyl) benzoyl]amino]benzenesulfonic acid], bis(1-methylethyl) ester, Example 27a (71%): $^1$HNMR (DMSO-d$_6$) δ10.63 (s, 2H), 8.23 (m, 6H), 8.08 (m, 6H), 7.90 (d, J=6 Hz, 2H), 7.63 (d, J=8 Hz, 2H), 3.34 (s, 6H).

EXAMPLE 30r 2,2'-[(E)-1,2-Ethenediyl]bis[5-[[3-(4-morpholinylsulfonyl)-4-[(tetrahydro-2H-pyran-4-yl)oxy]benzoyl]amino]benzenesulfonic Acid]

Bis(sodium) salt prepared from 2,2'-[(E)-1,2-ethenediyl]bis[5-[[3-(4-morpholinylsulfonyl)-4-[(tetrahydro-2H-pyran-4-yl)oxy]benzoyl]amino]benzenesulfonic acid], bis(1-methylethyl) ester, Example 27j (85%): –ESI: [M–H]– 1075.

EXAMPLE 30s 2,2'-[(E)-1,2-Ethenediyl]bis[5-[[4-methoxy-3-(4-morpholinylsulfonyl)benzoyl]amino]benzenesulfonic Acid]

Bis(sodium) salt prepared from 2,2'-[(E)-1,2-ethenediyl]bis[5-[[4-methoxy-3-(4-morpholinylsulfonyl)benzoyl]amino]benzenesulfonic acid], bis(1-methylethyl) ester, Example 27w (78%): ES (NEG) [M+Na–H]– 957.

EXAMPLE 30t 2,2'-[(E)-1,2-Ethenediyl]bis[5-[[4-(2-methoxyethoxy)-3-(4-morpholinylsulfony)benzoyl]amino]benzenesulfonic Acid]

Bis(sodium) salt prepared from 2,2'-[(E)-1,2-ethenediyl]bis[5-[[4-(2-methoxyethoxy)-3-(4-morpholinylsulfony)benzoyl]amino]benzenesulfonic acid], bis(1-methylethyl) ester, Example 27x (77%): –ESI: [M–H]– 1023.

EXAMPLE 30u 2,2'-[(E)-1,2-Ethenediyl]bis[5-[[4-(2-furanylmethoxy)-3-(4-morpholinylsulfony)benzoyl]amino]benzenesulfonic Acid]

Bis(sodium) salt prepared from 2,2'-[(E)-1,2-ethenediyl]bis[5-[[4-(2-furanylmethoxy)-3-(4-morpholinylsulfony)benzoyl]amino]benzenesulfonic acid], bis(1-methylethyl) ester, Example 27y (71%): MS(ESI-NEG): [M–H]– 1067.

EXAMPLE 31

2,2'-[(E)-1,2-Ethenediyl]bis[5-aminobenzenesulfonic Acid, Bis(tetra-N-butylammonium) Salt Commercially available 4,4'-diaminostilbene-2,2'-disulfonic acid (2.0 g, 5.4 mmol) was suspended in water (16 mL) and treated with 1 M tetra-n-butylammonium hydroxide solution (11.2 mL, 11.2 mmol). The resulting solution was stirred at rt for one hour and then extracted with methylene chloride (3×50 mL). The methylene chloride extract was washed, dried and evaporated to dryness to afford 3.48 g (75% yield) the title compound as a white solid: $^1$HNMR (CDCl$_3$) δ0.90 (m, 24H), 1.25 (m, 16H), 1.45 (m, 16H), 3.00 (m, 16H), 6.57 (d, J=8 Hz, 2H), 7.40 (s, 2H), 7.65 (d, J=8 Hz, 2H), 8.07 (s, 2H); MS (ES-Neg): [M–H]– 369.

EXAMPLE 32a 2,2-[(E)-1,2-Ethenediyl]bis[5-[[4-(2-propenylsulfonyl)benzoyl]amino]benzenesulfonic Acid A solution of 4-allylsulfonyl-benzoic acid, (Example 18a, 225 mg, 1.0 mmol) in dichloromethane (1.5 mL) was treated with DMF (2 drops) and oxalylchloride (1.5 mL) at 0° under a dry N$_2$ atmosphere. After 3 hours, the solution was evaporated and the residue was dried. This residue was dissolved in dichloromethane (4.5 mL) and added to a 0°, stirred solution of 2,2'-[(E)-1,2-ethenediyl]bis[5-aminobenzenesulfonic acid, bis(tetra-N-butylammonium) salt (Example 31, 427 mg, 0.5 mmol) and triethylamine (141 mg, 1.4 mmol) in dichloromethane (25 mL). The resulting suspension was stirred at for 2 hours at 0° and at room temperature for additional 18 hours. It was diluted with 8% methanol in dichloromethane (200 mL), washed, dried and evaporated. Chromatography of the crude product on silica gel and elution with 7% methanol in dichloromethane afforded 55 mg (10% yield) of the bis(tetra-N-butylammonium) salt of the title compound as a yellow solid: $^1$HNMR (DMSO-d$_6$) δ0.93 (m, 24H), 1.30 (m, 16H), 1.6 (m, 16 H), 3.13 (m, 16H), 4.20 (d, J=7 Hz, 4H), 5.30 (m, 4H), 5.70 (m, 2H), 7.60–8.30 (m, 16H); Analytical HPLC= 97% pure; MS (ES Neg): [M–H]– 785.

This bis(tetra-N-butylammonium) salt (50 mg) was dissolved in methanol/deionized water (5/3) (8 ml) and poured into an ion exchange resin column (3×20 cm, Toyopearl SP-650C, size range 100 micron). Elution with 10% methanol in deionized water (400 ml) and freeze-drying the eluent afforded 50 mg (100% yield) of the bis(sodium) salt of the title compound as a white solid: $^1$HNMR (DMSO-d$_6$) δ4.21 (d, J=7 Hz, 4H), 5.28 (m, 4H), 5.71 (m, 2H), 7.60–8.25 (m, 16H) ppm; Analytical HPLC=95.5% pure; MS (ES Neg): [M–H]– 785.

By a procedure analogous to Example 32a, but using a different benzoic acid in place of 4-allylsulfonyl-benzoic acid, the following compounds in Examples 32b to 32q were prepared.

EXAMPLE 32b 2,2'-[(E)-1,2-Ethenediyl]bis[5-[[[5-(methylsulfonyl)-2-thienyl]carbonyl]amino]benzenesulfonic Acid]

Bis(tetra-N-butylammonium) salt prepared from 5-methyl-sulfonyl-2-thiophenecarboxylic acid, Example 18f (7%): MS (ES-Neg): [M–H]⁻ 745. Bis(sodium) salt (98%): MS (ES-Neg): [M–H]⁻745.

EXAMPLE 32c

[4-(4-{2-[4-(4-Methoxycarbonylmethanesulfonyl-benzoylamino)-2-sulfo-phenyl]-vinyl}-3-sulfo-phenylcarbomoyl)-benzenesulfonyl]-acetic Acid, Methyl Ester Bis(tetra-N-butylammonium) salt prepared from 4-[(methoxycarbonyl)methanesulfonyl]benzoic acid, Example 18b (49%): MS (ES-Neg): [M–H]$^{31}$ 849.

EXAMPLE 32d.

[3-(4-{2-[4-(3-Methoxycarbonylmethanesulfonyl-benzoylamino)-2-sulfo-phenyl]-vinyl}-3-sulfo-phenylcarbomoyl)-benzenesulfonyl]-acetic Acid, Methyl Ester Bis(tetra-N-butylammonium) salt prepared from 3-[(methoxycarbonyl)methanesulfonyl]benzoic acid, Example 18d (55%): MS (ES-Neg): [M–H]⁻ 849.

EXAMPLE 32e

4-{3-[4-(2-{4-{3-(3-Methoxycarbonyl-prop-2-ene-1-sulfonyl)-benzoylamino]-2-sulfo-phenyl}-vinyl)-3-sulfo-phenylcarbomoyl]-benzenesulfonyl}-but-2-enoic Acid, Methyl Ester Bis(tetra-N-butylammonium) salt prepared from 4-(3-methoxycarbonyl-2-propenyl)sulfonyl-benzoic acid, Example 18c (47%): MS (ES-Neg): [M–H]⁻ 901.

EXAMPLE 32f 2,2'-[(E)-1,2-Ethenediyl]bis[5-[[4-(ethylsulfonyl)benzoyl]amino]benzenesulfonic Acid]

Bis(tetra-N-butylammonium) salt prepared from 4-ethylsulfonylbenzoic acid, Example 18e (18%): MS (ESI) [M–H]⁻ at m/z 761. Bis(sodium) salt (96%): MS (ESI) [M–H] at m/z 761.

EXAMPLE 32g 2,2'-[(E)-1,2-Ethenediyl]bis[5-[[4-[(methylsulfonyl)methyl]benzoyl]amino]benzenesulfonic Acid]

Bis(triethylammonium) salt prepared after HPLC purification from 4-methanesulfonylmethylbenzoic acid, Example 19 (2%): MS (ESI) [M–H]⁻ at m/z 762.

EXAMPLE 32h 2,2'-[(E)-1,2-Ethenediyl]bis[5-[[4-(butylthio)-3-(4-morpholinylsulfonyl)benzoyl]amino]benzenesulfonic Acid]

Bis(tetra-N-butylammonium) salt prepared from 4-butylsulfanyl-3-(morpholine-4-sulfonyl)-benzoic acid, Example 7b (72%): MS (ESI) [M–H]⁻ at m/z 1051. Bis(sodium) salt (62%): MS (ESI) [M–H]⁻ at m/z 1051.

EXAMPLE 32i 2,2'-[(E)-1,2-Ethenediyl]bis[5-[[4-(ethylthio)-3-(4-morpholinylsulfonyl)benzoyl]amino]benzenesulfonic Acid]

Bis(tetra-N-butylammonium) salt prepared from 4-ethylsulfanyl-3-(morpholine-4-sulfonyl)-benzoic acid, Example 7a (30%): MS (ESI) [M–H]⁻ at m/z 995. Bis(sodium) salt (73%): MS (ESI) [M–H]⁻ at mn/z 995.

EXAMPLE 32j 2,2'-[(E)-1,2-Ethenediyl]bis[5-[[4-(isopropylthio)-3-(4-morpholinylsulfonyl)benzoyl]amino]benzenesulfonic Acid]

Bis(tetra-N-butylammonium) salt prepared from 4-isopropylsulfanyl-3-(morpholine-4-sulfonyl)-benzoic acid, Example 7c (50%): MS (ESI) [M–H]⁻ at m/z 1023. Bis(sodium) salt (50%): MS (ESI) [M–H]⁻ at m/z 1023.

EXAMPLE 32k 2,2'-[(E)-1,2-Ethenediyl]bis[5-[[4-(4-morpholinyl)-3-(4-morholinylsulfonyl)benzoyl]amino]benzenesulfonic Acid]

Bis(tetra-N-butylammonium) salt prepared from 3-(morpholine-4-sulfonyl)-4-morpholin-4-yl-benzoic acid, Example 8a (27%): MS (ESI) [M–H]⁻ at m/z 1045. Bis(sodium) salt (6%): MS (ESI) [M–H]⁻ at m/z 1045.

EXAMPLE 32l 2,2'-[(E)-1,2-Ethenediyl]bis[5-[[4-[(2-methoxyethyl)thiol-3-(4-morpholinylsulfonyl)benzoyl]amino]benzenesulfonic Acid]

Bis(tetra-N-butylammonium) salt prepared from 4-(2-methoxyethylsulfanyl)-3-(morpholine-4-sulfonyl)-benzoic acid, Example 10a (29%): MS (ESI) [M–H]⁻ at m/z 1055. Bis(sodium) salt (45%): MS (ESI) [M–H]⁻ at m/z 1055.

EXAMPLE 32m 2,2'-[(E)-1,2-Ethenediyl]bis[5-[[4-[bis(2-methoxyethyl)amino]-3-(4-morpholinylsulfonyl)benzoyl]amino]benzenesulfonic Acid]

Bis(tetra-N-butylammonium) salt prepared from 4-[bis(2-methoxyethyl)amino]-3-(morpholine-4-sulfonyl)-benzoic acid, Example 8b (33%): MS (ESI) [M–H]⁻ at m/z 1137.

EXAMPLE 32n 2,2'-[(E)-1,2-Ethenediyl]bis[5-[[4-(dimethylamino)-3-(4-morpholinylsulfonyl)benzoyl]amino]benzenesulfonic Acid]

Bis(tetra-N-butylammonium) salt prepared from 4-dimethylamino-3-(morpholine-4-sulfonyl)-benzoic acid, Example 8c (25%): MS (ESI) [M–H]⁻ at m/z 963. Bis(sodium) salt (45%): MS (ESI) [M–H]⁻ at m/z 963.

EXAMPLE 32o 2,2'-[(E)-1,2-Ethenediyl]bis[5-[[4-[[2-(2-methoxyethoxy)ethyl]thio-3-(4-morpholinylsulfonyl)benzoyl]amino]benzenesulfonic Acid]

Bis(tetra-N-butylammonium) salt prepared from 4-[2-(2-methoxyethoxy)ethylsulfanyl]-3-(morpholine-4-sulfonyl)benzoic acid, Example 10b (47%): MS (ESI) [M–H]⁻ at m/z 1143. Bis(sodium) salt (67%): MS (ESI) [M–H]⁻ at m/z 1143.

EXAMPLE 32p

[4-[4-(2-{4-[4-Methoxycarbonylmethanesulfanyl-3-(morpholine-4-sulfonyl)-benzoylamino]-2-sulfo-phenyl}-(E)-vinyl)-3-sulfo-phenylcarbamoyl]-2-(morpholine-4-sulfonyl)-phenylsulfanyl]-acetic Acid, Methyl Ester Bis(tetra-N-butylammonium) salt prepared from 4-(methoxycarbonylmethyl)sulfanyl-3-(morpholine-4- sulfonyl)-benzoic acid, Example 7d (24%): MS (ESI) [M–H]− at m/z 1083.

Bis(sodium) salt (48%): MS (ESI) [M–H]− at m/z 1083.

EXAMPLE 32q 2,2'-(1,2-Ethanediyl)bis[5-[[4-(tetrahydro-2-furanmethyl)-3-(4-morpholinylsulfonyl)benzoyl]amino]benzenesulfonic Acid]

Bis(tetra-N-butylammonium) salt prepared from 3-(morpholine-4-sulfonyl)-4-(tetrahydro-furan-2-ylmethoxy)-benzoic acid, Example 7e (23%): MS (ESI) [M–H]− at m/z 1075. Bis(sodium) salt (84%): MS (ESI) [M–H]− at m/z 1075.

EXAMPLE 33a 2,2'-[(E)-1,2-Ethenediyl]bis[5-[[3-(4-morpholinylsulfonyl)benzoyl]amino]benzenesulfonic Acid]

3-(Morpholine-4-sulfonyl)-benzoic acid (Example 15, 271 mg, 1 mmol) was suspended in dichloromethane (3 mL), and DMF (2 drops) was added. Oxalyl chloride (152 mg, 1.2 mmol) was added slowly, and the reaction mixture was allowed to stir for 2 h. The solvent was removed under reduced pressure and the acid chloride was dissolved in dimethylacetamide (0.5 mL). This solution was added to a stirred solution of commercially available 4,4'-diaminostilbene-2,2'-disulfonic acid (110 mg, 0.33 mmol) and diisopropylethyamine (129 mg, 1 mmol) in dimethylacetamide (0.5 mL). The resulting solution was heated to 80° C. After 12 h, the solvent was removed under reduced pressure. The residue was added to aqueous sodium bicarbonate and stirred. The precipitate was filtered to provide the (bis)sodium salt of the title as a yellow solid (88 mg, 30%):$^1$HNMR (DMSO-$d_6$) δ0.41 (s, 2H), 8.43 (d, J=3 Hz, 2H), 8.34 (m, 2H), 8.21 (d, J=2 Hz, 2H), 8.08 (s, 2H), 7.94 (m, 2H),7.80 (t, J=8 Hz, 2H), 7.62 (d, 8 Hz, 2H), 3.72 (m, 4H), 3.10 (m, 4H); MS (ESI-NEG):[M–2H+Na]–897; Anal. Calc. for $C_{36}H_{36}N_4O_{14}S_4$: C, 49.31; H, 4.14; N, 6.39. Found: C, 42.78; H, 3.83; N, 5.53.

By a procedure analogous to Example 33a, but using a different benzoic acid in place of 3-(morpholine-4-sulfonyl)-benzoic acid and/or a different aminobenzenesulfonate in place of 4,4'-diaminostilbene-2,2'-disulfonic acid, the following compounds in Examples 33b to 33h were prepared.

EXAMPLE 33b 2,2'-[(E)-1,2-Ethenediyl]bis[5-[[3-(4-morpholinylmethyl)benzoyl]amino]benzenesulfonic Acid]

The (bis)sodium salt was prepared from 3-morpholin-4-yl-methyl-benzoic acid, Example 14 and commercially available 4,4'-diaminostilbene-2,2'-disulfonic acid (11%): ES-NEG [M–H]− 775.

EXAMPLE 33c 2,2'-[(E)-1,2-Ethenediyl]bis[5-[[3-[(diethylamino)sulfonyl]-4-methoxybenzoyl]amino]benzenesulfonic Acid]

The (bis)sodium salt was prepared from 3-diethylsulfamoyl-4-methoxy-benzoic acid, Example 1b and commercially available 4,4'-diaminostilbene-2,2'-disulfonic acid (29%): –ESI: [M–H]– 907.

EXAMPLE 33d 2,2'-[(E)-1,2-Ethenediyl]bis[5-[[4-methoxy-3-(4-thiomorpholinylsulfonyl)benzoyl]amino]benzenesulfonic Acid]

The (bis)sodium salt was prepared from 4-methoxy-3-(thiomorpholine-4-sulfonyl)-benzoic acid, Example 1e and commercially available 4,4'-diaminostilbene-2,2'-disulfonic acid (30%): –ESI: [M–H]– 967.

EXAMPLE 33e 2,2'-[(E)-1,2-Ethenediyl]bis[5-[[4-methoxy-3-(1-pyrrolidinylsulfonyl)benzoyl]amino]benzenesulfonic Acid]

The (bis)sodium salt was prepared from 4-methoxy-3-(pyrrolidine-1-sulfonyl)-benzoic acid, Example 1d and commercially available 4,4'-diaminostilbene-2,2'-disulfonic acid (23%): –ESI: [M–H]– 903.

EXAMPLE 33f 2,2'-[(E)-1,2-Ethenediyl]bis[5-[[3-[(hexahydro-1H-azepin-1-yl)sulfonyl]-4-methoxybenzoyl]amino]benzenesulfonic Acid The (bis)sodium salt was prepared from 3-(azepane-1-sulfonyl)-4-methoxy-benzoic acid, Example 1c and commercially available 4,4'-diaminostilbene-2,2'-disulfonic acid (42%): –ESI: [M–H]– 959.

EXAMPLE 33g 4,4'-Bis[4-methoxy-3-(morpholine-4-sulfonyl)benzoylamino]biphenyl-2,2'-(bis)sulfonic Acid The (bis)sodium salt was prepared from 4-methoxy-3-(morpholine-4-sulfonyl)-benzoic acid, Example 1a and commercially available 4,4'-diamino-2,2'-biphenyldisulfonic acid (32%): $^1$HNMR (DMSO-$d_6$) δ8.32 (d, J=2 Hz, 2H), 8.16 (m, 4H), 7.56 (dd, J=8 Hz, 2 Hz, 2H), 7.35 (d, J=9 Hz, 2H), 7.25 (d, J=9 Hz, 2H), 4.03 (s, 6H), 3.75 (m, 4H), 3.25 (m, 4H); MS (ESI-NEG):[M–H]–909.

EXAMPLE 33h 2,2'-Thiobis[5-[[4-methoxy-3-(4-morpholinylsulfonyl)benzoyl]amino]benzenesulfonic Acid]

The (bis)sodium salt was prepared from 4-methoxy-3-(morpholine-4-sulfonyl)-benzoic acid, Example 1a and commercially available 2,2'-thiobis(5-aminobenzenesulfonic acid) (41%): $^1$HNMR (DMSO-$d_6$): δ10.47 (s, 2H), 8.38 (d, J=2 Hz, 2H), 8.32 (m, 2H), 8.19 (d, J=2 Hz, 2H), 7.71 (dd, J=9 Hz, 2 Hz, 2H), 741(d, J=8 Hz, 2H), 7.05 (d, J=9 Hz, 2H), 3.82 (m, 4H), 3.23 (s, 6H), 3.12 (m, 4H); MS (ESI-NEG): [M–H]–941.

EXAMPLE 34a 2,2'-[(E)-1,2-Ethenediyl]bis[5-[[3-[(4-acetyl-1-piperazinyl)sulfonyl]-4-methoxybenzoyl]amino]benzenesulfonic Acid]

3-(4-Acetyl-piperazine-1-sulfonyl)-4-methoxy-benzoic acid (Example 1f, 200 mg, 0.58 mmol), 1-[3-(dimethylamino)propyl]-3-ethylcarbodiimide hydrochloride (223 mg, 1.2 mmol) and 2,2'-[(E)-1,2-ethenediyl]bis[5- aminobenzenesulfonic acid], bis(1-methylethyl) ester (Example 22, 132 mg, 0.29 mmol) were suspended in THF (12 mL) and allowed to stir for 24 h. The THF was decanted off and water (3 mL) and sodium iodide (300 mg, 2 mmol) were added. The reaction mixture was heated to 50° C. for 24 h. The solvent was removed under reduced pressure and the remaining solid was taken up in acetone and filtered to provide the (bis)sodium salt of the title product (150 mg, 48%) as a white solid: $^1$HNMR (DMSO-d$_6$) δ0.48 (s, 2H), 8.36(m, 2H), 8.28 (m, 2H), 8.15 (m, 2H) 8.04 (s, 2H), 7.87 (m, 2H), 7.61 (m, 2H), 7.45 (d, J=8 Hz, 2H), 3.86 (m, 8H), 3.16 (m, 8H), 2.01(s, 6H); MS (ESI-NEG):[M−H]−1017.

EXAMPLE 34b 2,2'-[(E)-1,2-Ethenediyl]bis[5-[[3-[(4-formyl-1-piperazinyl)sulfonyl]-4-methoxybenzoyl]amino] benzenesulfonic Acid]

The (bis)sodium salt was prepared according to the procedure for Example 34a except using 3-(4-formyl-piperazine-1-sulfonyl)-4-methoxy-benzoic acid, Example 1g in place of 3-(4-acetyl-piperazine-1-sulfonyl)-4-methoxy-benzoic acid (13%): −ESI: [M−H]− 989.

EXAMPLE 35

2,2'-[(E)-1,2-Ethenediyl]bis[5-[[3-amino-4-(methylsulfonyl)benzoyl]amino]benzenesulfonic Acid]

To a solution of 2,2'-[(E)-1,2-ethenediyl]bis[5-[[(4-methylsulfonyl)-3-(nitro)-benzoyl]amino]benzenesulfonic acid], bis(1-methylethyl) ester (Example 27m, 0.60 g, 0.66 mmol) in 20 mL of ethanol under nitrogen was added tin chloride dihydrate (0.596 g, 2.64 mmol) and the solution was heated to 85 degrees. After eight hours the solution was cooled to room temperature and filtered. The precipitate was washed with ethanol and then dried under vacuum to afford 353 mg of a yellow-brown solid (70%) corresponding to the mono-tin salt of the title compound: $^1$HNMR (DMSO-d$_6$) δ10.48 (s, 2H), 8.23 (d, J=1.5 Hz, 2H), 8.06 (s, 2H), 7.83 (d, J=8 Hz, 2H), 7.64 (d, J=8 Hz, 2H), 7.61 (d, J=9 Hz, 2H), 7.44 (s, 2H), 7.25 (d, J=9 Hz, 2H), 4.94 (br s, 4H), 3.16 (s, 6H); MS: −ESI [M−H]− 763; Anal. Calc. for C$_{30}$H$_{28}$N$_4$O$_{12}$S$_4$Sn-3.5H$_2$O: C, 38.15; H, 3.52; N, 5.93. Found: C, 38.09; H, 3.39; N, 5.76.

EXAMPLE 36a

[4-(4-{2-[4-(4-Carboxymethanesulfonyl-benzoylamino)-2-sulfo-phenyl]-vinyl}-3-sulfo-phenylcarbamoyl)-benzenesulfonyl]-acetic Acid A solution of the bis(tetra-N-butyl)ammonium salt of [4-(4-{2-[4-(4-methoxycarbonylmethanesulfonyl-benzoylamino)-2-sulfo-phenyl]-vinyl}-3-sulfo-phenylcarbomoyl)-benzenesulfonyl]-acetic acid, methyl ester (Example 32c, 100 mg, 0.11 mmol) in methanol (2.5 mL)/water (2.5 mL) was treated with 0.1 N NaOH aqueous solution (2.4 mL, 0.24 mmol) at 0° C. and stirred at rt/N$_2$ for 20 hours. The reaction mixture was cooled to 0°/N$_2$, acidified with 1N HCl (2.4 mL), diluted with methanol (20 mL)/deionized water (20 mL) and poured into an ion exchange resin column (3×20 cm, Toyopearl SP-650C, size range 100 micron). Elution with 5% methanol in deionized water (400 mL) and freeze-drying the eluent afforded 65 mg (94.7% yield) of the tetrasodium salt of the title compound as a yellow powder: $^1$HNMR(DMSO-d$_6$) δ3.96 (s, 2H), 7.6–8.3 (m, 16 H); Analytical HPLC: 81.4% purity; MS (ES-Neg): [M−H]− 821.

By a procedure analogous to Example 36a, but using a different benzenesulfonyl-acetic acid, methyl ester in place of [4-(4-{2-[4-(4-methoxycarbonylmethanesulfonyl-benzoylamino)-2-sulfo-phenyl]-vinyl}-3-sulfo-phenylcarbomoyl)-benzenesulfonyl]-acetic acid, methyl ester, the following compounds in Examples 36b to 36c were prepared.

EXAMPLE 36b

[3-(4-{2-[4-(3-Carboxymethanesulfonyl-benzoylamino)-2-sulfo-phenyl]-vinyl}-3-sulfo-phenylcarbamoyl)-benzenesulfonyl]-acetic Acid The tetrasodium salt was prepared from the bis(tetra-N-butyl)ammonium salt of [3-(4-{2-[4-(3-methoxycarbonylmethanesulfonyl-benzoylamino)-2-sulfo-phenyl]-vinyl}-3-sulfo-phenylcarbomoyl)-benzenesulfonyl]-acetic acid, methyl ester, Example 32d (90%): MS (ES-Neg): [M−H]− 821.

EXAMPLE 36c

4-{3-[4-(2-{4-[3-(3-Carboxy-prop-2-ene-1-sulfonyl)-benzoylamino]-2-sulfo-phenyl}-vinyl)-3-sulfo-phenylcarbomoyl]-benzenesulfonyl}-but-2-enoic Acid The tetrasodium salt was prepared from the bis(tetra-N-butyl)ammonium salt of 4-{3-[4-(2-{4-[3-(3-methoxycarbonyl-prop-2-ene-1-sulfonyl)-benzoylamino]-2-sulfo-phenyl}-vinyl)-3-sulfo-phenylcarbomoyl]-benzenesulfonyl}-but-2-enoic acid, methyl ester, Example 32e (90%): MS (ES-Neg): [M−H]− 873.

EXAMPLE 37a

5-[[4-[[2-[(2-Hydroxyethyl)amino]-2-oxoethyl] sulfonyl]benzoyl]amino]-2-[(E)-2-[4-[[4-[[2-[(2-hydroxyethyl)amino]-2-oxoethyl]sulfonyl]benzoyl] amino]-2-sulfo-phenyl]ethenyl]benzenesulfonic Acid A solution of the bis(tetra-N-butyl)ammonium salt of [4-(4-{2-[4-(4-methoxycarbonylmethanesulfonyl-benzoylamino)-2-sulfo-phenyl]-vinyl}-3-sulfo-phenylcarbomoyl)-benzenesulfonyl]-acetic acid, methyl ester (Example 32c, 70 mg, 0.5 mmol) in methanol (5 mL) was treated with ethanolamine (1 mL) and stirred at rt/N$_2$ for 2 days. All the solvent and reagent were evaporated at 50° under reduced pressure. The solid residue was dissolved in methanol/deionized water (1/9) (50 mL) and poured into an ion exchange resin column (3×20 cm, Toyopearl SP-650C; size range 100 micron). Elution with 10% methanol in deionized water (400 mL) and freeze-drying the eluent afforded 50 mg (98.9% yield) of the (bis)sodium salt of the title compound as a yellow powder: $^1$HNMR (DMSO-d$_6$) δ3.10 (m, 4H), 3.34 (m, 4H), 4.39 (s, 4H), 7.5–8.4 (m, 16H); Analytical HPLC: 75.5% purity; MS (ES-Neg): [M−H]− 819.

By a procedure analogous to Example 37a, but using a different benzenesulfonyl-acetic acid, methyl ester in place of [4-(4-{2-[4-(4-methoxycarbonylmethanesulfonyl-benzoylamino)-2-sulfo-phenyl]-vinyl}-3-sulfo-phenylcarbomoyl)-benzenesulfonyl]-acetic acid, methyl ester and/or a different amine in place of ethanolamine, the following compounds in Examples 37b to 37e were prepared.

EXAMPLE 37b

5-[[4-[(2-Amino-2-oxoethyl)sulfonyl]benzoyl]
amino]-2-[(E)-2-[4-[[4-[(2-amino-2-oxoethyl)
sulfonyl]benzoyl]amino]-2-sulfophenyl]ethenyl]-
benzenesulfonic Acid The bis(sodium) salt was prepared from the bis(tetra-N-butyl)ammonium salt of [4-(4-{2-[4-(4-methoxycarbonylmethanesulfonyl-benzoylamino)-2-sulfophenyl]-vinyl}-3-sulfo-phenylcarbomoyl)-benzenesulfonyl]-acetic acid, methyl ester, Example 32c and 30% NH$_4$OH (99%): MS (ES-Neg): [M–H]$^-$ 819.

EXAMPLE 37c

5-[[3-[[2-[(2-Hydroxyethyl)amino]-2-oxoethyl]
sulfonyl]benzoyl]amino]-2-[(E)-2-[4-[[3-[[2-[(2-
hydroxyethyl)amino]-2-oxoethyl]sulfonyl]benzoyl]
amino]-2-sulfo-phenyl]ethenyl]benzenesulfonic
Acid The bis(sodium) salt was prepared from the bis(tetra-N-butyl)ammonium salt of [3-(4-{2-[4-(3-methoxycarbonylmethanesulfonyl-benzoylamino)-2-sulfophenyl]-vinyl}-3-sulfo-phenylcarbomoyl)-benzenesulfonyl]-acetic acid, methyl ester, Example 32d and ethanolamine (90%): MS (ES-Neg): [M–H]$^-$ 907.

EXAMPLE 37d

5-[[3-[(2-Amino-2-oxoethyl)sulfonyl]benzoyl]
amino]-2-[(E)-2-[4-[[3-[(2-amino-2-oxoethyl)
sulfonyl]benzoyl]amino]-2-sulfophenyl]ethenyl]-
benzenesulfonic Acid The bis(sodium) salt was prepared from the bis(tetra-N-butyl)ammonium salt of [3-(4-{2-[4-(3-methoxycarbonylmethanesulfonyl-benzoylamino)-2-sulfophenyl]-vinyl}-3-sulfo-phenylcarbomoyl)-benzenesulfonyl]-acetic acid, methyl ester, Example 32d and 30% NH$_4$OH (18%): MS (ES-Neg): [M–H]$^-$ 819.

EXAMPLE 37e

5-[[4-[(2-Amino-2-oxoethyl)sulfonyl]benzoyl]
amino]-2-[(E)-2-[4-[[4-[(2-amino-2-oxoethyl)
sulfonyl]berizoyl]amino]-2-[(2,2-dimethylpropoxy)
sulfonyl]phenyl]-ethenyl]benzenesulfonic Acid, 2,2-
Dimethylpropyl Ester From 2,2'-[(E)-1,2-ethenediyl]bis[[[4-[(methoxycarbonyl)methyl-sulfonyl]benzoyl]amino] benzenesulfonic acid], bis(2,2-dimethylpropyl) ester, Example 27u and 14% NH$_3$ in methanol (87%): MS (ES-Neg): [M–H]$^-$ 959.

EXAMPLE 38

5-Amino-2-[(E)-2-[4-[[(1,1-dimethylethoxy)
carbonyl]amino]-2-sulfophenyl]ethenyl]
benzenesulfonic Acid 1M Tetrabutylammonium hydroxide (54 mL, 54 mmol) was added to a solution of commercially available 4,4'-diaminostilbene-2,2'-disulfonic acid (10 g, 27 mmol) in water (80 mL). The resulting orange solution was stirred 10 mins upon which 1M di-tert-butyl dicarbonate in THF (26 mL, 26 mmol) was added dropwise over 20 min. The resulting orange solution was stirred at room temperature for 20 hrs. The reaction mixture was partitioned between methylene chloride (150 mL) and water (20 mL). The organic layer was separated and extracted with water (3×20 mL). It was then dried (MgSO$_4$) and concentrated in vacuum to provide a brown solid. Silica Gel gravitational chromatography (gradient: dichloromethane/methanol) afforded the (tetra-N-butyl)ammonium salt of the title compound as an orange powder (10.45 g, 40% yield): $^1$HNMR (DMSO-d$_6$) δ0.83 (m, 24H), 1.16 (m, 16H), 1.34 (m, 16H), 1.50 (s, 9H), 2.94 (m, 16H), 5.30 (s, 2H), 6.53 (dd, J=6, 3 Hz, 2H), 7.44 (d, J=3 Hz, 1H), 7.47 (dd, J=8, 2 Hz, 1H), 7.69 (dd, J=31, 8, 1H), 7.82 (d, 2 Hz, 1H), 8.10 (dd, 32, 17 Hz, 2H): MS (ESI) [M–H]$^-$ at m/z 469.

EXAMPLE 39a

5-Amino-2-[(E)-2-(4-{[4-(2-methoxyethoxy)
benzoyl]amino}-2-sulfophenyl)ethenyl]
benzenesulfonic Acid Oxalyl chloride (0.5 mL) and DMF (1 drop) were added to a 0° C., stirred solution of 4-methoxyethoxybenzoic acid (Example 16, 0.51 g, 2.6 mmol) in dichloromethane (10 mL) under a dry nitrogen atmosphere, and the yellow solution was stirred for 1 hr. Concentration in vacuum afforded an off white powder. A solution of this powder in dichloromethane (10 mL was added to a 0° C., stirred solution of 5-amino-2-[(E)-2-[4-[[(1,1-dimethylethoxy)carbonyl]amino]-2-sulfophenyl]ethenyl]benzenesulfonic acid (Example 38, 2.50 g, 2.6 mmol) and triethylamine (0.56 g, 5.5 mmol) in dichloromethane (250 mL). The resulting yellow mixture was allowed to warm to room temperature and was stirred 18 hours. Water (75 mL) was added and the layers were separated. The organic phase was dried (MgSO$_4$) and concentrated to provide a yellow powder that was chromatographed (gradient elution MeOH:CH$_2$Cl$_2$) to afford a yellow foam (2.11 g, 1.9 mmol). Trifluoroacetic acid (15 mL) was added and the solution was stirred for 2.5 hrs. The triflouroacetic acid was removed and water (40 mL) and 1M tetrabutylammonium hydroxide (20 mL) to a pH above 10 were added. The reaction mixture was extracted with dichloromethane (75 mL). The organic phase was dried (MgSO$_4$), filtered and concetrated to a brown syrup. Silica gel chromatography (gradient elution MeOH:CH$_2$Cl$_2$) afforded the bis(tetra-N-butyl)ammonium salt of the title compound as a yellow powder (2.01 g, 74% yield): $^1$HNMR (DMSO-d$_6$) δ0.88 (m, 24H) 1.28 (m, 16H), 1.50 (m, 16H), 3.10 (m, 16H), 3.36 (s, 3H), 3.69 (t, J=5 Hz, 2H), 4.18 (t, J=5 Hz, 2H), 5.22 (s, 2H), 6.52 (dd, J=8, 2 Hz, 1H), 7.05 (d, J=9 Hz, 2H), 7.11 (d, J=2 Hz, 1H), 7.34 (d, J=8 Hz, 1H), 7.54 (d, J=9 Hz, 1H), 7.79 (d, J=17 Hz, 1H), 7.81 (d, J=2 Hz, 1H), 7.96 (d, J=17 Hz, 1H), 7.99 (d, J=9 Hz, 2H), 8.19 (d, J=2 Hz, 1H), 10.18 (s, 1H): MS (ESI) [M–H]$^-$ at m/z 647

EXAMPLE 39b

5-[[4-(Methylsulfonyl)benzoyl]-2-[(E)-2-[4-[amino]-
2-sulfophenyl]ethenyl]benzenesulfonic Acid The bis(tetra-N-butyl)ammonium salt was prepared according to the procedure for Example 40a except using commercially available 4-(methylsulfonyl)-benzoic acid in place of of 4-methoxyethoxybenzoic acid (35%): $^1$HNMR (DMSO-d$_6$) δ0.85 (m, 24H), 1.35 (m, 16H), 1.48 (m, 16H), 3.20 (m, 16H), 3.30 (s, 3H), 5.29 (s, 2H), 6.72 (dd, J=8, 2 Hz, 1H), 7.13 (d, J=2 Hz, 1H), 7.36 (d, J=8 Hz, 1H), 7.55 (d, J=8 Hz, 1H), 7.79 (dd, J=8, 8, 1H), 7.87 (s, 1H), 7.99 (s, 1H), 8.04 (m, 1H), 8.07 (s, 1H), 8.09 (m, 1H), 8.19 (d, J=2 Hz, 1H), 8.21 (d, J=8 Hz, 2H), 10.60 (s, 1H): MS (ESI) [M–H]$^-$ at m/z 551.

EXAMPLE 40a

5-[[4-(2-Methoxyethoxy)benzoyl]amino]-2-[(E)-2-[4-[[4-(methanesulfonyl)benzoyl]amino]-2-sulfophenyl]ethenyl]benzenesulfonic Acid Oxalyl chloride (0.5 mL) and DMF (1 drop) were added to a 0° C., stirred solution of commercially available 4-(methylsulfonyl)-benzoic acid (97 mg, 0.5 mmol) dichloromethane (10 mL). Concentration in vacuum afforded an off white powder. A solution of this powder in dichloromethane (5 mL) was added to a 0° C., stirred solution of bis(tetra-N-butyl)ammonium salt of 5-amino-2-[(E)-2-(4-{[4-(2-methoxyethoxy)benzoyl]amino}-2-sulfophenyl) ethenyl]-benzenesulfonic acid (Example 39a, 0.50 g, 0.5 mmol) and triethylamine (0.14 g, 1.0 mmol) indichloromethane (25 mL). The resulting yellow mixture was allowed to warm to room temperature and was stirred for 20 hours. Water (15 mL) was added and the layers were separated. The organic phase was dried ($MgSO_4$) and concentrated to provide a yellow powder that was chromatographed (gradient elution MeOH:$CH_2Cl_2$) to afford bis (tetra-N-butyl)ammonium salt of the title compound as a yellow foam (280 mg). A solution of this yellow foam in water:methanol/90:10 (300 mL) was passed through a sodium ion exchange resin (300 g, Toyopearl SP-650 resin). The fractions were combined and concentrated to about 20 mL. This concentrate was subjected to freeze drying which afforded the bis(sodium) salt of the title compound as a yellow powder (146 mg, 43% yield): $^1$HNMR (DMSO-$d_6$) δ3.35 (s, 3H), 3.39 (s, 3H), 3.70 (t, J=5 Hz, 2H), 4.20 (t, J=5 Hz, 2H), 7.05 (d, J=14 Hz, 2H), 7.60 (t, 9 Hz, 2H), 7.88 (dt, J=17, 2 Hz, 2H), 7.98 (d, J=18 Hz, 2H), 8.04 (dd, J=1 Hz, 2H), 8.04 (d, J=11 Hz, 2H), 8.19 (dd, 10, 2 Hz, 2H), 8.21 (d, 15 Hz, 2H), 10.26 (s, 1H), 10.68 (s, 1H): MS (ESI) [M–H]$^-$ at m/z 729.

EXAMPLE 40b

5-[[4-(Methylsulfonyl)benzoyl]amino]-2-[(E)-2-[4-[[4-[(methylsulfonyl)methyl]benzoyl]amino]-2-sulfophenyl]ethenyl]benzenesulfonic Acid The (bis(sodium) salt was prepared according to the procedure for Example 41a except using the bis(tetra-N-butyl)ammonium salt 5-[[4-(methylsulfonyl)benzoyl]-2-[(E)-2-[4-[amino]-2-sulfophenyl]ethenyl]benzenesulfonic acid, Example 39b, in place of 5-amino-2-[(E)-2-(4-{[4-(2-methoxyethoxy)benzoyl]amino}-2-sulfophenyl)ethenyl] benzenesulfonic acid and 4-methanesulfonylmethylbenzoic acid, Example 19, in place of 4-(methylsulfonyl)-benzoic acid (10%): $^1$HNMR (DMSO-$d_6$) δ2.86 (s, 3H), 3.21 (s, 2H), 3.30 (s, 3H), 7.48 (d, J=8 Hz, 2H), 7.52 (dd, J=8, 5 Hz, 2H), 7.79 (m, 2H), 7.93 (d, J=8 Hz, 2H), 7.98 (m, 4H), 8.13 (m, 4H), 10.30 (s, 1H), 10.60 (s, 1H): MS (ESI) [M–H]$^-$ at m/z 747.

EXAMPLE 41

5-Amino-2-[(E)-2-[4-[[4-(2-methoxyethoxy) benzoyl]amino]-2-sulfophenyl]ethenyl] benzenesulfonic Acid Oxalyl chloride (0.5 mL) and DMF (1 drop) were added to a 0° C., stirred solution of 4-methoxyethoxybenzoic acid (Example 16, 0.31 g, 1.56 mmol) in dichloromethane (6 mL) under a dry nitrogen atmosphere, and the yellow solution was stirred for 1 hr. Concentration in vacuum afforded an off white powder. A solution of this powder in dichloromethane (1 mL) was added to a 0° C., stirred solution of 2,2'-[(E)-1,2-ethenediyl]bis[5-aminobenzenesulfonic acid, bis(tetra-N-butylammonium) salt (Example 31, 1.28 g, 1.5 mmol) and triethylamine (210 mg, 2 mmol) in dichloromethane (20 ml) at 0° C. under a dry nitrogen atomosphere. The resulting suspension was stirred at 0° C. for 2 hours and at room temperature for an additional 18 hours. The reaction mixture was diluted with dichloromethane (200 ml), washed, dried and evaporated to give a pale foam. Chromatography of the foam on silica gel and elution with 6% methanol dichloromethane afforded the 550 mg (36% yield) of the bis(tetra-N-butyl)ammonium salt of the titile compound as a white foam: $^1$HNMR (DMSO-$d_6$) δ0.82 (m, 24H), 1.20 (m, 16H), 1.42 (m, 16H), 3.00 (m, 16H), 3.44 (s, 3H), 3.76 (m, 2H), 4.17 (m, 2H); Analytical HPLC: 76% purity; MS (ES-Neg): [M–H]$^-$ 547.

EXAMPLE 42

5-[[4-(2-Methoxyethoxy)benzoyl]amino]-2-[(E)-2-[4-[[4-methoxy-3-(4-morpholinylsulfonyl)benzoyl] amino]-2-sulfo-phenyl]ethenyl]benzenesulfonic Acid Oxalyl chloride (150 mg, 1.18 mmol) and DMF (2 drops) were added to a 0° C., stirred solution of 4-Methoxy-3-(morpholine-4-sulfonyl)-benzoic Acid (Example 1a, 300 mg, 1 mmol) in dichloromethane (3.5 mL) under a dry nitrogen atmosphere, and the yellow solution was stirred for 1 hr. Concentration in vacuum afforded an off white powder. A solution of this powder in dichloromethane (1.5 mL) was added to a 0° C., stirred solution of the bis(tetra-N-butyl) ammonium salt of 5-amino-2-[(E)-2-[4-[[4-(2-methoxyethoxy)benzoyl]amino]-2-sulfo-phenyl]ethenyl] benzenesulfonic acid (Example 41, 1.03 g, 1 mmol) and triethylamine (130 mg, 1.3 mmol) in dichloromethan (27 mL). The resulting suspension was stirred at 0° C. for 2 hours and at room temperature for an additional 18 hours. The suspension was treated with DMF (4 ml) and became a solution and was further stirred at room temperature/N for an additional 18 hours. The reaction mixture was diluted with methylene chloride (200 ml), washed, dried and evaporated. Chromatography of the crude product on silica gel and elution with 6% methanol in dichloromethane afforded 390 mg of the bis(tetra-N-butyl)ammonium salt of the title compound as a white foam. This foam (100 mg) was dissolved in methanol/deionized water (1/1) (8 ml) and poured into an ion exchange resin column (3×20 cm, Toyopearl SP-650C, size range 100 micron). Elution with 5% methanol in deionized water (450 ml) and freeze-drying the eluent afforded 64 mg (30%) of the bis(sodium) salt of the title compound as a white form: $^1$HNMR (DMSO-$d_6$) δ3.15 (t, 4H), 3.35 (s, 3H,), 3.60 (t, 4H), 3.71 (t, 2H), 4.01 (s, 3H), 4.20 (t, 2H); Analytical HPLC: 96.7% purity; MS (ES-Neg): [M–H]$^-$ 830.

EXAMPLE 43a

5-[[4-Methoxy-3-(4-morpholinylsulfonyl)benzoyl] amino]-2-[2-[4-[[4-(methylsulfonyl)benzoyl]amino]-2-sulfophenyl]ethyl]benzenesulfonic Acid 5-[[4-Methoxy-3-(4-morpholinylsulfonyl)benzoyl] amino]-2-[(E)-2-[4-[[4-(methylsulfonyl)benzoyl]amino]-2-sulfophenyl]ethenyl]benzenesulfonic acid] (Example 30 g, 0.06 g, 0.068 mmol) was dissolved in 10:1 methanol/water (28 mL) under a nitrogen atmosphere. To the clear solution was added (10%) palladium on carbon (0.015 g, 0.014 mmol) and the flask repurged with nitrogen three times. A hydrogen filled balloon was attached and the flask evacuated and allowed to fill with hydrogen. After stirring overnight TLC showed no starting material remained. The flask was purged with nitrogen and then filtered thru Celite. The solids were washed with methanol and then the combined liquids concentrated to dryness 43 mg (72%) of the title compound as an off-white solid: $^1$NMR (DMSO-$d_6$) δ11.40 (s, 1H), 10.36 (s, 1H), 8.40 (d, J=2 Hz, 1H), 8.35 (dd, J=2 Hz, 9 Hz, 1H), 8.22 (d, J=8 Hz, 2H), 8.12 (d, J=2 Hz, 1H), 8.07 (m, 3H), 7.75 (d, J=8 Hz, 2H), 7.41(d, J=9 Hz, 1H), 7.29 (m, 2H), 3.99(s, 3H), 3.61 (m, 4H), 3.30 (m, 7H), 3.13 (m, 4H); MS (ES-NEG): [M−H] 836; Anal. Calc. for $C_{34}H_{33}N_3O_{14}S_4Na_2 \cdot 7H_2O$: C, 40.51; H, 4.70; N, 4.16. Found: C, 40.68; H, 3.68; N, 4.07.

By a procedure analogous to Example 43a, but using a different stilbene derivative in place of 5-[[4-methoxy-3-(4-morpholinylsulfonyl)benzoyl]amino]-2-[(E)-2-[4-[[4-(methylsulfonyl)benzoyl]amino]-2-sulfophenyl]ethenyl] benzenesulfonic acid], the following compounds in Examples 43b to 443h were prepared.

EXAMPLE 43b 2,2'-(1,2-Ethanediyl)bis[5-[[4-methoxy-3-(1-piperidinylsulfonyl)benzoyl]amino]benzenesulfonic Acid The bis(sodium) salt prepared from the bi(sodium) salt of 2,2'-[(E)-1,2-ethenediyl]bis[5-[[4-methoxy-3-(1-piperidinylsulfonyl)benzoyl]amino]benzenesulfonic acid], Example 30h (25%): MS (ES-NEG): [M−H] 933.

EXAMPLE 43c 2,2'-(1,2-Ethanediyl)bis[5-[[3-[(1,1-dioxido-4-thiomorpholinyl)sulfonyl]-4-methoxybenzoyl] amino]benzenesulfonic Acid]

The bis(sodium) salt prepared from the bi(sodium) salt of 2,2'-[(E)-1,2-ethenediyl]bis[5-[[3-[(1,1-dioxido-4-thiomorpholinylsulfonyl]-4-methoxybenzoyl]amino] benzenesulfonic acid], Example 30k (75%): MS (ES-NEG): [M−H] 1033.

EXAMPLE 43d 2,2'-(1,2-Ethanediyl)bis[5-[[3-(4-morpholinylsulfonyl)benzoyl]amino] benzenesulfonic Acid The bis(sodium) salt prepared from the bi(sodium) salt of 2,2'-[(E)-1,2-ethenediyl]bis[5-[[3-(4-morpholinylsulfonyl) benzoyl]amino]benzenesulfonic acid], Example 34a (46%): MS-ESI: [M−H]⁻ 877.

EXAMPLE 43e 2,2'-(1,2-Ethanediyl)bis[5-[[4-methylsulfonyl) benzoyl]amino]benzenesulfonic Acid]

The bis(sodium) salt prepared from the bi(sodium) salt of 2,2'-[(E)-1,2-ethenediyl]bis[5-[[4-(methylsulfonyl)benzoyl] amino]benzenesulfonic acid], Example 30q (85%): MS (ES-NEG): [M−H] 735.

EXAMPLE 43f 2,2'-(1,2-Ethanediyl)bis[5-[[4-(2-methoxyethoxy)-3-(4-morpholinylsulfony)benzoyl]amino] benzenesulfonc Acid]

The bis(sodium) salt prepared from the bi(sodium) salt of 2,2'-[(E)-1,2-ethenediyl]bis[5-[[4-(2-methoxyethoxy)-3-(4-morpholinylsulfony)benzoyl]amino]benzenesulfonic acid], Example 30t (66%): MS (ES-NEG): [M−H] 1025.

EXAMPLE 43g 2,2'-(1,2-Ethanediyl)bis[5-[[4-methoxy-3-(1-pyrrolidinylsulfonyl)benzoyl]amino]benzenesulfonic Acid]

The bis(sodium) salt prepared from the bi(sodium) salt of 2,2'-[(E)-1,2-ethenediyl]bis[5-[[4-methoxy-3-(1-pyrrolidinylsulfonyl)benzoyl]amino]benzenesulfonic acid], Example 34e (15%): MS (ES-NEG): [M−H] 905.

EXAMPLE 43h

5-[[4-(2-Methoxyethoxy)benzoyl]amino]-2-[2-[4-[[4-methoxy-3-(4-morpholinylsulfonyl)benzoyl] amino]-2-sulfophenyl]ethyl]benzenesulfonic Acid The bis(sodium) salt prepared from the bi(sodium) salt of 5-[[4-(2-methoxyethoxy)benzoyl]amino]-2-[(E)-2-[4-[[4-methoxy-3-(4-morpholinylsulfonyl)benzoyl]amino]-2-sulfo-phenyl]ethenyl]benzenesulfonic acid, Example 42 (86%): MS (ES-Neg): [M−H]⁻ 832.

EXAMPLE 44

2-Bromomethyl-5-nitro-benzenesulfonic Acid, 2,2-Dimethylpropyl Ester

To a solution of 2-methyl-5-nitro-benzenesulfonic acid, 2,2-dimethylpropyl ester, Example 24 (1.0 g, 3.48 mmol) in dry carbon tetrachloride (50 mL) was added 126 mg (0.52 mmol) of benzoyl peroxide and 712 mg (4.0 mmol) of recrystallized N-bromosuccinimide. A reflux condensor was attached and the mixture was heated to reflux and stirred overnight. After cooling to room temperature the reaction mixture was diluted with ethyl acetate (250 mL) and washed with water, followed by saturated sodium bicarbonate, and then brine. The organic layer was dried ($MgSO_4$) and concentrated to dryness on a rotary evaporator. Purification by flash column chromatography using 10% ethyl acetate in hexanes gave 560 mg (44%) of the title compound as a white solid: $^1$HNMR ($CDCl_3$): d 8.83 (d, J=2 Hz, 1H), 8.48 (dd, J=2 Hz, 9 Hz, 1H), 7.92 (d, J=9 Hz, 1H), 4.96 (s, 2H), 3.85 (s, 2H), 1.0 (s, 9H); MS (ES-NEG): [M−H] 364/366; Anal. Calc. for $C_{12}H_{16}BrNO_5S$: C, 39.35; H, 4.40; N, 3.82. Found: C, 39.88; H, 4.16; N, 3.85.

EXAMPLE 45

2-Methanethiol-5-nitro-benzenesulfonic Acid, 2,2-Dimethylpropyl Ester

2-Bromomethyl-5-nitro-benzenesulfonic Acid, 2,2-dimethylpropyl ester (Example 44, 2.0 g, 5.46 mmol) was dissolved in chloroform (100 mL) under a nitrogen atmosphere. Thioacetamide (431 mg, 5.73 mmol) was added and a condensor attached. The mixture was then heated to reflux overnight. After cooling to room temperature the solution was filtered and the precipitate washed with chloroform. The combined organic solution was washed with water followed by brine. The organic layer was then dried ($MgSO_4$) and concentrated on a rotary evaporator to yield 2 g (100%) of the title compound as a yellow oil: $^1$HNMR ($CDCl_3$) δ8.80 (d, J=2 Hz, 1H), 8.49 (dd, J=2 Hz, 9 Hz, 1H), 7.84 (d, J=9 Hz, 1H), 4.17 (d, J=9 Hz, 2H), 3.81 (s, 2H), 2.28 (t, J=9 Hz, 1H), 0.97 (s, 9H).

EXAMPLE 46

2,2'-[Thiobis(methylene)]bis[5-nitrobenzenesulfonic Acid], Dimethylpropyl Ester

2-Methanethiol-5-nitro-benzenesulfonic acid, 2,2-dimethylpropyl ester (Example 45, 1.74 g, 5.45 mmol) was dissolved in 55 mL of anhydrous acetonitrile under a nitrogen atmosphere. To the stirring solution was 2-bromomethyl-5-nitro-benzenesulfonic acid, 2,2-dimethylpropyl ester (Example 44, 2.19 g, 5.99 mmol) followed by triethylamine (1.14 mL, 8.17 mmol) and the mixture stirred for six hours. The mixture was concentrated to a small volume on a rotary evaporator and then diluted with ethyl acetate (200 mL). The organic layer was washed with 1 N hydrochloric acid followed by brine and then dried ($MgSO_4$). After concentration on a rotary evaporator the crude material was purified by flash column chromatography using a 10 to 20% gradient of ethyl acetate in hexanes to yield 1.2 g (36%) of the title compound as a yellow-orange solid: $^1$HNMR ($CDCl_3$) δ8.83 (d, J=2 Hz, 2H), 8.45 (dd, J=2 Hz, 9 Hz, 2H), 7.96 (d, J=9 Hz, 2H), 4.26 (s, 4H), 3.77 (s, 4H), 0.93 (s, 18H); MS (APCI+): [M+$NH_4$] 622; Anal.Calc. for $C_{24}H_{32}N_2O_{10}S_3$: C,47.67; H,5.33; N,4.63. Found: C,47.39; H,5.05; N,4.45.

EXAMPLE 47

2,2'-[Thiobis(methylene)]bis[5-aminobenzenesulfonic Acid], Dimethylpropyl Ester 2,2'-[Thiobis(methylene)]bis[5-nitrobenzenesulfonic acid], dimethylpropyl ester (Example 46, 1.2 g, 1.98 mmol) was dissolved in 40 mL ethanol under a nitrogen atmosphere. A condensor was attached and tin chloride dihydrate (2.24 g, 9.92 mmol) was added. The mixture was heated to reflux and after six hours cooled to room temperature. The solution was diluted with ethyl acetate (400 mL) and washed with saturated sodium bicarbonate. A large amount of white precipitate formed and the mixture was filtered thru Celite. The aqueous layer was discarded and the organics washed with brine and then dried ($MgSO_4$). After concentrating on a rotary evaporator the crude material was purified by flash column chromatography using 5% methanol in dichloromethane as the eluant to yield 710 mg (66%) of the title compound as an orange solid: $^1$HNMR (DMSO-$d_6$) δ7.28 (d, J=8 Hz, 2H), 7.12 (d, J=2 Hz, 2H), 6.81 (dd, J=2 Hz, 8 Hz, 2H), 5.70 (br s, 4H), 3.94 (s, 4H), 3.61 (s, 4H), 0.85 (s, 18H); MS (ES-POS): [M+H] 545; Anal.Calc. for $C_{24}H_{36}N_2O_6S_3$-0.6 $H_2O$: C,51.89; H,6.75; N,5.04. Found: C,51.70; H,6.47; N,4.91.

EXAMPLE 48

2,2'-]Thiobis(methylene)]bis[5-[[4-methoxy-3-(-4-morpholinylsulfonyl)benzoyl]amino] benzenesulfonic Acid], Dimethylpropyl Ester 4-Methoxy-3-(morpholine-4-sulfonyl)-benzoic acid (Example la, 426 mg, 1.41 mmol) was dissolved in dichloromethane under a nitrogen atmosphere. Three drops of dry dimethylformamide were added and the mixture cooled to zero degrees in an ice water bath. Oxalyl chloride (0.140 mL, 1.61 mmol) was added dropwise and the mixture stirred as it gradually warmed to room temperature. After two hours the mixture was concentrated to dryness on a rotary evaporator. The residue was dissolved in dry THF (10 mL) and added to a suspension of 2,2'-[thiobis(methylene)]bis[5-aminobenzenesulfonic acid], dimethylpropyl ester (Example 47, 350 mg, 0.64 nmmol) and potassium carbonate (355 mg, 2.57 mmol) in 40 mrL of dry tetrahydrofuran under a nitrogen atmosphere. The mixture was allowed to stir overnight and was then concentrated to a small volume. Ethyl acetate (200 mL) was added and the organic layer washed with saturated sodium bicarbonate followed by brine. The organic layer was the dried ($MgSO_4$) and concentrated. The crude material was purified by flash column chromatography using 5% methanol in dichloromethane as the eluant to yield 340 mg (50%) of the title compound as a yellow solid: $^1$HNMR ($CDCl_3$) δ8.47 (s, 2H), 8.31 (d, J=2 Hz, 2H), 8.19 (d, J=2 Hz, 2H), 8.08 (dd, J=2Hz, 9 Hz, 2H), 7.76 (dd, J=2Hz, 9 Hz, 2H), 7.51 (d, J=9 Hz, 2H), 7.09 (d, J=9 Hz, 2H), 4.23 (s, 4H), 3.98 (s, 6H), 3.73 (m, 12H), 3.27 (m, 8H), 0.95 (s, 18H); MS (ES-NEG): [M–H] 1109; Anal.Calc. for $C_{48}H_{62}N_4O_{16}S_5$: C,51.88; H,5.62; N,5.04. Found: C,51.97; H,5.94; N,5.14.

EXAMPLE 49

2,2'-[Sulfonylbis(methylene)]bis[5-[[4-methoxy-3-(4-morpholinylsulfonyl)benzoyl]amino] benzenesulfonic Acid], Dimethylpropyl Ester 2,2'-[Thiobis(methylene)]bis[5-[[4-methoxy-3-(-4-morpholinylsulfonyl)benzoyl]amino]benzenesulfonic acid], dimethylpropyl ester (Example 48, 190 mg, 0.17 mmol) was dissolved in dichloromethane (15 mL) under a nitrogen atmosphere. 3-Chloroperoxybenzoic acid (278 mg, 0.85 mmol) was added and the mixture was stirred overnight. The solution was diluted with dichloromethane (200 mL) and washed with saturated sodium bicarbonate followed by brine. The organic layer was dried ($MgSO_4$) and concentrated to dryness on a rotary evaporator. The crude product was purified by gradient flash column chromatography using 50 to 70% ethyl acetate in dichloromethane to yield 100 mg (52%) of the title compound as a white solid: $^1$HNMR ($CDCl_3$) δ9.20 (s, 2H), 8.42 (d, J=1.5 Hz, 2H), 8.37 (d, J=1.5 Hz, 2H), 8.09 (dd, J=1.5 Hz, 9 Hz, 2H), 8.04 (dd, J=1.5 Hz, 9 Hz, 2H), 7.72 (d, J=9 Hz, 2H), 7.01 (d, J=9 Hz, 2H), 4.85 (s, 4H), 3.90 (s, 6H), 3.69 (m, 12H), 3.23 (br s, 8H), 0.90 (s, 18H); MS (FI-NEG): [M–H] 1141.

EXAMPLE 50a 2,2'-[Thiobis(methylene)]bis[5-[[4-methoxy-3-(4-morpholinylsulfonyl)benzoyl]amino] benzenesulfonic Acid]

2,2'-[Thiobis(methylene)]bis[5-[[4-methoxy-3-(-4-morpholinylsulfonyl)benzoyl]amino]benzenesulfonic acid], dimethylpropyl ester (Example 48, 75 mg, 0.067 mmol) was dissolved in dry dimethylformamide (10 mL) under a nitrogen atmosphere. Tetramethylammonium chloride (44 mg, 0.40 mmol) was added and the mixture heated to 100 C. and stirred for three days until no starting material remained. The mixture was cooled to 0 C. and filtered to remove excess tetramethylammonium chloride and then concentrated on a rotary evaporator. The crude material was passed thru an ion-exchange column (Toyopearl TSK SP-650 C) using 5% methanol in water as the eluant to generate the sodium salt. This material was further purified by HPLC [C18, acetonitrile:water (0.1% trifluoroacetic acid) 10 to 100%] and freeze dried to give 7 mg (11%) of the title compound as a brown solid: $^1$HNMR (DMSO-$d_6$) δ10.45 (s, 2H), 8.40 (d, J=2 Hz, 2H), 8.34 (d, J=9 Hz, 2H), 8.13 (br s, 2H), 7.83 (m, 1H), 7.41 (d, J=9 Hz, 2H), 7.31 (d, J=8 Hz, 2H), 4.00 (s, 6H), 3.61 (m, 8H), 3.12 (m, 8H); MS (ES-NEG): [M–H]$^-$ 969.

EXAMPLE 50b 2,2'-[Sulfonylbis(methylene)]bis[5-[[4-methoxy-3-(4-morpholinylsulfonyl)benzoyl]amino] benzenesulfonic acid]

The title compound was prepared as a white solid according to the procedure for Example 50a except using 2,2'-

[sulfonylbis(methylene)]bis[5-[[4-methoxy-3-(4-morpholinylsulfonyl)benzoyl]amino]benzenesulfonic acid], dimethylpropyl ester, Example 49 (27%): $^1$HNMR (DMSO-d$_6$) δ10.49 (s, 2H), 8.40 (d, J=2 Hz, 2H), 8.34 (d, J=9 Hz, 2H), 8.15 (m, 1H), 7.82 (d, J=8 Hz, 2H), 7.41 (d, J=9 Hz, 2H), 7.25 (d, J=8 Hz, 2H), 5.02 (s, 4H), 3.99 (s, 6H), 3.61 (m, 8H), 3.12 (m, 8H); MS (ESI–NEG): [M–H]$^-$ 1001; Anal. Calc. for $C_{38}H_{42}N_4O_{18}S_5$-8.5H$_2$O: C,39.47; H,5.14; N,4.85. Found: C,39.38; H,4.89; N,4.98.

EXAMPLE 51

2-Methyl-5-nitrobenzene Sulfonamide

In a round bottom flask under nitrogen was placed commercially available 2-methyl-5-nitrobenzene sulphonyl chloride (2.36 g, 10.0 mmol) and 75 L dry ethyl ether was added. The solution was cooled to 0° C. and concentrated ammonium hydroxide (10 mL) was added. After stirring overnight, the mixture was filtered and then diluted with dichloromethane (150 mL). The organic layer was separated and dried over MgSO$_4$. The solution was then concentrated to afford 820 mg of the title compound as a white solid (38%): $^1$HNMR (DMSO-d$_6$) δ8.61 (d, J=2.5 Hz, 1H), 8.35 (dd, J=8 Hz, 2.5 Hz, 1H), 7.79 (br s, 2H), 7.70 (d, J=8 Hz, 1H), 2.71 (s, 3H).

EXAMPLE 52

5-Nitro-2-[(E)-2-(4-nitro-2-(aminosulfonyl)phenyl)ethenyl]benzenesulfonamide In a round bottom flask under nitrogen was placed 2-methyl-5-nitrobenzene sulfonamide (Example 51, 0.72 g, 3.33 mmol) and 30 mL of anhydrous dimethylformamide. To this mixture was added potassium t-butoxide (1.12 g, 9.99 mmol) and the solution turned a deep red color. The mixture was allowed to stir for 16 hours and was then poured over ice (50 g). The orange-brown mixture was diluted with ethyl acetate (150 mL), the organic layer separated, and dried over MgSO$_4$. The material was then concentrated and dried under vacuum to afford 300 mg of the title compound as an orange solid (21%): $^1$HNMR (DMSO-d$_6$) δ8.70 (d, J=2 Hz, 2H), 8.55 (dd, J=9 Hz, 2 Hz, 2H), 8.20 (d, J=9 Hz, 2H), 8.09 (s, 2H), 8.06 (s, 4H); MS (FI–NEG): [M–H]– 427.

EXAMPLE 53

5-Amino-2-[(E)-2-(4-amino-2-(aminosulfonyl)phenyl)ethenyl]benzenesulfonamide In a round bottom flask under nitrogen was placed 5-nNitro-2-[(E)-2-(4-nitro-2-(aminosulfonyl)phenyl)ethenyl]benzenesulfonamide (Example 51, 0.38 g, 0.887 mmol) and 40 mL of ethyl acetate added. To this mixture was added tin chloride dihydrate (1.00 g, 4.44 mmol) and a reflux condenser was attached. The solution was heated in an oil bath to 80 C. and stirred for 16 hours. After cooling to room temperature the solution was diluted with ethyl acetate (250 mL) and washed with saturated sodium bicarbonate. The whole mixture was filtered thru Celite and the aqueous layer discarded. The organics were then washed with brine, dried (MgSO$_4$) and concentrated on a rotovap to dryness. The crude material was then recrystallized from 10% methanol/dichloromethane and dried under vacuum to afford 100 mg of the title compound as a dark yellow solid (31%): $^1$HNMR (DMSO-d$_6$) δ7.58 (d, J=8.5 Hz, 2H), 7.49 (s, 2H), 7.31 (br s, 4H), 7.15 (d, J=2 Hz, 2H), 6.75 (dd, J=8.5 Hz, 2 Hz, 2H), 5.65 (br s, 4H).

EXAMPLE 54

N-[3-(Aminosulfonyl)-4-[(E)-2-[2-(aminosulfonyl-4-[[4-(methylsulfanyl)-3-(4-morpholinyl-sulfonyl)benzoyl]amino]phenyl]ethenyl]phenyl]-4-(methylsulfanyl)-3-(4-morpholinylsulfonyl)benzamide To a solution of 4-methylsulfanyl-3-(morpholino-4-sulfonyl)-benzoic acid (Example 3, 0.198 g, 0.612 mmol) in 27 mL of dry dichloromethane under nitrogen was added dimethylformamide (50 μL) and the solution cooled to zero degrees in an ice water bath. At this time oxalyl chloride (0.063 mL, 0.675 mmol) was added and the mixture stirred for 30 minutes and then allowed to warm to room temperature. After 3 hours total the mixture was concentrated to dryness and then redissolved in 45 mL of dry THF. This solution was added to a suspension of 5-amino-2-[(E)-2-(4-amino-2-(aminosulfonyl)phenyl)ethenyl]benzenesulfonamide (Example 53, 0.09 g, 0.244 mmol) and potassium carbonate (0.135 g, 0.972 mmol in 45 mL of dry THF under notrogen and the reaction mixture was stirred overnight. The reaction mixture was then diluted with ethyl acetate (300 mL) and washed with saturated sodium bicarbonate. A precipitate formed at the interface and was collected by filtration. After washing with ethyl acetate, this precioitate was dried under vacuum to afford 87 mg of the title compound as a yellow solid (37%): $^1$HNMR (DMSO-d$_6$) δ10.80 (br s, 2H), 8.46 (s, 2H), 8.43 (s, 2H), 8.28 (d, J=7 Hz, 2H), 8.10 (d, J=8 Hz, 2H), 7.99 (d, J=9 Hz, 2H), 7.85 (s, 2H), 7.67 (d, J=9 Hz, 2H), 7.60 (br s, 4H), 3.62 (m, 8H), 3.15 (m, 8H), 2.61 (s, 6H); MS (ES–NEG): [M–H]– 965; Anal. .Calc. for $C_{38}H_{42}N_6O_{12}S_6$-4H$_2$O: C, 43.92; H, 4.85; N, 8.09. Found: C, 43.79; H, 4.29; N, 8.04.

EXAMPLE 55

2-(Diethoxyphosphorylmethyl)-5-nitro-benzenesulfonic Acid, 2,2-Dimethylpropyl Ester 2-Bromomethyl-5-nitro-benzenesulfonic acid, 2,2-dimethylpropyl ester (Example 44, 2.0 g, 5.46 mmol) was dissolved in 100 mnL of anhydrous o-xylene. To this solution was added triethylphosphite (3.75 mL, 21.84 mmol). A water cooled condenser was attached and the material was heated to exactly 100° C. After six hours the mixture was cooled to room temperature then diluted with with ethyl acetate (400 mL) and washed with brine (2×). After drying over MgSO$_4$ the organic layer was concentrated on a rotovap and then purified by flash column chromatography using 50 to 60% ethyl acetate/hexanes gradient as an eluant to provide 1.34 g of the title compound as a yellow oil.(55%): $^1$HNMR (CDCl$_3$) δ8.87 (m, 1H), 8.43 (dd, J=9 Hz, 2 Hz, 1H), 8.05 (dd, J=9 Hz, 2 Hz, 1H), 4.12 (m, 4H), 3.81 (s, 2H), 3.77 (d, J=23 Hz, 2H), 1.32 (m, 6H), 0.96 (s, 9H); MS (ES-POS): [M+Na]+ 446; Analytical HPLC determined that this compound was 96.1% pure by C-18 reverse phase.

EXAMPLE 56

5-Nitro-2-[2-(4-nitro-phenyl)-vinyl]-benzenesulfonic Acid 2,2-Dimethylpropyl Ester 2-(Diethoxyphosphorylmethyl)-5-nitro-benzenesulfonic acid, 2,2-dimethylpropyl ester Example 55, 1.15 g, 2.72 mmol) was dissolved in 55 mL of anhydrous tetrahydrofuran. Sodium hydride (0.12 g, 2.99 mmol) was added in one portion and the reaction mixture was stirred for twenty minutes. The solution turned a deep red color. After attaching a reflux condenser, 4-nitrobenzaldehyde (0.821 g, 5.43 mmol) was added and the mixture was heated to reflux in an oil bath. After six hours the solution was cooled to room temperature, diluted with ethyl acetate (300 mL), washed with brine (2×), washed with conc. sodium bisulfite (2×), and the organic layer was dried (MgSO$_4$). After concentration on a rotovap the crude material was purified by a gradient flash column using 30 to 60% ethyl acetate in hexanes as the eluant to afford 1.13 g of the title compound as a yellow solid (91%): $^1$HNMR (CDCl$_3$) δ8.91 (d, J=2 Hz, 1H), 8.51 (dd, J=9 Hz, 2 Hz, 1H), 8.29 (d, J=9 Hz, 2H), 8.09 (d, J=16 Hz, 1H), 8.06 (d, J=9Hz, 1H), 7.74 (d, J=9Hz, 2H), 7.31 (d, J=16 Hz, 1H), 3.75 (s, 2H), 0.88 (s, 9H); MS (ES-NEG): [M−H]− 419; Anal. Calc. for C$_{19}$H$_{20}$N$_2$O$_7$S: C, 54.28; H, 4.79; N, 6.66. Found: C, 54.13; H, 4.68; N, 6.54.

EXAMPLE 57

5-Amino-2-[2-(4-amino-phenyl)-vinyl]-benzenesulfonic Acid, 2,2-Dimethylpropyl Ester 5-Nitro-2-[2-(4-nitro-phenyl)-vinyl]-benzenesulfonic acid 2,2-dimethylpropyl ester (Example 56, 1.10 g, 2.62 mmol) was dissolved in 52 mL of ethyl acetate. Tin chloride dihydrate (2.95 g, 13.1 mmol) was added and a reflux condenser attached. The solution was heated to reflux and stirred overnight. After cooling to room temperature the solution was diluted with ethyl acetate (300 mL) and washed with saturated sodium bicarbonate. The whole mixture was filtered thru Celite and the aqueous layer discarded. The organic layer was then washed with brine and dried over MgSO$_4$. After concentration on a rotovap the crude material was purified by a gradient flash column using 3 to 10% ethyl acetate in dichloromethane as the eluant to afford 0.33 g of the title compound as a oily red solid (35%): $^1$HNMR (CDCl$_3$): δ7.63 (d, J=9 Hz, 1H), 7.58 (d, J=16 Hz, 1H), 7.33 (d, J=9 Hz, 2H), 7.31 (d, J=3 Hz, 1H), 6.89 (dd, J=9 Hz, 3 Hz, 1H), 6.86 (d, J=16 Hz, 1H), 6.68 (d, J=9 Hz, 2H), 3.89 (br s, 4H), 3.61 (s, 2H), 0.86 (s, 9H); MS (ES-POS): [M+H]+ 361; Analytical HPLC determined that this compound was 90% pure by C-18 reverse phase.

EXAMPLE 58

5-[4-Methylsulfanyl-3-(morpholine-4-sulfonyl)-benzoylamino]-2-(2-{[4-methylsulfanyl-3-(morpholine-4-sulfonyl)-benzoylamino]-phenyl}-vinyl)-benzenesulfonic Acid, 2,2-Dimethylpropyl Ester To a solution of 4-methylsulfanyl-3-(morpholino-4-sulfonyl)-benzoic acid (Example 3, 0.60 g, 1.89 mmol) in 20 mL of anhydrous dichloromethane under nitrogen was added dimethylformamide (50 µl) and the solution was cooled to zero degrees in an ice water bath. At this time oxalyl chloride (0.182 mL, 2.08 mmol) was added and the mixture was stirred for 30 minutes and then allowed to warm to room temperature. After 3 hours total the mixture was concentrated to dryness and then redissolved in 20 mL of dry tetrahydrofuran. This solution was added to a suspension of 5-amino-2-[2-(4-amino-phenyl)-vinyl]-benzenesulfonic acid, 2,2-dimethylpropyl ester (Example 57, 0.31 g, 0.86 mmol) and potassium carbonate (0.594 g, 4.30 mmol) in 20 mL of dry THF. The resulting mixture was stirred overnight under nitrogen. The solution was then concentrated to a small volume on a rotovap and diluted with ethyl acetate (300 mL). After washing with water and brine the organic layer was dried (MgSO$_4$) and concentrated. Purification by a gradient flash column using 20 to 35% ethyl acetate in dichloromethane afforded 0.50 g of the title compound as an off-white solid (61%): HNMR (DMSO-d$_6$) δ10.86 (s, 1H), 10.59 (s, 1H), 8.52 (d, J=2 Hz, 1H), 8.43 (d, J=2 Hz, 1H), 8.39 (d, J=2 Hz, 1H), 8.28–8.22 (m, 3H), 8.14 (d, J=9 Hz, 1H), 7.85 (d, J=9 Hz, 2H), 7.72–7.65 (m, 3H), 7.57 (d, J=9 Hz, 2H), 7.37 (d, J=16 Hz, 1H), 3.70 (s, 2H), 3.62 (m, 8H), 3.15 (m, 8H), 2.62 (s, 3H), 2.61 (s, 3H), 0.83 (s, 9H); MS (ES-NEG): [M−H]− 957; Anal. Calc. for C$_{43}$H$_{50}$N$_4$O$_{11}$S$_5$-0.5H$_2$O: C, 53.34; H, 5.31; N, 5.79. Found: C, 53.26; H, 5.12; N, 5.57.

EXAMPLE 59

5-[4-Methylsulfanyl-3-(morpholine-4-sulfonyl)-benzoylamino]-2-(2-{[4-methylsulfanyl-3-(morpholine-4-sulfonyl)-benzoylamino]-phenyl}-vinyl)-benzenesulfonic Acid To a solution of 5-[4-methylsulfanyl-3-(morpholine-4-sulfonyl)-benzoylamino]-2-(2-{[4-methylsulfanyl-3-(morpholine-4-sulfonyl)-benzoylamino]-phenyl}-vinyl)-benzenesulfonic acid, 2,2-dimethylpropyl ester (Example 58, 0.30 g, 0.31 mimol) in 10 mL of anhydrous dimethylformamide was added tetramethylammonium chloride (0.069 g, 0.62 mmol) and the solution purged with nitrogen. The mixture was then heated to 100° C. and its progress followed by analytical reverse phase HPLC. After two days no starting material remained and the reaction was cooled to room temperature. After filtering to remove excess tetramethylammonium chloride the mixture was concentrated to dryness and the purified using reverse phase HPLC (70% THF/water) as the eluant. Freeze drying overnight afforded 120 mg of the title compound as a yellow solid.(43%): $^1$HNMR (DMSO-d$_6$) δ10.59 (s, 1H), 10.54 (s, 1H), 8.41 (dd, J=7 Hz, 2 Hz, 2H), 8.27 (m, 2H), 8.19 (d, J=16 Hz, 1H), 8.13 (d, J=2 Hz, 1H), 7.99 (dd, J=9 Hz, 2 Hz, 1H), 7.82 (d, J=8.5 Hz, 2), 7.79 (d J=7 Hz, 1H), 7.65 (dd, J=9 Hz, 2 Hz, 2H), 7.51 (d, J=8.5 Hz, 2H), 7.08 (d, J=16 Hz, 1H), 3.61 (m, 8H), 3.15 (m, 8H), 2.60 (s, 6H); MS (ES-NEG): [M−H]− 887; Anal. Calc. for C$_{38}$H$_{40}$N$_4$O$_{11}$S$_5$-2.2H$_2$O: C, 49.14; H, 4.82; N, 6.03. Found: C, 49.17; H, 5.07; N, 5.04. Analytical reverse phase HPLC shows compound is >90% pure.

What is claimed is:

1. A method of providing contraception in a female mammal in need thereof which comprises administering to said mammal a contraceptive effective amount of a compound of formula I having the structure

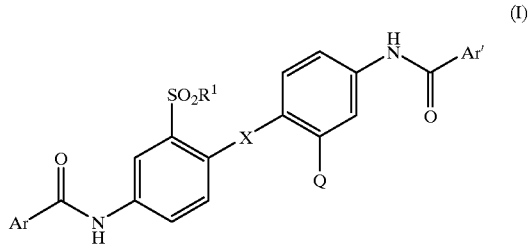

(I)

wherein

Q is hydrogen or —SO$_2$R$^1$;

X is a bond, O, S(O)$_n$, —CH═CH—, —CH$_2$CH$_2$—, CH—, —C≡C—, or —CH$_2$S(O)$_n$CH$_2$—;

R$^1$ is OH, NH$_2$, C$_1$ to C$_6$ alkoxy, C$_1$ to C$_3$ perfluoroalkoxy;

Ar is 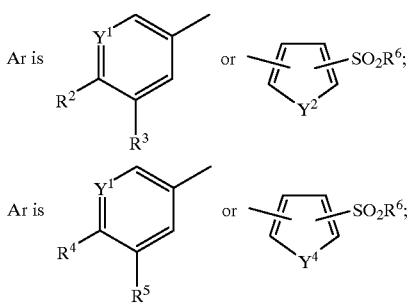

$R^2$ and $R^4$ are each, independently, hydrogen, $OR^6$, $-S(O)_mR^6$, $-NHR^6$, $-N(R^6)_2$, or $-CH_2SO_2CH_3$;
$R^3$ and $R^5$ are each, independently, hydrogen, $-NO_2$, $-NH_2$, $-SO_2R^9$, or $-CH_2R^9$;
$R^6$ is hydrogen, $C_1$ to $C_6$ alkyl, $C_3$ to $C_6$ alkenyl, $-CH_2CH_2Z$, $-CH_2COR^7$, $-CH_2CH=CHCOR^7$,

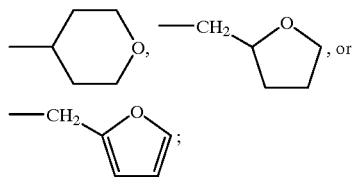

$Y^1$ and $Y^3$ are each, independently, N, or CH;
$Y^2$ and $Y^4$ are each independently, O, S, or $NR^{13}$;
$R^7$ is $-OR^8$, $-NHR^8$, $-N(R^8)_2$, or $-NHCH_2CH_2OR^8$;
Z is $-OR^8$, $-OCH_2CH_2OR^8$, $-N(R^8)_2$, or

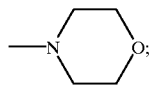

$R^8$ is hydrogen, or $C_1$ to $C_3$ alkyl;
$R^9$ is $C_1$ to $C_6$ alkyl, $C_3$ to $C_6$ alkenyl, OH, $NHR^{10}$, $N(R^{10})_2$, $CH_2COR^{11}$, $-CH_2CH=CHCOR^{11}$, or

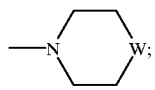

$R^{10}$ is $C_1$ to $C_3$ alkyl, $C_3$ to $C_4$ alkenyl, phenyl, $-CH_2CH_2OCH_3$, or

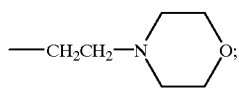

$R^{11}$ is $-OR^{12}$, $-NHR^{12}$, $-N(R^{12})_2$, or $-NHCH_2CH_2OR^{12}$;
$R^{12}$ is hydrogen, or $C_1$ to $C_3$ alkyl;
$R^{13}$ is hydrogen, or $C_1$ to $C_3$ alkyl;
W is a bond, $CH_2$, $CH_2CH_2$, O, $S(O)_q$, NCHO, $NCOCH_3$, or $NR^{12}$;
m is 0–2;
n is 0–2;

q is 0–2,
with the proviso that $R^2$ and $R^3$ are not both hydrogen;
or pharmaceutically acceptable salt thereof.

2. A method of providing contraception in a male mammal in need thereof which comprises administering to said mammal a contraceptive effective amount of a compound of formula I having the structure

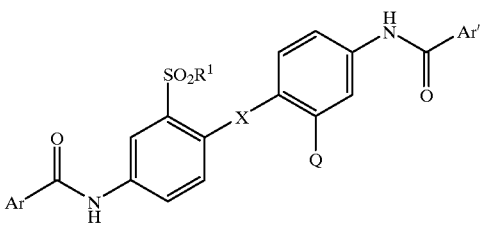

(I)

wherein

Q is hydrogen or $-SO_2R^1$;
X is a bond, O, $S(O)_n$, $-CH=CH-$, $-CH_2CH_2-$, $-C\equiv C-$, or $-CH_2S(O)_nCH_2-$;
$R^1$ is OH, $NH_2$, $C_1$ to $C_6$ alkoxy, $C_1$ to $C_3$ perfluoroalkoxy;
Ar is

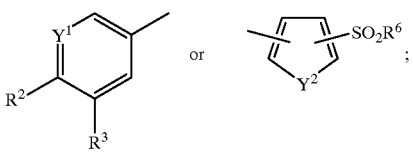

Ar' is

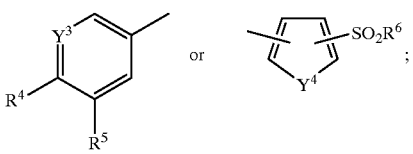

$R^2$ and $R^4$ are each, independently, hydrogen, $OR^6$, $-S(O)_mR^6$, $-NHR^6$, $-N(R^6)_2$, or $-CH_2SO_2CH_3$;
$R^3$ and $R^5$ are each, independently, hydrogen, $-NO_2$, $-NH_2$, $-SO_2R^9$, or $-CH_2R^9$;
$R^6$ is hydrogen, $C_1$ to $C_6$ alkyl, $C_3$ to $C_6$ alkenyl, $-CH_2CH_2Z$, $-CH_2COR^7$, $-CH_2CH=CHCOR^7$,

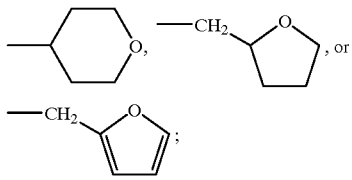

$Y^1$ and $Y^3$ are each, independently, N, or CH;
$Y^2$ and $Y^4$ are each independently, O, S, or $NR^{13}$;
$R^7$ is $-OR^8$, $-NHR^8$, $-N(R^8)_2$, or $-NHCH_2CH_2OR^8$;

Z is —OR$^8$, —OCH$_2$CH$_2$OR$^8$, —N(R$^8$)$_2$, or

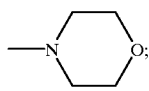

R$^8$ is hydrogen, or C$_1$ to C$_3$ alkyl;
R$^9$ is C$_1$ to C$_6$ alkyl, C$_3$ to C$_6$ alkenyl, OH, NHR$^{10}$, N(R$^{10}$)$_2$, CH$_2$COR$^{11}$, —CH$_2$CH=CHCOR$^{11}$, or

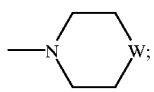

R$^{10}$ is C$_1$ to C$_3$ alkyl, C$_3$ to C$_4$ alkenyl, phenyl, —CH$_2$CH$_2$OCH$_3$, or

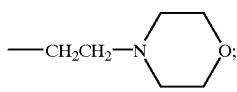

R$^{11}$ is —OR$^{12}$, —NHR$^{12}$, —N(R$^{12}$)$_2$, or —NHCH$_2$CH$_2$OR$^{12}$;
R$^{12}$ is hydrogen, or C$_1$ to C$_3$ alkyl;
R$^{13}$ is hydrogen, or C$_1$ to C$_3$ alkyl;
W is a bond, CH$_2$, CH$_2$CH$_2$, O, S(O)$_q$, NCHO, NCOCH$_3$, or NR$^{12}$;
m is 0–2;
n is 0–2;
q is 0–2,
with the proviso that R$^2$ and R$^3$ are not both hydrogen; or pharmaceutically acceptable salt thereof.

3. A pharmaceutical composition which comprises, a compound of formula I having the structure

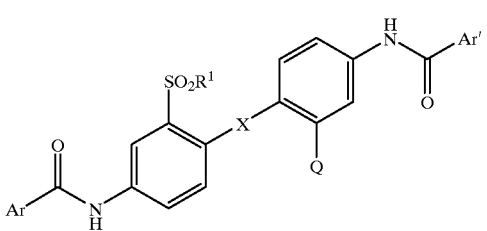

(I)

wherein
Q is hydrogen or —SO$_2$R$^1$;
X is a bond, O, S(O)$_n$, —CH=CH—, —CH$_2$CH$_2$—, —C≡C—, or —CH$_2$S(O)$_n$CH$_2$;
R$^1$ is OH, NH$_2$, C$_1$ to C$_6$ alkoxy, C$_1$ to C$_3$ perfluoroalkoxy;

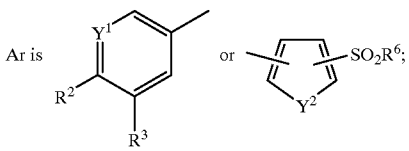

Ar is

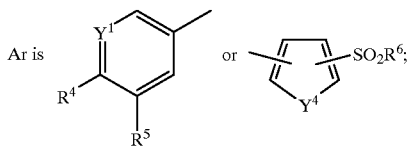

R$^2$ and R$^4$ are each, independently, hydrogen, OR$^6$, —S(O)$_m$R$^6$, —NHR$^6$, —N(R$^6$)$_2$, or —CH$_2$SO$_2$CH$_3$;
R$^3$ and R$^5$ are each, independently, hydrogen, —NO$_2$, —NH$_2$, —SO$_2$R$^9$, or —CH$_2$R$^9$;
R$^6$ is hydrogen, C$_1$ to C$_6$ alkyl, C$_3$ to C$_6$ alkenyl, —CH$_2$CH$_2$Z, —CH$_2$COR$^7$, —CH$_2$CH=CHCOR$^7$,

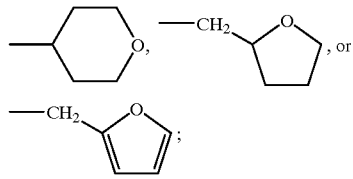

Y$^1$ and Y$^3$ are each, independently, N, or CH;
Y$^2$ and Y$^4$ are each independently, O, S, or NR$^{13}$;
R$^7$ is —OR$^8$, —NHR$^8$, —N(R$^8$)$_2$, or —NHCH$_2$CH$_2$OR$^8$;
Z is —OR$^8$, —OCH$_2$CH$_2$OR$^8$, —N(R$^8$)$_2$, or

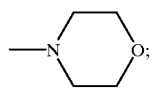

R$^8$ is hydrogen, or C$_1$ to C$_3$ alkyl;
R$^9$ is C$_1$ to C$_6$ alkyl, C$_3$ to C$_6$ alkenyl, OH, NHR$^{10}$, N(R$^{10}$)$_2$, CH$_2$COR$^{11}$, —CH$_2$CH=CHCOR$^{11}$, or

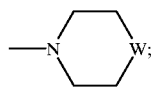

R$^{10}$ is C$_1$ to C$_3$ alkyl, C$_3$ to C$_4$ alkenyl, phenyl, —CH$_2$CH$_2$OCH$_3$, or

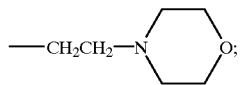

R$^{11}$ is —OR$^{12}$, NHR$^{12}$, —N(R$^2$)$_2$, or —NHCH$_2$CH$_2$OR$^{12}$;
R$^{12}$ is hydrogen, or C$_1$ to C$_3$ alkyl;
R$^{13}$ is hydrogen, or C$_1$ to C$_3$ alkyl;
W is a bond, CH$_2$, CH$_2$CH$_2$, O, S(O)$_q$, NCHO, NCOCH$_3$, or NR$^{12}$;
m is 0–2;
n is 0–2;
q is 0–2,
with the proviso that R$^2$ and R$^3$ are not both hydrogen; or pharmaceutically acceptable salt thereof, and a pharmaceutical carrier.

—CH$_2$CH=CHCOR$^7$,

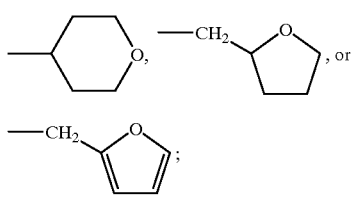

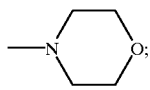

Y$^1$ and Y$^3$ are each, independently, N, or CH;
Y$^2$ and Y$^4$ are each independently, O, S, or NR$^{13}$;
R$^7$ is —OR$^8$, —NHR$^8$, —N(R$^8$)$_2$, or —NHCH$_2$CH$_2$OR$^8$;
Z is —OR$^8$, —OCH$_2$CH$_2$OR$^8$, —N(R$^8$)$_2$, or

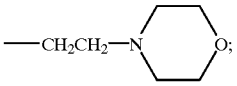

R$^8$ is hydrogen, or C$_1$ to C$_3$ alkyl;
R$^9$ is C$_1$ to C$_6$ alkyl, C$_3$ to C$_6$ alkenyl, OH, NHR$^{10}$, N(R$^{10}$)$_2$, CH$_2$COR$^{11}$, —CH$_2$CH=CHCOR$^{11}$, or

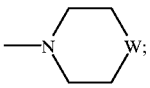

R$^{10}$ is C$_1$ to C$_3$ alkyl, C$_3$ to C$_4$ alkenyl, phenyl, —CH$_2$CH$_2$OCH$_3$, or —CH$_2$CH$_2$—N(morpholine);

R$^{11}$ is —OR$^{12}$, NHR$^{12}$, —N(R$^{12}$)$_2$, or —NHCH$_2$CH$_2$OR$^{12}$;
R$^{12}$ is hydrogen, or C$_1$ to C$_3$ alkyl;
R$^{13}$ is hydrogen, or C$_1$ to C$_3$ alkyl;
W is a bond, CH$_2$, CH$_2$CH$_2$, O, S(O)$_q$, NCHO, NCOCH$_3$, or NR$^{12}$;
m is 0–2;
n is 0–2;
q is 0–2,
with the proviso that R$^2$ and R$^3$ are not both hydrogen; or pharmaceutically acceptable salt thereof, which are useful as contraceptive agents.

* * * * *